US012708653B2

(12) United States Patent
Seth et al.

(10) Patent No.: US 12,708,653 B2
(45) Date of Patent: Aug. 18, 2026

(54) METHODS AND COMPOSITIONS COMPRISING ENHANCED TARGETED IMMUNE GENE THERAPY FOR THE TREATMENT OF CANCER

(71) Applicants: ENDEAVOR HEALTH CLINICAL OPERATIONS, Evanston, IL (US); MULTIVIR INC., Houston, TX (US)

(72) Inventors: Prem Seth, Evanston, IL (US); Sunil Chada, Houston, TX (US); Dora Wiederhold, Houston, TX (US); Kerstin B. Menander, Houston, TX (US); Robert E. Sobol, Houston, TX (US)

(73) Assignees: ENDEAVOR HEALTH CLINICAL OPERATIONS, Evanston, IL (US); MULTIVIR INC., Houston, TX (US)

( * ) Notice: Subject to any disclaimer, the term of this patent is extended or adjusted under 35 U.S.C. 154(b) by 1084 days.

(21) Appl. No.: 17/593,486

(22) PCT Filed: Mar. 25, 2020

(86) PCT No.: PCT/US2020/024593
§ 371 (c)(1),
(2) Date: Sep. 20, 2021

(87) PCT Pub. No.: WO2020/198293
PCT Pub. Date: Oct. 1, 2020

(65) Prior Publication Data

US 2022/0226402 A1 Jul. 21, 2022

Related U.S. Application Data

(60) Provisional application No. 62/823,304, filed on Mar. 25, 2019.

(51) Int. Cl.

| | |
|---|---|
| ***A61K 35/761*** | (2015.01) |
| ***A61K 38/17*** | (2006.01) |
| ***A61K 38/20*** | (2006.01) |
| ***A61K 39/395*** | (2006.01) |
| ***A61K 48/00*** | (2006.01) |
| ***A61P 35/00*** | (2006.01) |
| ***A61P 35/04*** | (2006.01) |
| ***C07K 14/71*** | (2006.01) |
| ***C12N 15/86*** | (2006.01) |

(52) U.S. Cl.
CPC ........ *A61K 35/761* (2013.01); *A61K 38/1793* (2013.01); *A61K 38/2086* (2013.01); *A61K 39/3955* (2013.01); *A61K 48/0008* (2013.01); *A61P 35/00* (2018.01); *A61P 35/04* (2018.01); *C07K 14/71* (2013.01); *C12N 15/86* (2013.01); *C07K 2319/30* (2013.01); *C07K 2319/32* (2013.01); *C12N 2710/10332* (2013.01); *C12N 2710/10343* (2013.01)

(58) Field of Classification Search
CPC ........ A61K 35/761; A61P 35/04; A61P 35/00; C07K 14/71; C12N 15/86
See application file for complete search history.

(56) References Cited

U.S. PATENT DOCUMENTS

| | | | |
|---|---|---|---|
| 8,067,567 B2 | 11/2011 | Yun et al. | |
| 9,689,000 B2 | 6/2017 | Yun et al. | |
| 2006/0257361 A1 | 11/2006 | Watanabe et al. | |
| 2007/0160578 A1 | 7/2007 | Waldmann et al. | |
| 2010/0098668 A1 | 4/2010 | Seth | |
| 2010/0254914 A1 | 10/2010 | Park et al. | |
| 2017/0044229 A1 | 2/2017 | Garcia et al. | |
| 2017/0151310 A1 | 6/2017 | Felber et al. | |
| 2017/0183403 A1 | 6/2017 | Boyman et al. | |
| 2018/0002384 A1* | 1/2018 | Franken | C12N 7/04 |
| 2019/0015510 A1* | 1/2019 | Makings | A61K 47/6851 |
| 2020/0270639 A1* | 8/2020 | Curiel | A61K 45/06 |

FOREIGN PATENT DOCUMENTS

| | | |
|---|---|---|
| WO | WO 1999/036548 | 7/1999 |
| WO | WO 2012/046943 | 4/2012 |
| WO | WO 2016/091375 | 6/2016 |
| WO | WO 2017/079746 | 5/2017 |
| WO | WO 2018/067873 | 4/2018 |

OTHER PUBLICATIONS

Roberts et al (Nature 441, 239-243 (2006). https://doi.org/10.1038/nature04721) (Year: 2006).*
Roberts et al (Nature 441, 239-243 (2006). Doi: 10.1038/nature04721) (Year: 2006).*
Xu et al (Mol Ther . Aug. 2014;22(8):1504-1517. doi: 10.1038/mt.2014.80. Epub May 5, 2014.) (Year: 2014).*
Cai et al (Molecular Medicine Reports 16: 6443-6458, 2017, DOI: 10.3892/mmr.2017.7487) (Year: 2017).*
Dmitriev et al., "An Adenovirus Vector with Genetically Modified Fibers Demonstrates Expanded Tropism via Utilization of a Coxsackievirus and Adenovirus Receptor-Independent Cell Entry Mechanism", *Journal of Virology Dec*, 72 (12) 9706-9713, 1998.
Hu et al., "Oncolytic Adenovirus Expressing Soluble TGFbeta Receptor II-Fc-mediated Inhibition of Established Bone Metastases: A Safe and Effective Systemic Therapeutic Approach for Breast Cancer", *Mol Ther*, 9:1609-1618, 2011.
Laakkonen et al., "A tumor-homing peptide with a targeting specificity related to lymphatic vessels", *Nat Med*, 8:751-755, 2002.
Luo et al., "LyP-1-conjugated nanoparticles for targeting drug delivery to lymphatic metastatic tumors", *Int J Pharm* 385, 150-156, 2010.

(Continued)

*Primary Examiner* — Peter Paras, Jr.
*Assistant Examiner* — Khoa Nhat Tran
(74) *Attorney, Agent, or Firm* — pH IP Law

(57) ABSTRACT

Provided herein are methods and compositions for treating cancer in an individual comprising administering to the individual an effective amount of an adenoviral vector with a genetically modified fiber incorporating a Lyp-1 peptide motif and at least one CD122/CD132 agonist and/or an immune checkpoint inhibitor.

6 Claims, 5 Drawing Sheets

Specification includes a Sequence Listing.

(56) References Cited

OTHER PUBLICATIONS

Mariathasan et al., Abstract 8O_PR TGF-ß signalling attenuates tumour response to PD-L1 checkpoint blockade by contributing to retention of T cells in the peritumoural stroma <https://eslide.etimeeringtech.com/esmoio2017/attendee/confcal/show/session/7>. *Annals of Oncology*, 28, 2017 Supplement 11.

Nemunaitis et al., Pilot trial of intravenous infusion of a replication-selective adenovirus (ONYX-015) in combination with chemotherapy or IL-2 treatment in refractory cancer patients. *Cancer Gene Ther*, 10:341-352, 2003.

PCT International Search Report and Written Opinion issued in International Application No. PCT/US2020/024593, dated Jun. 25, 2020.

Roberts et al., Hexon-chimaeric adenovirus serotype 5 vectors circumvent pre-existing anti-vector immunity. *Nature*, 441:239-243, 2006.

Seth et al., "Overcoming anti-PD-1 resistance by systemic delivery of an oncolytic adenovirus that targets TGF-beta", RePORT ) RePORTER (nih.gov) NIH Abstract, Jul. 3, 2018.

Wang et al., LyP-1 modification to enhance delivery of artemisinin or fluorescent probe loaded polymeric micelles to highly metastatic tumor and its lymphatics, *Mol Pharm*, 9:2646-2657,2012.

Xu et al., "Ad5/48 Hexon Oncolytic Virus Expressing sTGFβRIIFc Produces Reduced Hepatic and Systemic Toxicities and Inhibits Prostate Cancer Bone Metastases", *Mol Ther* 22(8): 1504-1517, 2014.

Xu et al., "Conditionally replicative adenovirus-based mda-7/IL-24 expression enhances sensitivity of colon cancer cells to 5-fluorouracil and doxorubicin", *J Gastroenterol*., 48(2):203-13, 2013.

Xu et al., "The systemic delivery of an oncolytic adenovirus expressing decorin inhibits bone metastasis in a mouse model of human prostate cancer", *Gene Therapy*, 22(3): 247-256, 2015.

Yu and Fang et al., Clinical Trials with Oncolytic Adenovirus in China, *Current Cancer Drug Targets*; 7:659-670, 2007.

* cited by examiner

****p<0.001 All Groups vs. Buffer
*** p<0.0025 AdLyp.sT+P+C vs. All Groups

SEQUENCE LISTING

```
<160> NUMBER OF SEQ ID NOS: 2

<210> SEQ ID NO 1
<211> LENGTH: 9
<212> TYPE: PRT
<213> ORGANISM: Artificial Sequence
<220> FEATURE:
<223> OTHER INFORMATION: LyP-1 peptide

<400> SEQUENCE: 1

Cys Gly Asn Lys Arg Thr Arg Gly Cys
1               5


<210> SEQ ID NO 2
<211> LENGTH: 1474
<212> TYPE: DNA
<213> ORGANISM: Artificial Sequence
<220> FEATURE:
<223> OTHER INFORMATION: pHexon

<400> SEQUENCE: 2

cgtgctggac aggggcccta cttttaagcc ctactctggc actgcctaca acgccctggc     60

tcccaagggt gccccaaatc cttgcgaatg ggatgaagct gctactgctc ttgaaataga    120

aaaaaagaat ggaggaggaa gcgacgctaa tcagatgcaa actcacgtat ttgggcaggc    180

gccttattct ggtataaata ttacaaagga gggtcttcaa ataggtattg atgcaaccaa    240

agaggaagat aatggaaagg aaatatatgc cgataaaaca tttcaacctg aacctcaaat    300

aggagaatct cagtggcagg atagtgataa ttactatgga gggagagtcc ttaaaaagac    360

taccccaatg aaaccatgtt acggttcata tgcaaaaccc acaaatgaaa atggagggca    420

agctaaattc aaaacacctg aaaaagaagg agaagaaccc aaagaaagtc aagtggaaat    480

gcaatttttc gatattccca gtactggcac cggtggcaat ggtacaaatg tcaacttcaa    540

acctaaagtg gtattgtaca gtgaagatgt agatatagaa accccagaca ctcatatttc    600

ttacatgccc ggcaaggaag atgcaagttc acgagaacta atgggccaac aatctatgcc    660

caacaggcct aattacattg cttttaggga caattttatt ggtctaatgt attacaacag    720

cacgggtaat atgggtgttc tggcgggcca agcatcgcag ttgaatgctg ttgtagattt    780

gcaagacaga aacacagagc tttcatacca gcttttgctt gattccattg gtgatagaac    840

caggtacttt tctatgtgga atcaggctgt tgacagctat gatccagatg ttagaattat    900

tgaaaatcat ggaactgaag atgaacttcc aaattactgc tttccactgg atggtgctgg    960

aactaacgca gtgtaccaag gtgtaaaagt taaaacaact aacaatacag aatgggaaaa   1020
```

-continued

```
agatacagca gtatcagaac acaatcagat aagagttgga aataattttg ccatggaaat   1080

caatctaaat gccaacctgt ggagaaattt cctgtactcc aacatagcgc tgtatttgcc   1140

cgacaagcta aagtacagtc cttccaacgt aaaaatttct gataacccaa acacctacga   1200

ctacatgaac aagcgagtgg tggctcccgg gttagtggac tgctacatta accttggagc   1260

acgctggtcc cttgactata tggacaacgt caacccattt aaccaccacc gcaatgctgg   1320

cctgcgctac cgctcaatgt tgctgggcaa tggtcgctat gtgcccttcc acatccaggt   1380

gcctcagaag ttctttgcca ttaaaacctc cttctcctgc cgggctcata cacctacgag   1440

tggaacttca ggaaggatgt taacatggtt ctgc                                1474
```

METHODS AND COMPOSITIONS COMPRISING ENHANCED TARGETED IMMUNE GENE THERAPY FOR THE TREATMENT OF CANCER

This application is a national phase application under 35 U.S.C. § 371 of International Application No. PCT/US2020/024593, filed Mar. 25, 2020, which claims the benefit of U.S. Provisional Patent Application No. 62/823,304, filed Mar. 25, 2019, the entirety of each of which is incorporated herein by reference in their entirety.

This invention was made with government support under grant No. 1R41CA224504-01A1 awarded by National Institutes of Health. The government has certain rights in the invention.

INCORPORATION OF SEQUENCE LISTING

The sequence listing that is contained in the file named "SOBLP0149US_ST25.txt", which is 3 KB (as measured in Microsoft Windows) and was created on Sep. 8, 2021, is filed herewith by electronic submission and is incorporated by reference herein.

BACKGROUND

1. Field

The present invention relates generally to the fields of biology and medicine. More particularly, it concerns methods and compositions that enhance the potency of viral immune gene therapies for cancer.

2. Description of Related Art

Clinical applications of adenoviral oncolytic and gene therapy vectors have been hindered by multiple impediments. For example, adenoviruses produce significant hepatoxicity which limits administration dose levels. In addition, the development of neutralizing antibodies reduces adenoviral infection of target tissues with systemic delivery, limits repeat administrations and significantly reduces transgene expression at the desired sites of action. To overcome these problems, several groups have worked on re-targeting adenoviral vectors by alterations of their natural tropism through modification of their hexon-fiber structure.

To address these issues, a chimeric Ad5/48 adenovirus termed mHAd.sTβRFc was created by Xu et al. where hypervariable regions of Ad5 hexon present in an Ad5-based vector expressing soluble transforming growth factor beta receptor II-Fc fusion protein (sTGβRIIFc), were replaced by those of Ad48. mHAd.sTβRFc, like Ad.sTβRFc, was replication competent and resulted in high levels of sTGβRIIFc expression. Compared to the unmodified Ad-5 Ad.sTβRFc vector, systemic delivery of mHAd.sTβRFc in nude mice resulted in much reduced systemic toxicity, and reduced liver sequestration. Ad.sTβRFc produced significant liver necrosis, and increases in alanine transaminase, aspartate transaminase, lactate dehydrogenase, tumor necrosis factor-α, and interleukin-6 levels, while mHAd.sTβRFc produced much reduced responses of these markers. Intravenous delivery of Ad.sTβRFc or mHAd.sTβRFc ($5\times10^{10}$ viral particles/mouse) in nude mice bearing PC-3-luc PCa bone metastases produced inhibition of bone metastases. Moreover, a larger dose of the mHAd.sTβRFc ($4\times10^{11}$ viral particles/mouse) was able to be administered without lethality permitting enhanced efficacy.

In addition to the evaluation of chimeric hexon fibers from adenoviral serotypes with different tissue tropism, other methods generally employed for drug targeting have also been considered to avoid liver sequestration and neutralizing antibodies. An example is the incorporation of tissue targeted peptides such as RGD into adenoviral hexons (Dmitreiv et al., 1998). However, there is an unmet need for improved adenoviral vectors that overcome the impediments of current systems.

SUMMARY

In a first embodiment, the present disclosure provides a chimeric adenoviral vector with a genetically modified fiber incorporating a LyP-1 peptide. The LyP-1 peptide may comprise the sequence SEQ ID NO:1 CGNKRTRGC.

In another embodiment, the present disclosure provides methods of treating cancer and hyperproliferative disorders in a subject comprising administering to the subject an effective amount of an adenoviral vector with a genetically modified fiber incorporating a LyP-1 peptide.

In certain aspects, the adenoviral vector with a genetically modified fiber incorporating a Lyp-1 peptide motif with or without a chimeric hexon is replication competent and engineered to express at least one therapeutic nucleic acid. In certain aspects, the therapeutic nucleic acid is useful for cancer treatment and encodes a least one soluble decoy receptor, tumor suppressor, immune stimulating, anti-angiogenic, prodrug activating, proapoptotic, chemotherapy sensitizing, radiation sensitizing, miRNA, siRNA, anti-sense, ribozyme or CRISPR gene editing sequence.

In certain aspects, the adenoviral vector with a genetically modified fiber incorporating a Lyp-1 peptide motif with or without a chimeric hexon is replication competent and engineered to express a therapeutic decoy receptor transgene to inhibit immunosuppressive agents such as transforming growth factor beta (TGF-beta) or interleukin 10 (IL10). In a particular embodiment, the therapeutic transgene is the soluble transforming growth factor beta receptor II-Fc fusion protein (sTGβRIIFc).

In certain aspects, the adenoviral vector with a genetically modified fiber incorporating a Lyp-1 peptide motif is combined with at least one immune checkpoint inhibitor. In certain aspects, the at least one checkpoint inhibitor is selected from an inhibitor of CTLA-4, PD-1, PD-L1, PD-L2, LAG-3, BTLA, B7H3, B7H4, TIM3, KIR, or A2aR. In some aspects, the at least one immune checkpoint inhibitor is an anti-CTLA-4 antibody. In some aspects, the anti-CTLA-4 antibody is tremelimumab or ipilimumab. In certain aspects, the at least one immune checkpoint inhibitor is an anti-killer-cell immunoglobulin-like receptor (KIR) antibody. In some embodiments, the anti-KIR antibody is lirilumab. In some aspects, the inhibitor of PD-L1 is durvalumab, atezolizumab, or avelumab. In some aspects, the inhibitor of PD-L2 is rHIgM12B7. In some aspects, the LAG3 inhibitor is IMP321, or BMS-986016. In some aspects, the inhibitor of A2aR is PBF-509.

In some aspects, at least one immune checkpoint inhibitor is a human programmed cell death 1 (PD-1) axis binding antagonist. In certain aspects, the PD-1 axis binding antagonist is selected from the group consisting of a PD-1 binding antagonist, a PDL1 binding antagonist and a PDL2 binding antagonist. In some aspects, the PD-1 axis binding antagonist is a PD-1 binding antagonist. In certain aspects, the PD-1 binding antagonist inhibits the binding of PD-1 to PDL1 and/or PDL2. In particular, the PD-1 binding antagonist is a monoclonal antibody or antigen binding fragment thereof. In some embodiments, the PD-1 binding antagonist is nivolumab, pembrolizumab, pidilizumab, AMP-514, REGN2810, CT-011, BMS 936559, MPDL328OA or AMP-224.

In some aspects, the adenoviral vector with a genetically modified fiber incorporating a Lyp-1 peptide motif is administered intratumorally, intraarterially, intravenously, intravascularly, intrapleuraly, intraperitoneally, intratracheally, intrathecally, intramuscularly, endoscopically, intralesionally, percutaneously, subcutaneously, regionally, stereotactically, or by direct injection or perfusion. In certain aspects, the subject is administered the adenoviral vector with a genetically modified fiber incorporating a Lyp-1 peptide motif after the at least one immune checkpoint inhibitor. In certain aspects, the subject is administered the adenoviral vector with a genetically modified fiber incorporating a Lyp-1 peptide motif before the at least one immune checkpoint inhibitor. In certain aspects, the subject is administered the adenoviral vector with a genetically modified fiber incorporating a Lyp-1 peptide motif simultaneously with the at least one immune checkpoint inhibitor. In particular aspects, the adenoviral vector is administered to the subject intratumorally or intravenously.

In another embodiment, the adenoviral vector with a genetically modified fiber incorporating a Lyp-1 peptide motif is combined with at least one CD122/CD132 agonist. In certain aspects, the CD122/CD132 agonist preferentially binds to the CD122/CD132 receptor complex and has lower affinity binding for CD25 or the IL15 alpha receptor as compared to the affinity binding to the CD122/CD132 receptor complex. In specific aspects, the one or more CD122/CD132 agonists are an IL-2/anti-IL-2 immune complex, an IL-15/anti-IL-15 immune complex, an IL-15/IL-15 Receptor α-IgG1-Fc (IL-15/IL-15Rα-IgG1-Fc) immune complex, PEGylated IL-2, PEGylated IL-15, IL-2 mutein and/or IL-15 mutein. In particular aspects, the IL-2 receptor agonist is not F42K.

In some aspects, the adenoviral vector with a genetically modified fiber incorporating a Lyp-1 peptide motif delivers the nucleic acid encoding p53 and/or the nucleic acid encoding MDA-7. In certain aspects, the nucleic acid encoding p53 and/or the nucleic acid encoding MDA-7 is delivered in an expression cassette. In some aspects, p53 and MDA-7 are under the control of a single promoter, such as cytomegalovirus (CMV), SV40, or PGK. In certain aspects, the adenoviral Lyp-1 p53 (Ad-Lyp-1p53) adenoviral Lyp-1 IL24 (Ad-Lyp-1IL24) injection dose (mL) results in each tumor lesion receiving a dose of at least $1\times10^{11}$ viral particles (vp)/cm3 of tumor volume.

In some aspects, the adenoviral vector with a genetically modified fiber incorporating a Lyp-1 peptide motif is administered to the subject intravenously, intraarterially, intravascularly, intrapleuraly, intraperitoneally, intratracheally, intratumorally, intrathecally, intramuscularly, endoscopically, intralesionally, percutaneously, subcutaneously, regionally, stereotactically, or by direct injection or perfusion. In particular aspects, the adenoviral vector with a genetically modified fiber incorporating a Lyp-1 peptide motif is administered to the subject intravenously. In some aspects, administering comprises a local or regional injection. In some aspects, administering is via continuous infusion, intratumoral injection, or intravenous injection.

In some aspects, the subject is administered the adenoviral vector with a genetically modified fiber incorporating a Lyp-1 peptide motif more than once. In certain aspects, the subject is administered the additional cancer therapy more than once. In some aspects, the subject is administered the adenoviral vector with a genetically modified fiber incorporating a Lyp-1 peptide motif before, simultaneously, or after the at least one additional cancer therapy.

In some aspects, the cancer is melanoma, non-small cell lung, small-cell lung, lung, hepatocarcinoma, retinoblastoma, astrocytoma, glioblastoma, leukemia, neuroblastoma, head, neck, breast, pancreatic, prostate, renal, bone, testicular, ovarian, mesothelioma, cervical, gastrointestinal, urogenital, respiratory tract, hematopoietic, musculoskeletal, neuroendocrine, carcinoma, sarcoma, central nervous system, peripheral nervous system, lymphoma, brain, colon or bladder cancer. In particular aspects, the cancer is metastatic.

In some aspects, the method further comprises administering at least one additional anticancer treatment. In certain aspects, the at least one additional anticancer treatment is surgical therapy, chemotherapy, radiation therapy, hormonal therapy, immunotherapy, small molecule therapy, receptor kinase inhibitor therapy, anti-angiogenic therapy, cytokine therapy, cryotherapy, radioablation or a biological therapy. In some aspects, the biological therapy is a monoclonal antibody, siRNA, miRNA, antisense oligonucleotide, ribozyme, gene editing, cellular therapy or gene therapy.

In some aspects, the at least one additional anticancer treatment is an immune checkpoint inhibitor. In certain aspects the immune checkpoint inhibitor is of CTLA-4, PD-1, PD-L1, PD-L2, LAG-3, BTLA, B7H3, B7H4, TIM3, KIR, A2aR or CD47. In some aspects, the at least one immune checkpoint inhibitor is an anti-CTLA-4 antibody. In some aspects, the anti-CTLA-4 antibody is tremelimumab or ipilimumab. In certain aspects, the at least one immune checkpoint inhibitor is an anti-killer-cell immunoglobulin-like receptor (KIR) antibody. In some embodiments, the anti-KIR antibody is lirilumab. In some aspects, the inhibitor of PD-L1 is durvalumab, atezolizumab, or avelumab. In some aspects, the inhibitor of PD-L2 is rHIgM12B7. In some aspects, the LAG3 inhibitor is IMP321, or BMS-986016. In some aspects, the inhibitor of A2aR is PBF-509. In some aspects, the at least one immune checkpoint inhibitor is a human programmed cell death 1 (PD-1) axis binding antagonist. In certain aspects, the PD-1 axis binding antagonist is selected from the group consisting of a PD-1 binding antagonist, a PDL1 binding antagonist and a PDL2 binding antagonist. In some aspects, the PD-1 axis binding antagonist is a PD-1 binding antagonist. In certain aspects, the PD-1 binding antagonist inhibits the binding of PD-1 to PDL1 and/or PDL2. In particular, the PD-1 binding antagonist is a monoclonal antibody or antigen binding fragment thereof. In some embodiments, the PD-1 binding antagonist is nivolumab, pembrolizumab, pidilizumab, AMP-514, REGN2810, CT-011, BMS 936559, MPDL328OA or AMP-224.

In some aspects, the at least one additional therapy is a histone deacetylase (HDAC) inhibitor. In certain aspects, the HDAC inhibitor is tractinostat (CHR-3996 or VRx-3996). In certain aspects, the method further comprises providing an extracellular matrix-degrading protein, such as relaxin, hyaluronidase or decorin.

In some aspects, the at least one additional anticancer treatment is a replicating oncolytic or non-replicating virus. In some aspects, replicating oncolytic or non-replicating virus is engineered to express p53, MDA-7, IL-12, TGF-β inhibitor, and/or IL-10 inhibitor. In certain aspects, the replicating oncolytic or non-replicating virus is a single- or double-stranded DNA virus, RNA virus, adenovirus, adeno-associated virus, retrovirus, lentivirus, herpes virus, pox virus, vaccinia virus, vesicular stomatitis virus, polio virus, Newcastle's Disease virus, Epstein-Barr virus, influenza virus, reoviruses, myxoma virus, maraba virus, rhabdovirus, enadenotucirev or coxsackie virus. In some aspects, the oncolytic virus is engineered to express a cytokine, such as granulocyte-macrophage colony-stimulating factor (GM-CSF) or IL-12. In some aspects, the replicating oncolytic or non-replicating virus is further defined as talimogene laherparepvec (T-VEC). In some aspects, the replicating oncolytic or non-replicating adenoviral vector is derived from an E1b deleted adenovirus, and adenovirus where the Ad E1a gene is driven by the alpha-fetoprotein (AFP) promoter, a modified TERT Promoter Oncolytic Adenovirus, the HRE-E2F-TERT Hybrid Promoter Oncolytic Adenovirus, and/or an adenovirus with a modified E1a regulatory sequence wherein at least one Pea3 binding site, or a functional portion thereof, is deleted with an Elb-19K clone insertion site, which may all be modified to express therapeutic genes.

In certain aspects, the at least one additional anticancer treatment is a protein kinase or growth factor signaling pathways inhibitor. In certain aspects, the protein kinase or growth factor signaling pathways inhibitor is Afatinib, Axitinib, Bevacizumab, Bosutinib, Cetuximab, Crizotinib, Dasatinib, Erlotinib, Fostamatinib, Gefitinib, Imatinib, Lapatinib, Lenvatinib, Mubritinib, Nilotinib, Panitumumab, Pazopanib, Pegaptanib, Ranibizumab, Ruxolitinib, Saracatinib, Sorafenib, Sunitinib, Trastuzumab, Vandetanib, AP23451, Vemurafenib, CAL101, PX-866, LY294002, rapamycin, temsirolimus, everolimus, ridaforolimus, Alvocidib, Genistein, Selumetinib, AZD-6244, Vatalanib, P1446A-05, AG-024322, ZD1839, P276-00 or GW572016. In some aspects, the protein kinase inhibitor is a PI3K inhibitor, such as a PI3K delta inhibitor.

In some aspects, the immunotherapy comprises a cytokine, such as GM-CSF, an interleukin (e.g., IL-2) and/or an interferon (e.g., IFN$\alpha$) or heat shock proteins. In certain aspects, the immunotherapy comprises a co-stimulatory receptor agonist, a stimulator of innate immune cells, or an activator of innate immunity. In certain aspects, the co-stimulatory receptor agonist is an anti-OX40 antibody, anti-GITR antibody, anti-CD137 antibody, anti-CD40 antibody, an anti-CD27 antibody or anti-CD278 antibody. In some aspects, the stimulator of immune cells is an inhibitor of a cytotoxicity-inhibiting receptor or an agonist of immune stimulating toll like receptors (TLR). In some aspects, the cytotoxicity-inhibiting receptor is an inhibitor of NKG2A/CD94 or CD96 TACTILE. In some aspects, the TLR agonist is a TLR7 agonist, TLR8 agonist, or TLR9 agonist. In some aspects, the immunotherapy comprises a combination of a PD-L1 inhibitor, a 4-1BB agonist, and an OX40 agonist. In certain aspects, the immunotherapy comprises a stimulator of interferon genes (STING) agonist. In some aspects, the activator of innate immunity is an IDO inhibitor, TGF$\beta$ inhibitor, or IL-10 inhibitor. In some aspects, when these immunotherapies are proteins, they may be delivered as polypeptides or their corresponding nucleic acids administered by replication competent and/or replication incompetent viral and/or non-viral gene therapy. In some aspects, the chemotherapy comprises a DNA damaging agent, such as gamma-irradiation, X-rays, UV-irradiation, microwaves, electronic emissions, adriamycin, 5-fluorouracil (5FU), capecitabine, etoposide (VP-16), camptothecin, actinomycin-D, mitomycin C, cisplatin (CDDP), or hydrogen peroxide.

In another embodiment, there is provided a method of treating cancer in a subject comprising administering an effective amount of at least one adenoviral vector with a genetically modified fiber incorporating a Lyp-1 peptide motif and at least one CD122/CD132 agonist to the subject.

In some aspects, the least one adenoviral vector with a genetically modified fiber incorporating a Lyp-1 peptide motif is engineered to express p53, MDA-7, a cytokine, and/or immune stimulatory gene. In particular aspects, the cytokine is GM-CSF or IL-12. In some aspects, the immune stimulatory gene is an inhibitor of TGF$\beta$ or IL-10.

In some aspects, the adenoviral vector with a genetically modified fiber incorporating a Lyp-1 peptide motif is combined with the at least one oncolytic virus is selected from the group consisting of a single- or double-stranded DNA virus, RNA virus, adenovirus, adeno-associated virus, retrovirus, lentivirus, herpes virus, pox virus, vaccinia virus, vesicular stomatitis virus, polio virus, Newcastle's Disease virus, Epstein-Barr virus, influenza virus, reoviruses, myxoma virus, maraba virus, rhabdovirus, enadenotucirev, and coxsackie virus.

In some aspects, the viruses employed in the above embodiments comprise replication competent and/or replication defective viruses. In certain aspects, the replication competent or replication incompetent virus is a single or double stranded DNA virus, RNA virus, adenovirus, adeno-associated virus, retrovirus, lentivirus, herpes virus, pox virus, vaccinia virus, vesicular stomatitis virus, polio virus, Newcastle's Disease virus, myxoma virus, Epstein-Barr virus, influenza virus, reovirus, maraba virus, rhabdovirus, enadenotucirev or coxsackie virus. In certain aspects, one or more viruses are utilized. In certain aspects, the virus composition comprises a combination of replication competent and replication incompetent viruses.

In further aspects, the replication competent viruses in the above embodiments may be one or more oncolytic viruses. These oncolytic viruses may be engineered to express p53 and/or IL24 and/or to express a gene other than p53 and/or IL24, such as a cytokine (e.g. IL12) and/or another immune stimulatory gene (e.g., TGF-beta inhibitors or IL10 inhibitors or heat shock proteins). In certain aspects, the oncolytic virus may be used in lieu of or in addition to p53 and/or IL24 tumor suppressor therapy. Examples of oncolytic viruses include single or double stranded DNA viruses, RNA viruses, adenoviruses, adeno-associated viruses, retroviruses, lentiviruses, herpes viruses, pox viruses, vaccinia viruses, vesicular stomatitis viruses, polio viruses, Newcastle's Disease viruses, Epstein-Barr viruses, influenza viruses and reoviruses, myxoma viruses, maraba viruses, rhabdoviruses, enadenotucirev or coxsackie viruses. Exemplary oncolytic viruses include, but are not limited to, Ad5-yCD/mutTKSR39rep-hIL12, Cavatak™, CG0070, DNX-2401, G207, HF10, IMLYGIC™, JX-594, MG1-MA3, MV-NIS, OBP-301, Reolysin®, Toca 511, Oncorine (H101), Onyx-015, H102, H103, RIGVIR, an adenovirus overexpressing the adenoviral death protein (ADP), such as VirRx007, an N1L deleted vaccinia virus or an N1L deleted vaccinia virus expressing IL12.

In some aspects, the viral and non-viral nucleic acid and gene editing compositions induce local and/or systemic effects. In some aspects, these compositions induce local and systemic effects.

In particular aspects, the treated subject is a mammal or human. In certain aspects, the treatment is provided to prevent or treat a pre-malignant or a malignant hyperproliferative condition. In certain aspects of prevention, the subject is a healthy subject. In other aspects of prevention, the subject comprises a pre-malignant lesion, such as, for example, a leukoplakia or a dysplastic lesion. In other aspects of prevention, the subject is at risk of developing cancer, such as, for example, by being a smoker or having a family history of cancer. In certain aspects, the treatment is for initial or recurrent hyperproliferative conditions. In some aspects, the treatment is administered to augment or reverse resistance to another therapy. In certain aspects, the resistance to treatment is known historically for a particular population of hyperproliferative condition patients. In certain aspects, the resistance to treatment is observed in individual hyperproliferative condition patients.

In certain aspects of the above embodiments, the method further comprises providing an extracellular matrix-degrading protein. In some aspects, this comprises administering an expression cassette encoding the extracellular matrix-degrading protein. In some embodiments, the extracellular matrix-degrading protein is relaxin, hyaluronidase or decorin. In particular aspects, the extracellular matrix-degrading protein is relaxin. In some aspects, the expression cassette is in a viral vector. In certain aspects, the viral vector is an adenoviral vector, a retroviral vector, a vaccinia viral vector, an adeno-associated viral vector, a herpes viral vector, a vesicular stomatitis viral vector, or a polyoma viral vector or another type of viral or non-viral gene therapy vector.

In some aspects, the expression cassette encoding the extracellular matrix-degrading protein is administered intratumorally, intraarterially, intravenously, intravascularly, intrapleuraly, intraperitoneally, intratracheally, intrathecally, intramuscularly, endoscopically, intralesionally, percutaneously, subcutaneously, regionally, stereotactically, or by direct injection or perfusion. In certain aspects, the subject is administered the adenoviral vector with a genetically modified fiber incorporating a Lyp-1 peptide motif after the at least one CD122/CD132 agonist. In certain aspects, the subject is administered the adenoviral vector with a genetically modified fiber incorporating a Lyp-1 peptide motif before the at least one CD122/CD132 agonist. In certain aspects, the subject is administered the adenoviral vector with a genetically modified fiber incorporating a Lyp-1 peptide motif simultaneously with the at least one CD122/CD132 agonist. In particular aspects, the adenoviral vector is administered to the subject intratumorally. In some aspects, the adenoviral vector with a genetically modified fiber incorporating a Lyp-1 peptide motif and at least one CD122/CD132 agonist induce abscopal (systemic) effects on distant tumors that are not injected with the adenoviral vector with a genetically modified fiber incorporating a Lyp-1 peptide motif.

In certain aspects, the cancer is melanoma, non-small cell lung, small-cell lung, lung, hepatocarcinoma, retinoblastoma, astrocytoma, glioblastoma, leukemia, neuroblastoma, head, neck, breast, pancreatic, prostate, renal, bone, testicular, ovarian, mesothelioma, cervical, gastrointestinal, urogenital, respiratory tract, hematopoietic, musculoskeletal, neuroendocrine, carcinoma, sarcoma, central nervous system, peripheral nervous system, lymphoma, brain, colon or bladder cancer. In some aspects, the cancer is metastatic.

In some aspects, the nucleic acid encoding p53 and/or the nucleic acid encoding MDA-7 is in an expression cassette. In certain aspects, the expression cassette is in a viral vector. In some embodiments, the viral vector is an adenoviral vector, a retroviral vector, a vaccinia viral vector, an adeno-associated viral vector, a herpes viral vector, a vesicular stomatitis viral vector, or a polyoma viral vector. In particular aspects, the viral vector is an adenoviral vector.

In certain aspects, the viral vector is administered at between about $10^3$ and about $10^{13}$ viral particles. In some aspects, the adenoviral vector is administered to the subject intravenously, intraarterially, intravascularly, intrapleuraly, intraperitoneally, intratracheally, intratumorally, intrathecally, intramuscularly, endoscopically, intralesionally, percutaneously, subcutaneously, regionally, stereotactically, or by direct injection or perfusion. In certain aspects, the subject is administered the adenoviral vector more than once.

In certain aspects, administering comprises a local or regional injection. In other aspects, administering is via continuous infusion, intratumoral injection, or intravenous injection.

In some aspects, the method further comprises administering at least one additional anticancer treatment. In certain aspects, the at least one additional anticancer treatment is surgical therapy, chemotherapy (e.g., administration of a protein kinase inhibitor or a EGFR-targeted therapy), embolization therapy, chemoembolization therapy, radiation therapy, cryotherapy, hyperthermia treatment, phototherapy, radioablation therapy, hormonal therapy, immunotherapy, small molecule therapy, receptor kinase inhibitor therapy, anti-angiogenic therapy, cytokine therapy or a biological therapies such as monoclonal antibodies, siRNA, miRNA, antisense oligonucleotides, ribozymes or gene therapy.

In some aspects, the immunotherapy comprises a cytokine. In particular aspects, the cytokine is granulocyte macrophage colony-stimulating factor (GM-CSF), an interleukin such as IL-2, and/or an interferon such as IFN-alpha. Additional approaches to boost tumor-targeted immune responses include additional immune checkpoint inhibition. In some aspects, the immune checkpoint inhibition includes anti-CTLA4, anti-PD-1, anti-PD-L1, anti-PD-L2, anti-TIM-3, anti-LAG-3, anti-A2aR, anti-KIR or anti-CD47 antibodies. In some aspects, the immunotherapy comprises co-stimulatory receptor agonists such as anti-OX40 antibody, anti-GITR antibody, anti-CD137 antibody, anti-CD40 antibody, anti-CD27 antibody or anti-CD278 antibody. In certain aspects, the immunotherapy comprises suppression of T regulatory cells (Tregs), myeloid derived suppressor cells (MDSCs) and cancer associated fibroblasts (CAFs). In further aspects, the immunotherapy comprises stimulation of innate immune cells, such as natural killer (NK) cells, macrophages, and dendritic cells. Additional immune stimulatory treatments may include IDO inhibitors, TGF-beta inhibitors, IL-10 inhibitors, stimulator of interferon genes (STING) agonists, toll like receptor (TLR) agonists (e.g., TLR7, TLR8, or TLR9), tumor vaccines (e.g., whole tumor cell vaccines, peptides, and recombinant tumor associated antigen vaccines), and adoptive cellular therapies(ACT) (e.g., T cells, natural killer cells, TILs, and LAK cells), and ACT with genetically engineered receptors (e.g., chimeric antigen receptors (CAR) and T cell receptors (TCR). In certain aspects, combinations of these agents may be used such as combining immune checkpoint inhibitors, checkpoint inhibition plus agonism of T-cell costimulatory receptors, and checkpoint inhibition plus TIL ACT. In certain aspects, additional anti-cancer treatment includes a combination of an immune checkpoint inhibitor (e.g., Avelumab), a 4-1BB (CD-137) agonist (e.g. Utomilumab), and an OX40 (TNFRS4) agonist.

In some aspects, the chemotherapy comprises a DNA damaging agent. In some embodiments, the DNA damaging agent is gamma-irradiation, X-rays, UV-irradiation, microwaves, electronic emissions, adriamycin, 5-fluorouracil (5FU), capecitabine, etoposide (VP-16). camptothecin. actinomycin-D, mitomycin C, cisplatin (CDDP), or hydrogen peroxide. In particular aspects, the DNA damaging agent is 5FU or capecitabine. In some aspects, the chemotherapy comprises a cisplatin (CDDP), carboplatin, procarbazine, mechlorethamine, cyclophosphamide, camptothecin, ifosfamide, melphalan, chlorambucil, bisulfan, nitrosurea, dactinomycin, daunorubicin, doxombicin, bleomycin, plicomycin, mitomycin, etoposide (VP16), tamoxifen, taxotere, taxol, transplatinum, 5-fluorouracil, vincristin, vinblastin, methotrexate, an HDAC inhibitor or any analog or derivative variant thereof.

In some aspects, the at least one additional cancer treatment is a protein kinase inhibitor or a monoclonal antibody that inhibits receptors involved in protein kinase or growth factor signaling pathways. For example, the protein kinase or receptor inhibitor can be an EGFR, VEGFR, AKT, Erb1, Erb2, ErbB, Syk, Bcr-Abl, JAK, Src, GSK-3, PI3K, Ras, Raf, MAPK, MAPKK, mTOR, c-Kit, eph receptor or BRAF inhibitor. In particular aspects, the protein kinase inhibitor is a PI3K inhibitor. In some embodiments, the PI3K inhibitor is a PI3K delta inhibitor. For example, the protein kinase or receptor inhibitor can be Afatinib, Axitinib, Bevacizumab, Bosutinib, Cetuximab, Crizotinib, Dasatinib, Erlotinib, Fostamatinib, Gefitinib, Imatinib, Lapatinib, Lenvatinib, Mubritinib, Nilotinib, Panitumumab, Pazopanib, Pegaptanib, Ranibizumab, Ruxolitinib, Saracatinib, Sorafenib, Sunitinib, Trastuzumab, Vandetanib, AP23451, Vemurafenib, CAL101, PX-866, LY294002, rapamycin, temsirolimus, everolimus, ridaforolimus, Alvocidib, Genistein, Selumetinib, AZD-6244, Vatalanib, P1446A-05, AG-024322, ZD1839, P276-00, GW572016, or a mixture thereof. In certain aspects, the protein kinase inhibitor is an AKT inhibitor (e.g., MK-2206, GSK690693, A-443654, VQD-002, Miltefosine or Perifosine). In certain aspects, EGFR-targeted therapies for use in accordance with the embodiments include, but are not limited to, inhibitors of EGFR/ErbB 1/HER, ErbB2/Neu/HER2, ErbB3/HER3, and/or ErbB4/HER4. A wide range of such inhibitors are known and include, without limitation, tyrosine kinase inhibitors active against the receptor(s) and EGFR-binding antibodies or aptamers. For instance, the EGFR inhibitor can be gefitinib, erlotinib, cetuximab, matuzumab, panitumumab, AEE788; CI-1033, HKI-272, HKI-357, or EKB-569. The protein kinase inhibitor may be a BRAF inhibitor such as dabrafenib, or a MEK inhibitor such as trametinib.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
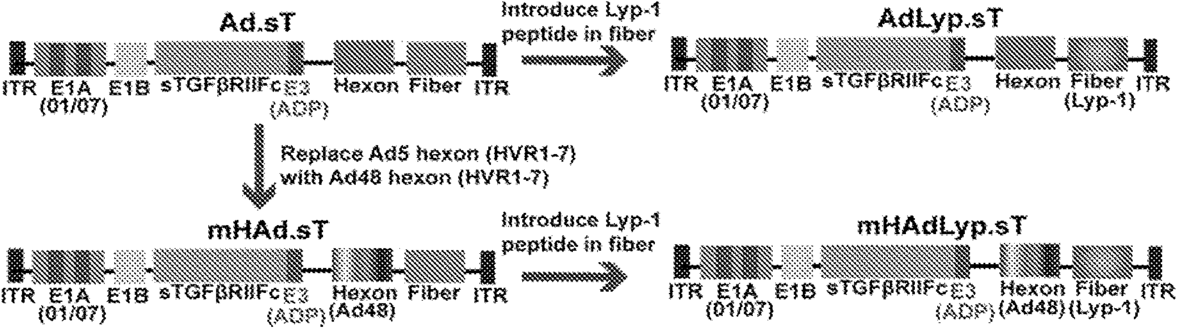
FIG. 1: Representative Lyp-1 Adenoviral Vector Constructs. To create AdLyp.sT, the Lyp-1 peptide sequence was introduced in the HI loop (fiber) of Ad.sT. To create mHAdLyp.sT, Ad5 hexon in AdLyP.sT HVRs 1-7 were replaced by the corresponding HVRs of Ad48 by genetic recombination. To create mHAdLyP.sT, Lyp-1 peptide, was introduced in the HI loop (fiber) of mHAd.sT by homologous recombination.
Figure 2:
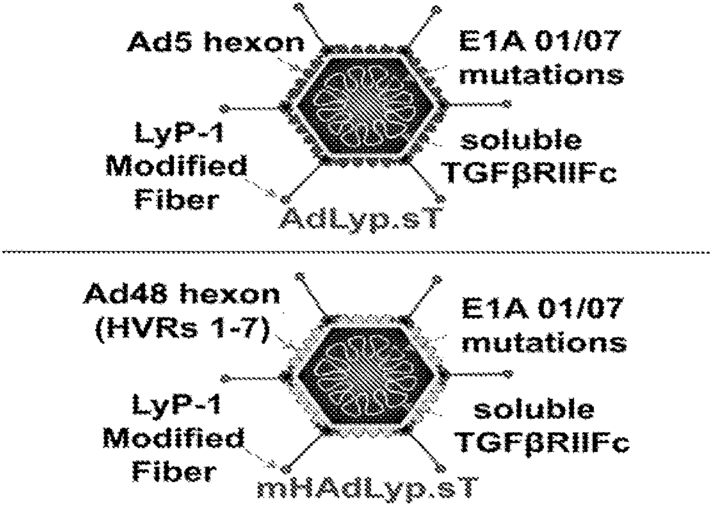
FIG. 2: Elements of Lyp-1 Adenoviral Vectors. Elements for AdLyp.sT (top) are shown which include E1A 01/07 mutations, sTGFβRIIFc gene, Lyp-1 modified fiber and Ad5 hexon, and of mHAdLyp.sT (bottom) which include E1A 01/07 mutations, sTGFβRIIFc gene, LyP-1 modified fiber and Ad5/48 hexon.
Figure 3:
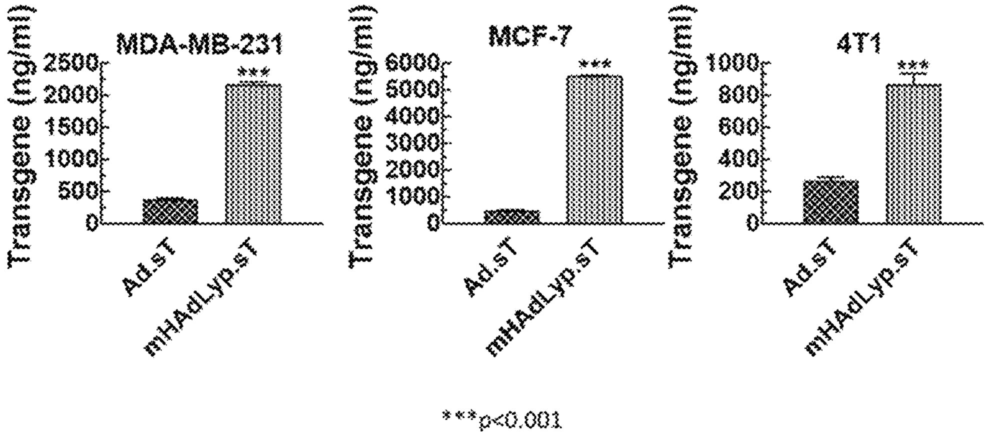
FIG. 3: Increased Transgene Expression of Lyp-1 Modified Adenoviral Vectors in Tumor Cells. MDA-MB-231, MCF-7, 4T1 cells were exposed to viral vectors ($2.5\times10^4$ VP/cell) and 48 hrs later, sTGFβRIIFc transgene expression levels were measured in the serum by ELISA. ***$p<0.001$, represents a highly significant increase in transgene expression for mHAdLyp.sT compared to the control Ad.sT).

Problems with systemic adenoviral gene therapy include significant hepatoxicity and the development of neutralizing antibodies that limit dosage levels and repeat administrations. These difficulties lower the therapeutic index of systemically administered adenoviral vectors significantly reducing transgene expression at the desired sites of action.

Accordingly, in the present studies, a series of replication competent adenoviral vectors were created with genetically modified fibers incorporating RGD, REA, LyP-1, or NGR peptide motifs with chimeric hexons to express therapeutic transgenes. These constructs were evaluated and compared with respect to multiple characteristics required for their successful use as systemic therapeutic agents. The tests included evaluations for virus stability, transgene expression and in vivo safety and efficacy. Unexpectedly, only the Lyp-1 modified constructs demonstrated virus stability and safety. Unpredictably, it also had the highest levels of transgene expression compared to the other constructs. The NGR peptide targeted virus was highly unstable and could not be generated. The REA virus was also very unstable frequently losing its transgene resulting in almost negligible levels of transgene protein expression. The RGD construct made reduced transgene protein compared to the Lyp-1 constructs and the RGD virus was lethal in murine animal models when administered intravenously at doses that were well tolerated with the Lyp-1 viruses. Approximately 50% of the population have Ad5 neutralizing antibodies and the Lyp-1 viruses were able to evade Ad5 neutralizing antibodies. The Lyp-1 viruses demonstrated statistically superior anti-tumor efficacy in vivo compared to conventional adenoviral constructs and synergistic efficacy in combination with immune checkpoint inhibitors.

Thus, in certain embodiments, the present disclosure provides methods and compositions for treating cancer and hyperproliferative disorders in a subject comprising administering to the subject an effective amount of an adenoviral vector with a genetically modified fiber incorporating a Lyp-1 peptide motif sequence. The adenoviral vector with a genetically modified fiber incorporating a Lyp-1 peptide motif may also contain a chimeric hexon.

The adenoviral vector may be replication competent and engineered to express at least one therapeutic nucleic acid. Exemplary therapeutic nucleic acids include a soluble decoy receptor, tumor suppressor, immune stimulating, anti-angiogenic, prodrug activating, proapoptotic, chemotherapy sensitizing, radiation sensitizing, miRNA, siRNA, anti-sense, ribozyme or CRISPR gene editing sequence. The construct may comprise one or more therapeutic nucleic acids. In particular, the construct may encode a therapeutic decoy receptor transgene to inhibit immunosuppressive agents such as transforming growth factor beta (TGFβ) or interleukin 10 (IL10). Specifically, the therapeutic transgene may be the soluble TGFβ receptor II-Fc fusion protein (sTGβRIIFc).

The LyP-1 vector may be combined with at least one immune checkpoint inhibitor, such as an inhibitor of CTLA-4, PD-1, PD-L1, PD-L2, LAG-3, BTLA, B7H3, B7H4, TIM3, KIR, or A2aR. Additionally, the inventors have determined that administering an additional therapy such as an immune checkpoint inhibitor like an anti-PD1 antibody enhances anti-tumor immunity either before, during or after the administration of the p53 and/or MDA-7 gene therapy in combination with a preferential CD122/CD132 agonist.

Further, the inventors have also determined that administering an additional therapy to degrade the tumor cell's extracellular matrix can enhance the tumor penetration of the combination therapies. Particularly, the extracellular matrix degrading therapy is administered before the combination therapy. In one method, the extracellular matrix degrading therapy is relaxin gene therapy, such as adenoviral relaxin. Particularly, the adenoviral relaxin is administered intratumorally or intraarterially.

Further, the methods of treatment can include additional anti-cancer therapies such as cytokines or chemotherapeutics to enhance the anti-tumor effect of the combination therapy provided herein. For example, the cytokine could be granulocyte macrophage colony-stimulating factor (GM-CSF) and the chemotherapy could be 5-fluorouracil (5FU) or capecitabine or cyclophosphamide or a PI3K inhibitor.

I. DEFINITIONS

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

The terms "about", "substantially" and "approximately" mean, in general, the stated value plus or minus 5%.

As used herein "wild-type" refers to the naturally occurring sequence of a nucleic acid at a genetic locus in the genome of an organism, and sequences transcribed or translated from such a nucleic acid. Thus, the term "wild-type" also may refer to the amino acid sequence encoded by the nucleic acid. As a genetic locus may have more than one sequence or alleles in a population of individuals, the term "wild-type" encompasses all such naturally occurring alleles. As used herein the term "polymorphic" means that variation exists (i.e., two or more alleles exist) at a genetic locus in the individuals of a population. As used herein, "mutant" refers to a change in the sequence of a nucleic acid or its encoded protein, polypeptide, or peptide that is the result of recombinant DNA technology.

The term "exogenous," when used in relation to a protein, gene, nucleic acid, or polynucleotide in a cell or organism refers to a protein, gene, nucleic acid, or polynucleotide that has been introduced into the cell or organism by artificial or natural means; or in relation to a cell, the term refers to a cell that was isolated and subsequently introduced to other cells or to an organism by artificial or natural means. An exogenous nucleic acid may be from a different organism or cell, or it may be one or more additional copies of a nucleic acid that occurs naturally within the organism or cell. An exogenous cell may be from a different organism, or it may be from the same organism. By way of a non-limiting example, an exogenous nucleic acid is one that is in a chromosomal location different from where it would be in natural cells, or is otherwise flanked by a different nucleic acid sequence than that found in nature.

By "expression construct" or "expression cassette" is meant a nucleic acid molecule that is capable of directing transcription. An expression construct includes, at a minimum, one or more transcriptional control elements (such as promoters, enhancers or a structure functionally equivalent thereof) that direct gene expression in one or more desired cell types, tissues or organs. Additional elements, such as a transcription termination signal, may also be included.

A "vector" or "construct" (sometimes referred to as a gene delivery system or gene transfer "vehicle") refers to a macromolecule or complex of molecules comprising a polynucleotide to be delivered to a host cell, either in vitro or in vivo.

A "plasmid," a common type of a vector, is an extra-chromosomal DNA molecule separate from the chromosomal DNA that is capable of replicating independently of the chromosomal DNA. In certain cases, it is circular and double-stranded.

"Homology" refers to the percent of identity between two polynucleotides or two polypeptides. The correspondence between one sequence and another can be determined by techniques known in the art. For example, homology can be determined by a direct comparison of the sequence information between two polypeptide molecules by aligning the sequence information and using readily available computer programs. Alternatively, homology can be determined by hybridization of polynucleotides under conditions that promote the formation of stable duplexes between homologous regions, followed by digestion with single strand-specific nuclease(s), and size determination of the digested fragments. Two DNA, or two polypeptide, sequences are "substantially homologous" to each other when at least about 80%, preferably at least about 90%, and most preferably at least about 95% of the nucleotides, or amino acids, respectively match over a defined length of the molecules, as determined using the methods above.

"Treating" or treatment of a disease or condition refers to executing a protocol, which may include administering one or more drugs to a patient, in an effort to alleviate signs or symptoms of the disease. Desirable effects of treatment include decreasing the rate of disease progression, ameliorating or palliating the disease state, and remission or improved prognosis. Alleviation can occur prior to signs or symptoms of the disease or condition appearing, as well as after their appearance. Thus, "treating" or "treatment" may include "preventing" or "prevention" of disease or undesirable condition. In addition, "treating" or "treatment" does not require complete alleviation of signs or symptoms, does not require a cure, and specifically includes protocols that have only a marginal effect on the patient.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, treatment of cancer may involve, for example, a reduction in the size of a tumor, a reduction in the invasiveness of a tumor, reduction in the growth rate of the cancer, or prevention of metastasis. Treatment of cancer may also refer to prolonging survival of a subject with cancer.

"Subject" and "patient" refer to either a human or non-human, such as primates, mammals, and vertebrates. In particular embodiments, the subject is a human.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds disclosed herein which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

A "pharmaceutically acceptable carrier," "drug carrier," or simply "carrier" is a pharmaceutically acceptable substance formulated along with the active ingredient medication that is involved in carrying, delivering and/or transporting a chemical agent. Drug carriers may be used to improve the delivery and the effectiveness of drugs, including for example, controlled-release technology to modulate drug bioavailability, decrease drug metabolism, and/or reduce drug toxicity. Some drug carriers may increase the effectiveness of drug delivery to the specific target sites. Examples of carriers include: liposomes, microspheres (e.g., made of poly(lactic-co-glycolic) acid), albumin microspheres, synthetic polymers, nanofibers, protein-DNA complexes, protein conjugates, erythrocytes, virosomes, and dendrimers.

The term "CD122/CD132 agonist" or "preferential CD122/CD132 agonist" refers to an agent that preferentially binds to the CD122/CD132 receptor complex and has lower affinity binding for the IL-2+ receptor (CD25) or the IL-15+ receptor. Known preferential CD122/CD132 agonists comprise an IL2/anti-IL2 monoclonal antibody immunocomplex (see, for example, U.S. Patent Publication No. US20170183403A1; incorporated herein by reference in its entirety); a genetically engineered IL-2 mutein that has a modified amino acid sequence compared to wild type IL-2 (see, for example, U.S. Patent Publication No. US 2017/0044229 A1; incorporated herein by reference in its entirety); a genetically engineered IL-2 mutein that has a modified amino acid sequence compared to wild type IL-2 combined with an anti-IL2 monoclonal antibody immunocomplex (see, for example, International Patent Publication No. WO2014100014A1; incorporated herein by reference in its entirety); a PEGylated form of IL-2, such as NKTR-214 (see, for example, Charych et al., 2016; incorporated herein by reference in its entirety), an IL-15/anti-IL-15 monoclonal antibody immunocomplex; an IL15/IL15 Receptor α-IgG1-Fc (IL15/IL15Rα-IgG1-Fc) immunocomplex (see, for example, U.S. Patent Publication No. US20060257361A1, EP2724728A1 and Dubois et al., 2008; all incorporated herein by reference); a genetically engineered IL-15 mutein that has a modified amino acid sequence compared to wild type IL-15 combined with an IL15Rα-IgG1-Fc immunocomplex (see, for example, U.S. Patent Publicaiton No. US20070160578; incorporated herein by reference in its entirety); or a PEGylated form of IL-15 with preferential binding to CD122/CD132.

The term "immune checkpoint" refers to a molecule such as a protein in the immune system which provides inhibitory signals to its components in order to balance immune reactions. Known immune checkpoint proteins comprise CTLA-4, PD-1 and its ligands PD-L1 and PD-L2 and in addition LAG-3, BTLA, B7H3, B7H4, TIM3, KIR. The pathways involving LAG3, BTLA, B7H3, B7H4, TIM3, and KIR are recognized in the art to constitute immune checkpoint pathways similar to the CTLA-4 and PD-1 dependent pathways (see e.g. Pardoll, 2012. Nature Rev Cancer 12:252-264; Mellman et al., 2011. Nature 480:480-489).

The term "PD-1 axis binding antagonist" refers to a molecule that inhibits the interaction of a PD-1 axis binding partner with either one or more of its binding partners, so as to remove T-cell dysfunction resulting from signaling on the PD-1 signaling axis—with a result being to restore or enhance T-cell function (e.g., proliferation, cytokine production, target cell killing). As used herein, a PD-1 axis binding antagonist includes a PD-1 binding antagonist, a PD-L1 binding antagonist and a PD-L2 binding antagonist.

The term "PD-1 binding antagonist" refers to a molecule that decreases, blocks, inhibits, abrogates or interferes with signal transduction resulting from the interaction of PD-1 with one or more of its binding partners, such as PD-L1 and/or PD-L2. In some embodiments, the PD-1 binding antagonist is a molecule that inhibits the binding of PD-1 to one or more of its binding partners. In a specific aspect, the PD-1 binding antagonist inhibits the binding of PD-1 to PD-L1 and/or PD-L2. For example, PD-1 binding antagonists include anti-PD-1 antibodies, antigen binding fragments thereof, immunoadhesins, fusion proteins, oligopeptides and other molecules that decrease, block, inhibit, abrogate or interfere with signal transduction resulting from the interaction of PD-1 with PD-L1 and/or PD-L2. In one embodiment, a PD-1 binding antagonist reduces the negative co-stimulatory signal mediated by or through cell surface proteins expressed on T lymphocytes mediated signaling through PD-1 so as render a dysfunctional T-cell less dysfunctional (e.g., enhancing effector responses to antigen recognition). In some embodiments, the PD-1 binding antagonist is an anti-PD-1 antibody. In a specific aspect, a PD-1 binding antagonist is MDX-1106 (nivolumab). In another specific aspect, a PD-1 binding antagonist is MK-3475 (pembrolizumab). In another specific aspect, a PD-1 binding antagonist is CT-011 (pidilizumab). In another specific aspect, a PD-1 binding antagonist is AMP-224.

The term "PD-L1 binding antagonist" refers to a molecule that decreases, blocks, inhibits, abrogates or interferes with signal transduction resulting from the interaction of PD-L1 with either one or more of its binding partners, such as PD-1 or B7-1. In some embodiments, a PD-L1 binding antagonist is a molecule that inhibits the binding of PD-L1 to its binding partners. In a specific aspect, the PD-L1 binding antagonist inhibits binding of PD-L1 to PD-1 and/or B7-1. In some embodiments, the PD-L1 binding antagonists include anti-PD-L1 antibodies, antigen binding fragments thereof, immunoadhesins, fusion proteins, oligopeptides and other molecules that decrease, block, inhibit, abrogate or interfere with signal transduction resulting from the interaction of PD-L1 with one or more of its binding partners, such as PD-1 or B7-1. In one embodiment, a PD-L1 binding antagonist reduces the negative co-stimulatory signal mediated by or through cell surface proteins expressed on T lymphocytes mediated signaling through PD-L1 so as to render a dysfunctional T-cell less dysfunctional (e.g., enhancing effector responses to antigen recognition). In some embodiments, a PD-L1 binding antagonist is an anti-PD-L1 antibody. In a specific aspect, an anti-PD-Ll antibody is YW243.55. S70. In another specific aspect, an anti-PD-Ll antibody is MDX-1105. In still another specific aspect, an anti-PD-L1 antibody is MPDL3280A. In still another specific aspect, an anti-PD-L1 antibody is MEDI4736.

The term "PD-L2 binding antagonist" refers to a molecule that decreases, blocks, inhibits, abrogates or interferes with signal transduction resulting from the interaction of PD-L2 with either one or more of its binding partners, such as PD-1. In some embodiments, a PD-L2 binding antagonist is a molecule that inhibits the binding of PD-L2 to one or more of its binding partners. In a specific aspect, the PD-L2 binding antagonist inhibits binding of PD-L2 to PD-1. In some embodiments, the PD-L2 antagonists include anti-PD-L2 antibodies, antigen binding fragments thereof, immunoadhesins, fusion proteins, oligopeptides and other molecules that decrease, block, inhibit, abrogate or interfere with signal transduction resulting from the interaction of PD-L2 with either one or more of its binding partners, such as PD-1. In one embodiment, a PD-L2 binding antagonist reduces the negative co-stimulatory signal mediated by or through cell surface proteins expressed on T lymphocytes mediated signaling through PD-L2 so as render a dysfunctional T-cell less dysfunctional (e.g., enhancing effector responses to antigen recognition). In some embodiments, a PD-L2 binding antagonist is an immunoadhesin.

An "immune checkpoint inhibitor" refers to any compound inhibiting the function of an immune checkpoint protein. Inhibition includes reduction of function and full blockade. In particular the immune checkpoint protein is a human immune checkpoint protein. Thus the immune checkpoint protein inhibitor in particular is an inhibitor of a human immune checkpoint protein.

An "extracellular matrix degradative protein" or "extracellular matrix degrading protein" refers any protein which acts on the integrity of the cell matrix, in particular exerting a total or partial degrading or destabilizing action on at least one of the constituents of the said matrix or on the bonds which unite these various constituents.

An "abscopal effect" is referred to herein as a shrinking of tumors outside the scope of the localized treatment of a tumor. For example, localized treatment with the p53 and/or IL-24 in combination with systemic treatment with an immune checkpoint therapy can result in an abscopal effect at distant untreated tumors.

II. CHIMERIC ADENOVIRAL VECTORS

The present disclosure concerns adenoviral vectors, particularly chimeric adenoviral vectors. The chimeric adenoviral vector can comprise a genetically modified fiber incorporating a LyP-1 peptide. The vector can further comprise a soluble receptor, such as soluble transforming growth factor beta receptor II-Fc fusion protein (sTGβRIIFc) to inhibit TGFβ signaling. In addition, the chimeric vector can comprise a chimeric hexon, Ad5/Ad48, such that the Ad5 serotype is replaced with the Ad5/Ad48 chimeric hexon. The Ad5/Ad48 chimeric hexon may be produced by replacing seven hypervariable regions of the Ad5 hexon with Ad48 regions. The adenoviral vectors used herein may have E1A 01/07 mutations.

An exemplary method for generating the present chimeric adenoviral vectors is described below.

Step 1. Cloning fiber gene in PCR vector. 3.36 kb Kpn-1 and Xba1fragment of fiber gene is excised from p309 adenoviral shuttle vector (p309CMV-polyA) and cloned in the PCR vector resulting in PCRFiber vector.

Step 2. Insertion of internal Cla1-Sal I sites in the fiber gene. Using the Fib 1412 forward and Cla-1Fiber 1638 reverse primers; and fiber gene as template, a 231 bp DNA fragment (fragment 1) is produced by PCR. Similarly a 200 bp fragment 2 is produced by using Sal-1Fiber 1638 forward and Fiber 1816-reverse primers. A 430 bp fragment is created by using fiber 1412 forward and Fiber 1816 reverse primers; and fragment 1 and fragment 2 as the DNA templates. This results in the production of 430 bp fragment that has internal Cla-1 and Sal-1 sites. A 7 Kb fragment (Bst-1/Bsb-1) is purified from the PCRFiber vector, and ligated with Bst-1-Bsb-1 cut fragment from PCR3 fragment. This results in the production of PCR-FiberHI vector. In this vector, the fiber gene has internal Cla1-Sal-1 sites in the HI loop.

Step 3. Insertion of Lyp-1 into the HI loop of fiber. Two oligos (sense and the antisense strands containing Sal-Cla-lends) of Lyp1 are annealed, and cloned in theSal-1 and Cla-1 restricted PCRFibHI vector. This results in the production of PCRFibHILyp-1 vectors respectively.

Step 4. Creation of p309FibH1Lyp-1. Homologous recombination is conducted between the 4 kb Xba-1/Kpn-1 fragment of PCRFibHILyp-1 and the Bst-1/Bsx-1 cut p309CMV. The resultant vector is termed p309FibHI-Lyp1.

Step 5. Creation of pTG07-4609TGFβRIIFc. sTGFβRIIFc is cloned into pTG07-4609 adenoviral genomic DNA. A 1.2-kb HindIII-ApaI fragment from pcDNA3/SR2F containing cDNA of the soluble form of TGF-β receptor II fused to human IgG Fc is first cloned in HindIIIand ApaI digested pBS-SK. The sTGFβ RIIFc cDNA is then cloned in p309 plasmid to produce shuttle vector p309/sTβRFc. The 15.7-kb PacI-NruI fragment from p309/sTβRFc is then cotransformed in *Escherichia coli* BJ5183 with BstBIand SpeI-cut adenoviral backbone plasmid pTG07-4609. Homologous recombination of the shuttle vector and plasmid pAd01/07 (pTG07-4609) produces adenoviral genome plasmid pTG07-4609TGFßRIIFc.

Step 6. Creation of AdLyp1.sTβRFc (current nomenclature AdLyp1.sT). p309FibHI-Lyp1 and pTG07-4609TGFßRIIFc (Bst1 cut) are subjected to Homologous recombination in BJ cells. The recombinant DNA is cut with Pac-1 and used to transfect 293 cells. After 14 days, cell lysates are prepared and recombinant adenoviruses AdLyp1.sTßRFc are purified by $CsCl_2$ gradient method.

Next, the Ad5 hexon is replaced with the Ad48 hexon to produce mHAdLyp.sT.

Step 1. Construction of pTGhxn.sT. The modified hexon (Ad5/48 HVRs 1-7) in introduced into the adenoviral genome (pTG07-4609, referred to as pTG) cloning vector:

- pTG cut with AscI+pShuttle-cmv cut with EcoRV→pSh-Asc
- pSh-Asc with NruI+pBR322 with NruI→pBR-N
- pBR-N with ApaI&HpaI+pHexon-synthesized with ApaI&HpaI→pBR-NAH
- pSh-Asc with XmnI&XbaI+pcDNA3 with NheI&EcoRV→pcDNA-XX
- pBR-NAH with HindIII&BamhI+pcDNA-XX with HindIII&BamhI→pcDNA3-hxn
- pcDNA3-hxn with XhoI+pTG viral DNA with SfiI→pTG-hxn
- pTG-hxn with BstI SpeI+p309-sTGFβRIIFc PacI→pTGhxn.sT pHexon-synthesized with ApaI and HpaI sites may be chemically synthesized. The hexon may have a sequence with at least 80% sequence identity, such as 81%, 82%, 83%, 84%, 85%, 86%, 87%, 88%, 89%, 90%, 91%, 92%, 93%, 94%, 95%, 96%, 97%, 98%, 99%, or 100% sequence identity to SEQ ID NO:2.

pHexon (SEQ ID NO:2) with ApaI and HpaI sites underlined.

cgtgctggacaggggccctacttttaagccctactc tggcactgcctacaacgccctggctcccaagggtg ccccaaatccttgcgaatgggatgaagctgctact gctcttgaaatagaaaaaaagaatggaggaggaag cgacgctaatcagatgcaaactcacgtatttgggc aggcgccttattctggtataaatattacaaaggag ggtcttcaaataggtattgatgcaaccaaagagga agataatggaaaggaaatatatgccgataaaacat ttcaacctgaacctcaaataggagaatctcagtgg caggatagtgataattactatggagggagagtcct taaaaagactaccccaatgaaaccatgttacggtt catatgcaaaacccacaaatgaaaatggagggcaa gctaaattcaaaacacctgaaaaagaaggagaaga acccaaagaaagtcaagtggaaatgcaatttttcg atattcccagtactggcaccggtggcaatggtaca aatgtcaacttcaaacctaaagtggtattgtacag tgaagatgtagatatagaaaccccagacactcata tttcttacatgcccggcaaggaagatgcaagttca cgagaactaatgggccaacaatctatgcccaacag gcctaattacattgcttttagggacaattttattg gtctaatgtattacaacagcacgggtaatatgggt gttctggcgggccaagcatcgcagttgaatgctgt tgtagatttgcaagacagaaacacagagctttcat accagcttttgcttgattccattggtgatagaacc aggtacttttctatgtggaatcaggctgttgacag ctatgatccagatgttagaattattgaaaatcatg gaactgaagatgaacttccaaattactgctttcca ctggatggtgctggaactaacgcagtgtaccaagg tgtaaaagttaaaacaactaacaatacagaatggg aaaaagatacagcagtatcagaacacaatcagata agagttggaaataattttgccatggaaatcaatct aaatgccaacctgtggagaaatttcctgtactcca acatagcgctgtatttgcccgacaagctaaagtac agtccttccaacgtaaaaatttctgataacccaaa cacctacgactacatgaacaagcgagtggtggctc -continued ccgggttagtggactgctacattaaccttggagca cgctggtcccttgactatatggacaacgtcaaccc atttaaccaccaccgcaatgctggcctgcgctacc gctcaatgttgctgggcaatggtcgctatgtgccc ttccacatccaggtgcctcagaagttctttgccat taaaacctccttctcctgccgggctcatacaccta cgagtggaacttcaggaaggatgttaacatggttc tgc Step 2. Construction of pAd5/48-HI-Lyp-1-TGFβIIRHFc. P309CMVpa-HI-Lyp-1-TGFβRIIFc is cut by NruI and PacI, to rescue the 15800 bp fragment, and the pTG07/01-hexon is digested by SpeI and BstBI to rescue the 31882 bp. Digested P309CMVpa-HI-Lyp-1-TGFβRIIFc, and pTG07/01-hexon are co-transfected into the BJ5183 competent cells for homologous recombination. The new generated plasmids are named pTG07/01-hexon-HI-Lyp-1-TGFβRIIFc. The plasmid is confirmed by digestion with PacI (2 bands), SpeI (2 bands) or NdeI (3 bands).

Step 3. Rescue the Ad5/48-HI-Lyp-1-TGFIIRHFc (the current nomenclature-mHAdLyp.sT. pTG07/01-hexon-HI-Lyp-1-TGFβRIIFc is cut with PacI, and then purified by phenol:chloroform. Purified products are transfected into 293 cells by using lipofectamine. After 10-14 days, cell lysates are prepared and recombinant adenovirus Ad5/48-HI-Lyp-1-TGFβRIIFc is purified by $CsCl_2$ gradient method. The expression of sTGFβRIIFc may be confirmed by using PCR, Western-blotting and ELISA.

Adenovirus growth and manipulation is known to those of skill in the art, and exhibits broad host range in vitro and in vivo. This group of viruses can be obtained in high titers, e.g., 109-1011 plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Knowledge of the genetic organization of adenovirus, a 36 kb, linear, double-stranded DNA virus, allows substitution of large pieces of adenoviral DNA with foreign sequences up to 7 kb (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification.

Adenovirus is particularly suitable for use as a gene transfer vector because of its mid-sized genome, ease of manipulation, high titer, wide target-cell range and high infectivity. Both ends of the viral genome contain 100-200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNA's issued from this promoter possess a 5'-tripartite leader (TPL) sequence which makes them particular mRNA's for translation.

A recombinant adenovirus provided herein can be generated from homologous recombination between a shuttle vector and provirus vector. Due to the possible recombination between two proviral vectors, wild-type adenovirus may be generated from this process. Therefore, a single clone of virus is isolated from an individual plaque and its genomic structure is examined.

The adenovirus vector may be replication competent, replication defective, or conditionally defective, the nature of the adenovirus vector is not believed to be crucial to the successful practice of the invention. The adenovirus may be of any of the 42 different known serotypes or subgroups A-F. Adenovirus type 5 of subgroup C is the particular starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

Nucleic acids can be introduced to adenoviral vectors as a position from which a coding sequence has been removed. For example, a replication defective adenoviral vector can have the E1-coding sequences removed. The polynucleotide encoding the gene of interest may also be inserted in lieu of the deleted E3 region in E3 replacement vectors as described by Karlsson et al. (1986) or in the E4 region where a helper cell line or helper virus complements the E4 defect.

Generation and propagation of replication deficient adenovirus vectors can be performed with helper cell lines. One unique helper cell line, designated 293, was transformed from human embryonic kidney cells by Ad5 DNA fragments and constitutively expresses E1 proteins (Graham et al., 1977). Since the E3 region is dispensable from the adenovirus genome (Jones and Shenk, 1978), adenovirus vectors, with the help of 293 cells, carry foreign DNA in either the E1, the E3, or both regions (Graham and Prevec, 1991).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, a particular helper cell line is 293.

Methods for producing recombinant adenovirus are known in the art, such as U.S. Pat. No. 6,740,320, incorporated herein by reference. Also, Racher et al. (1995) have disclosed improved methods for culturing 293 cells and propagating adenovirus. In one format, natural cell aggregates are grown by inoculating individual cells into 1 liter siliconized spinner flasks (Techne, Cambridge, UK) containing 100-200 ml of medium. Following stirring at 40 rpm, the cell viability is estimated with trypan blue. In another format, Fibra-Cel microcarriers (Bibby Sterlin, Stone, UK) (5 g/l) are employed as follows. A cell inoculum, resuspended in 5 ml of medium, is added to the carrier (50 ml) in a 250 ml Erlenmeyer flask and left stationary, with occasional agitation, for 1 to 4 hours. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 hours.

III. THERAPEUTIC NUCLEIC ACIDS

A. Tumor Suppressors

In some embodiments, a subject is administered a tumor suppressor therapy, such as a p53 and/or MDA-7 therapy. The nucleic acids encoding p53 and/or MDA-7 may be provided in various methods known in the art. In particular aspects, the nucleic acid encoding p53 and/or a nucleic acid encoding MDA-7 are delivered in an amount effective to restore or amplify tumor suppressor function. Other methods of restoring tumor suppressor function may also be utilized such as gene editing, inhibition of tumor suppressor degradation pathways, small molecule drugs to alter mutant tumor suppressor proteins or stabilized tumor suppressor peptides.

In some aspects, the p53 and MDA-7 tumor suppressor therapies incorporate nucleic acid variants to increase their activities. In certain aspects, the variant tumor suppressor nucleic acids are negative regulation-resistant p53 variants (Yun et al., 2012; incorporated herein by reference in its entirety).

1. p53

In certain embodiments, the present disclosure provides combination therapies for the treatment of cancer. Some of the combination therapies provided herein include p53 gene therapy comprising administering a wild-type p53 gene to the subject. Wild-type p53 is recognized as an important growth regulator in many cell types. The p53 gene encodes a 375-amino-acid phosphoprotein that can form complexes with host proteins such as large-T antigen and E1B. The protein is found in normal tissues and cells, but at concentrations which are minute by comparison with transformed cells or tumor tissue.

Missense mutations are common for the p53 gene and are essential for the transforming ability of the oncogene. A single genetic change prompted by point mutations can create carcinogenic p53. Unlike other oncogenes, however, p53 point mutations are known to occur in at least 30 distinct codons, often creating dominant alleles that produce shifts in cell phenotype without a reduction to homozygosity. Additionally, many of these dominant negative alleles appear to be tolerated in the organism and passed on in the germ line. Various mutant alleles appear to range from minimally dysfunctional to strongly penetrant, dominant negative alleles (Weinberg, 1991). High levels of mutant p53 have been found in many cells transformed by chemical carcinogenesis, ultraviolet radiation, and several viruses.

In some aspects, a p53 biomarker is employed to select patients for p53 treatment. In particular aspects, a favorable tumor p53 biomarker profile is defined by either wild-type p53 gene configuration or <20% p53-positive cells by immunohistochemistry (U.S. Pat. No. 9,746,471 and Nemunaitis et al., 2009; both incorporated by reference in their entirety).

2. MDA-7

The combination therapies provided herein can also additionally comprise MDA-7 gene therapy comprising administering a full-length or truncated MDA-7 gene. The protein product of the mda-7 gene, Interleukin (IL)-24 is a cytokine that belongs to the IL-10 family of cytokines and is also a tumor suppressor. The cDNA encoding the MDA-7 protein has been described by Jiang et al., 1995 (WO1995011986). The MDA-7 cDNA encodes an evolutionarily conserved protein of 206 amino acids with a predicted size of 23.8 kDa.

The nucleic acid encoding MDA-7 provided herein can encode a full-length or truncated human IL-24 protein or polypeptide. A truncated version of MDA-7 would comprise a portion or portions of contiguous amino acid regions of the full-length sequence, but would not contain the entire sequence. The truncated version may be truncated by any number of contiguous amino acids at any site in the polypeptide. For example, truncated versions of MDA-7 could encode amino acids from about 49 to about 206; about 75 to about 206; about 100 to about 206; about 125 to about 206; about 150 to about 206; about 175 to about 206; or about 182 to about 206 of human wild-type MDA-7. It is also contemplated that MDA-7 polypeptides containing at least about 85%, 90%, and 95% of human wild-type MDA-7 are within the scope of the invention.

B. Extracellular Matrix Degradation

Methods of enhancing the anti-tumor effect of the chimeric adenoviral construct are also provided herein. In one aspect, the delivery of the gene therapy (e.g., viral distribution) and tumor penetration are enhanced by a protein or agent which degrades the tumor cell extracellular matrix (ECM) or component thereof.

The extracellular matrix (ECM) is a collection of extracellular molecules secreted by cells that provides structural and biochemical support to the surrounding cells. Because multicellularity evolved independently in different multicellular lineages, the composition of ECM varies between multicellular structures; however, cell adhesion, cell-to-cell communication and differentiation are common functions of the ECM. Components of the ECM that may be targeted by the extracellular matrix degradative protein include collagen, elastin, hyaluronic acid, fibronectin and laminin.

1. Relaxin

One extracellular matrix degrading protein that can be used in the methods provided herein is relaxin. Relaxin is a 6 kDa peptide hormone that is structurally related to insulin and insulin-like growth factors. It is predominantly produced in the corpus luteum and endometrium and its serum level greatly increases during pregnancy (Sherwood et al., 1984). Relaxin is a potent inhibitor of collagen expression when collagen is overexpressed, but it does not markedly alter basal levels of collagen expression, in contrast to other collagen. It promotes the expression of various MMPs such as MMP2, MMP3, and MMP9 to degrade collagen, so that connective tissues and basal membranes are degraded to lead to the disruption of extracellular matrix of birth canal. In addition to this, the promotion of MMP 1 and MMP 3 expressions by relaxin is also observed in lung, heart, skin, intestines, mammary gland, blood vessel and spermiduct where relaxin plays a role as an inhibitor to prevent over-expression of collagen (Qin, X., et al., 1997a; Qin, X., et al., 1997b).

Administration of the relaxin protein or nucleic acid encoding the relaxin protein can induce the degradation of collagen, a major component of the extracellular matrix surrounding tumor cells, to disrupt connective tissue and basal membrane, thereby resulting in the degradation of extracellular matrix. In particular, when administered to tumor tissues enclosed tightly by connective tissue, the administration of the tumor suppressor gene therapy in combination with relaxin exhibits improved anti-tumor efficacy.

The relaxin protein can be full length relaxin or a portion of the relaxin molecule that retains biological activity as described in U.S. Pat. No. 5,023,321. Particularly, the relaxin is recombinant human relaxin (H2) or other active agents with relaxin-like activity, such as agents that competitively displace bound relaxin from a receptor. Relaxin can be made by any method known to those skilled in the art, preferably as described in U.S. Pat. No. 4,835,251. Relaxin analogs or derivatives thereof are described in U.S. Pat. No. 5,811,395 and peptide synthesis is described in U.S. Patent Publication No. US20110039778.

An exemplary adenoviral relaxin that may be used in the methods provided herein is described by Kim et al. (2006). Briefly, a relaxin-expressing, replication-competent (Ad-ΔE1B-RLX) adenovirus is generated by inserting a relaxin gene into the E3 adenoviral region.

2. Hyaluronidase

In some embodiments, any substance which is able to hydrolyze the polysaccharides which are generally present in extracellular matrices such as hyaluronic acid can be administered. Particularly, the extracellular matrix degrading protein used in the present invention can be hyaluronidase. Hyaluronan (or hyaluronic acid) is a ubiquitous constituent of the vertebrate extracellular matrix. This linear polysaccharide, which is based on glucuronic acid and glucosamine [D-glucuronic acid 1β-3)N-acetyl-D-glucosamine(1-b-4)], is able to exert an influence on the physicochemical characteristics of the matrices by means of its property of forming very viscous solutions. Hyaluronic acid also interacts with various receptors and binding proteins which are located on the surface of the cells. It is involved in a large number of biological processes such as fertilization, embryonic development, cell migration and differentiation, wound-healing, inflammation, tumor growth and the formation of metastases.

Hyaluronic acid is hydrolyzed by hyaluronidase and its hydrolysis leads to disorganization of the extracellular matrix. Thus, it is contemplated that any substance possessing hyaluronidase activity is suitable for use in the present methods such as hyaluronidases as described in Kreil (Protein Sci., 1995, 4:1666-1669). The hyaluronidase can be a hyaluronidase which is derived from a mammalian, reptilian or hymenopteran hyaluronate glycanohydrolase, from a hyaluronate glycanohydrolase from the salivary gland of the leech, or from a bacterial, in particular streptococcal, pneumococcal and clostridial hyaluronate lyase. The enzymatic activity of the hyaluronidase can be assessed by conventional techniques such as those described in Hynes and Ferretti (Methods Enzymol., 1994, 235: 606-616) or Bailey and Levine (J. Pharm. Biomed. Anal., 1993, 11: 285-292).

3. C. Decorin

Decorin, a small leucine-rich proteoglycan, is a ubiquitous component of the extracellular matrix and is preferentially found in association with collagen fibrils. Decorin binds to collagen fibrils and delays the lateral assembly of individual triple helical collagen molecules, resulting in the decreased diameter of the fibrils. In addition, decorin can modulate the interactions of extracellular matrix components, such as fibronectin and thrombospondin, with cells. Furthermore, decorin is capable of affecting extracellular matrix remodeling by induction of the matrix metalloproteinase collagenase. These observations suggest that decorin regulates the production and assembly of the extracellular matrix at several levels, and hence has a prominent role in remodeling connective tissues as described by Choi et al. (Gene Therapy, 17: 190-201, 2010) and by Xu et al. (Gene Therapy, 22(3): 31-40, 2015).

An exemplary adenoviral decorin that may be used in the methods provided herein is described by Choi et al. (Gene Therapy, 17: 190-201, 2010). Briefly, a decorin-expressing, replication-competent (Ad-ΔE1B-DCNG) adenovirus is generated by inserting a decorin gene into the E3 adenoviral region. Another exemplary adenoviral decorin that may be used in the methods provided herein is described by Xu et al. (Gene Therapy, 22(3): 31-40, 2015). Similarly, a decorin-expressing, replication-competent (Ad.dcn) adenovirus is generated by inserting a decorin gene into the E3 adenoviral region.

C. Delivery of Nucleic Acids

A nucleic acid may be made by any technique known to one of ordinary skill in the art. Non-limiting examples of a synthetic nucleic acid, particularly a synthetic oligonucleotide, include a nucleic acid made by in vitro chemical synthesis using phosphotriester, phosphite or phosphoramidite chemistry and solid phase techniques such as described in EP 266,032, or via deoxynucleoside H-phosphonate intermediates as described by Froehler et al., 1986, and U.S. Pat. No. 5,705,629. A non-limiting example of enzymatically produced nucleic acid includes one produced by enzymes in amplification reactions such as PCR™ (see for example, U.S. Pat. Nos. 4,683,202 and 4,682,195), or the synthesis of oligonucleotides described in U.S. Pat. No. 5,645,897. A non-limiting example of a biologically produced nucleic acid includes recombinant nucleic acid production in living cells, such as recombinant DNA vector production in bacteria (see for example, Sambrook et al. 1989).

The nucleic acid(s), regardless of the length of the sequence itself, may be combined with other nucleic acid sequences, including but not limited to, promoters, enhancers, polyadenylation signals, restriction enzyme sites, multiple cloning sites, coding segments, and the like, to create one or more nucleic acid construct(s). The overall length may vary considerably between nucleic acid constructs. Thus, a nucleic acid segment of almost any length may be employed, with the total length preferably being limited by the ease of preparation or use in the intended recombinant nucleic acid protocol.

1. Nucleic Acid Delivery by Expression Vector

Vectors provided herein are designed, primarily, to express a therapeutic nucleic acid such as a therapeutic tumor suppressor gene (e.g., p53 and/or MDA-7) and/or extracellular matrix degradative gene (e.g., relaxin) under the control of regulated eukaryotic promoters (i.e., constitutive, inducible, repressable, tissue-specific). In some aspects, p53 and MDA-7 may be co-expressed in a vector. In another aspect, the p53 and/or MDA-7 may be co-expressed with an extracellular matrix degradative gene. Also, the vectors may contain a selectable marker if, for no other reason, to facilitate their manipulation in vitro.

One of skill in the art would be well-equipped to construct a vector through standard recombinant techniques (see, for example, Sambrook et al., 2001 and Ausubel et al., 1996, both incorporated herein by reference). Vectors include but are not limited to, plasmids, cosmids, viruses (bacteriophage, animal viruses, and plant viruses), and artificial chromosomes (e.g., YACs), such as retroviral vectors (e.g. derived from Moloney murine leukemia virus vectors (MoMLV), MSCV, SFFV, MPSV, SNV etc), lentiviral vectors (e.g. derived from HIV-1, HIV-2, SIV, BIV, FIV etc.), adenoviral (Ad) vectors including replication competent, replication deficient and gutless forms thereof, adeno-associated viral (AAV) vectors, simian virus 40 (SV-40) vectors, bovine papilloma virus vectors, Epstein-Barr virus vectors, herpes virus vectors, vaccinia virus vectors, Harvey murine sarcoma virus vectors, murine mammary tumor virus vectors, Rous sarcoma virus vectors.

1. Viral Vectors

Viral vectors encoding the tumor suppressor and/or extracellular matrix degradative gene may be provided in certain aspects of the present invention. In generating recombinant viral vectors, non-essential genes are typically replaced with a gene or coding sequence for a heterologous (or non-native) protein. A viral vector is a kind of expression construct that utilizes viral sequences to introduce nucleic acid and possibly proteins into a cell. The ability of certain viruses to infect cells or enter cells via receptor-mediated endocytosis, and to integrate into host cell genomes and express viral genes stably and efficiently have made them attractive candidates for the transfer of foreign nucleic acids into cells (e.g., mammalian cells). Non-limiting examples of virus vectors that may be used to deliver a nucleic acid of certain aspects of the present invention are described below.

Lentiviruses are complex retroviruses, which, in addition to the common retroviral genes gag, pol, and env, contain other genes with regulatory or structural function. Lentiviral vectors are well known in the art (see, for example, Naldini et al., 1996; Zufferey et al., 1997; Blomer et al., 1997; U.S. Pat. Nos. 6,013,516 and 5,994,136).

Recombinant lentiviral vectors are capable of infecting non-dividing cells and can be used for both in vivo and ex vivo gene transfer and expression of nucleic acid sequences. For example, recombinant lentivirus capable of infecting a non-dividing cell—wherein a suitable host cell is transfected with two or more vectors carrying the packaging functions, namely gag, pol and env, as well as rev and tat—is described in U.S. Pat. No. 5,994,136, incorporated herein by reference.

a. Adenoviral Vector

The nucleic acids may be encoded by an adenoviral vector as described above.

b. Retroviral Vector

Additionally, the tumor suppressor and/or extracellular matrix degradative gene may be encoded by a retroviral vector. The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Concern with the use of defective retrovirus vectors is the potential appearance of wild-type replication-competent virus in the packaging cells. This can result from recombination events in which the intact sequence from the recombinant virus inserts upstream from the gag, pol, env sequence integrated in the host cell genome. However, packaging cell lines are available that should greatly decrease the likelihood of recombination (Markowitz et al., 1988; Hersdorffer et al., 1990).

c. Adeno-Associated Viral Vector

Adeno-associated virus (AAV) is an attractive vector system for use in the present disclosure as it has a high frequency of integration and it can infect nondividing cells, thus making it useful for delivery of genes into mammalian cells (Muzyczka, 1992). AAV has a broad host range for infectivity (Tratschin, et al., 1984; Laughlin, et al., 1986; Lebkowski, et al., 1988; McLaughlin, et al., 1988), which means it is applicable for use with the present invention. Details concerning the generation and use of rAAV vectors are described in U.S. Pat. Nos. 5,139,941 and 4,797,368.

AAV is a dependent parvovirus in that it requires coinfection with another virus (either adenovirus or a member of the herpes virus family) to undergo a productive infection in cultured cells (Muzyczka, 1992). In the absence of coinfection with helper virus, the wild-type AAV genome integrates through its ends into human chromosome 19 where it resides in a latent state as a provirus (Kotin et al., 1990; Samulski et al., 1991). rAAV, however, is not restricted to chromosome 19 for integration unless the AAV Rep protein is also expressed (Shelling and Smith, 1994). When a cell carrying an AAV provirus is superinfected with a helper virus, the AAV genome is "rescued" from the chromosome or from a recombinant plasmid, and a normal productive infection is established (Samulski et al., 1989; McLaughlin et al., 1988; Kotin et al., 1990; Muzyczka, 1992).

Typically, recombinant AAV (rAAV) virus is made by cotransfecting a plasmid containing the gene of interest flanked by the two AAV terminal repeats (McLaughlin et al., 1988; Samulski et al., 1989; each incorporated herein by reference) and an expression plasmid containing the wild-type AAV coding sequences without the terminal repeats, for example pIM45 (McCarty et al., 1991). The cells are also infected or transfected with adenovirus or plasmids carrying the adenovirus genes required for AAV helper function. rAAV virus stocks made in such fashion are contaminated with adenovirus which must be physically separated from the rAAV particles (for example, by cesium chloride density centrifugation). Alternatively, adenovirus vectors containing the AAV coding regions or cell lines containing the AAV coding regions and some or all of the adenovirus helper genes could be used (Yang et al., 1994; Clark et al., 1995). Cell lines carrying the rAAV DNA as an integrated provirus can also be used (Flotte et al., 1995).

d. Other Viral Vectors

Other viral vectors may be employed as constructs in the present disclosure. Vectors derived from viruses such as vaccinia virus (Ridgeway, 1988; Baichwal and Sugden, 1986; Coupar et al., 1988) and herpesviruses may be employed. They offer several attractive features for various mammalian cells (Friedmann, 1989; Ridgeway, 1988; Baichwal and Sugden, 1986; Coupar et al., 1988; Horwich et al., 1990).

A molecularly cloned strain of Venezuelan equine encephalitis (VEE) virus has been genetically refined as a replication competent vaccine vector for the expression of heterologous viral proteins (Davis et al., 1996). Studies have demonstrated that VEE infection stimulates potent CTL responses and has been suggested that VEE may be an extremely useful vector for immunizations (Caley et al., 1997).

In further embodiments, the nucleic acid encoding chimeric CD154 is housed within an infective virus that has been engineered to express a specific binding ligand. The virus particle will thus bind specifically to the cognate receptors of the target cell and deliver the contents to the cell. A novel approach designed to allow specific targeting of retrovirus vectors was recently developed based on the chemical modification of a retrovirus by the chemical addition of lactose residues to the viral envelope. This modification can permit the specific infection of hepatocytes via sialoglycoprotein receptors.

For example, targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

2. Regulatory Elements

Expression cassettes included in vectors useful in the present disclosure in particular contain (in a 5'-to-3' direction) a eukaryotic transcriptional promoter operably linked to a protein-coding sequence, splice signals including intervening sequences, and a transcriptional termination/polyadenylation sequence. The promoters and enhancers that control the transcription of protein encoding genes in eukaryotic cells are composed of multiple genetic elements. The cellular machinery is able to gather and integrate the regulatory information conveyed by each element, allowing different genes to evolve distinct, often complex patterns of transcriptional regulation. A promoter used in the context of the present invention includes constitutive, inducible, and tissue-specific promoters.

a. Promoter/Enhancers

The expression constructs provided herein comprise a promoter to drive expression of the tumor suppressor and/or extracellular matrix degradative gene. A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30-110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β-lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated that the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al. 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally, any promoter/enhancer combination (as per, for example, the Eukaryotic Promoter Data Base EPDB, through world wide web at epd.isb-sib.ch/) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

Non-limiting examples of promoters include early or late viral promoters, such as, SV40 early or late promoters, cytomegalovirus (CMV) immediate early promoters, Rous Sarcoma Virus (RSV) early promoters; eukaryotic cell promoters, such as, e. g., beta actin promoter (Ng, 1989; Quitsche et al., 1989), GADPH promoter (Alexander et al., 1988, Ercolani et al., 1988), metallothionein promoter (Karin et al., 1989; Richards et al., 1984); and concatenated response element promoters, such as cyclic AMP response element promoters (cre), serum response element promoter (sre), phorbol ester promoter (TPA) and response element promoters (tre) near a minimal TATA box. It is also possible to use human growth hormone promoter sequences (e.g., the human growth hormone minimal promoter described at Genbank, accession no. X05244, nucleotide 283-341) or a mouse mammary tumor promoter (available from the ATCC, Cat. No. ATCC 45007). In certain embodiments, the promoter is CMV IE, dectin-1, dectin-2, human CD11c, F4/80, SM22, RSV, SV40, Ad MLP, beta-actin, MHC class I or MHC class II promoter, however any other promoter that is useful to drive expression of the p53, MDA-7 and/or the relaxin gene is applicable to the practice of the present invention.

In certain aspects, methods of the disclosure also concern enhancer sequences, i.e., nucleic acid sequences that increase a promoter's activity and that have the potential to act in cis, and regardless of their orientation, even over relatively long distances (up to several kilobases away from the target promoter). However, enhancer function is not necessarily restricted to such long distances as they may also function in close proximity to a given promoter.

b. Initiation Signals and Linked Expression

A specific initiation signal also may be used in the expression constructs provided in the present disclosure for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

Additionally, certain 2A sequence elements could be used to create linked- or co-expression of genes in the constructs provided in the present disclosure. For example, cleavage sequences could be used to co-express genes by linking open reading frames to form a single cistron. An exemplary cleavage sequence is the F2A (Foot-and-mouth diease virus 2A) or a "2A-like" sequence (e.g., Thosea asigna virus 2A; T2A) (Minskaia and Ryan, 2013).

c. Origins of Replication

In order to propagate a vector in a host cell, it may contain one or more origins of replication sites (often termed "ori"), for example, a nucleic acid sequence corresponding to oriP of EBV as described above or a genetically engineered oriP with a similar or elevated function in programming, which is a specific nucleic acid sequence at which replication is initiated. Alternatively a replication origin of other extra-chromosomally replicating virus as described above or an autonomously replicating sequence (ARS) can be employed.

3. Selection and Screenable Markers

In some embodiments, cells containing a construct of the present disclosure may be identified in vitro or in vivo by including a marker in the expression vector. Such markers would confer an identifiable change to the cell permitting easy identification of cells containing the expression vector. Generally, a selection marker is one that confers a property that allows for selection. A positive selection marker is one in which the presence of the marker allows for its selection, while a negative selection marker is one in which its presence prevents its selection. An example of a positive selection marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selection markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes as negative selection markers such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selection and screenable markers are well known to one of skill in the art.

D. Other Methods of Nucleic Acid Delivery

In addition to viral delivery of the nucleic acids encoding the tumor suppressor(s) and/or extracellular matrix degradative gene, the following are additional methods of recombinant gene delivery to a given host cell and are thus considered in the present disclosure.

Introduction of a nucleic acid, such as DNA or RNA, may use any suitable methods for nucleic acid delivery for transformation of a cell, as described herein or as would be known to one of ordinary skill in the art. Such methods include, but are not limited to, direct delivery of DNA such as by ex vivo transfection (Wilson et al., 1989, Nabel et al, 1989), by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference; Tur-Kaspa et al., 1986; Potter et al., 1984); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991) and receptor-mediated transfection (Wu and Wu, 1987; Wu and Wu, 1988); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by *Agrobacterium*-mediated transformation (U.S. Pat. Nos. 5,591,616 and 5,563,055, each incorporated herein by reference); by desiccation/inhibition-mediated DNA uptake (Potrykus et al., 1985), and any combination of such methods. Through the application of techniques such as these, organelle(s), cell(s), tissue(s) or organism(s) may be stably or transiently transformed.

1. Electroporation

In certain particular embodiments of the present disclosure, the gene construct is introduced into target hyperproliferative cells via electroporation. Electroporation involves the exposure of cells (or tissues) and DNA (or a DNA complex) to a high-voltage electric discharge.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

It is contemplated that electroporation conditions for hyperproliferative cells from different sources may be optimized. One may particularly wish to optimize such parameters as the voltage, the capacitance, the time and the electroporation media composition. The execution of other routine adjustments will be known to those of skill in the art. See e.g., Hoffman, 1999; Heller et al., 1996.

2. Lipid-Mediated Transformation

In a further embodiment, the tumor suppressor and/or extracellular matrix degradative gene may be entrapped in a liposome or lipid formulation. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is a gene construct complexed with Lipofectamine (Gibco BRL).

Lipid-mediated nucleic acid delivery and expression of foreign DNA in vitro has been very successful (Nicolau and Sene, 1982; Fraley et al., 1979; Nicolau et al., 1987). Wong et al. (1980) demonstrated the feasibility of lipid-mediated delivery and expression of foreign DNA in cultured chick embryo, HeLa and hepatoma cells.

Lipid based non-viral formulations provide an alternative to adenoviral gene therapies. Although many cell culture studies have documented lipid based non-viral gene transfer, systemic gene delivery via lipid based formulations has been limited. A major limitation of non-viral lipid based gene delivery is the toxicity of the cationic lipids that comprise the non-viral delivery vehicle. The in vivo toxicity of liposomes partially explains the discrepancy between in vitro and in vivo gene transfer results. Another factor contributing to this contradictory data is the difference in lipid vehicle stability in the presence and absence of serum proteins. The interaction between lipid vehicles and serum proteins has a dramatic impact on the stability characteristics of lipid vehicles (Yang and Huang, 1997). Cationic lipids attract and bind negatively charged serum proteins. Lipid vehicles associated with serum proteins are either dissolved or taken up by macrophages leading to their removal from circulation. Current in vivo lipid delivery methods use subcutaneous, intradermal, intratumoral, or intracranial injection to avoid the toxicity and stability problems associated with cationic lipids in the circulation. The interaction of lipid vehicles and plasma proteins is responsible for the disparity between the efficiency of in vitro (Feigner et al., 1987) and in vivo gene transfer (Zhu el al., 1993; Philip et al., 1993; Solodin et al., 1995; Liu et al., 1995; Thierry et al., 1995; Tsukamoto et al., 1995; Aksentijevich et al., 1996).

Advances in lipid formulations have improved the efficiency of gene transfer in vivo (Templeton et al. 1997; WO 98/07408). A novel lipid formulation composed of an equimolar ratio of 1,2-bis(oleoyloxy)-3-(trimethyl ammonio) propane (DOTAP) and cholesterol significantly enhances systemic in vivo gene transfer, approximately 150 fold. The DOTAP:cholesterol lipid formulation forms unique structure termed a "sandwich liposome". This formulation is reported to "sandwich" DNA between an invaginated bilayer or 'vase' structure. Beneficial characteristics of these lipid structures include a positive ρ, colloidal stabilization by cholesterol, two dimensional DNA packing and increased serum stability. Patent Application Nos. 60/135,818 and 60/133,116 discuss formulations that may be used with the present invention.

The production of lipid formulations often is accomplished by sonication or serial extrusion of liposomal mixtures after (I) reverse phase evaporation (II) dehydration-rehydration (III) detergent dialysis and (IV) thin film hydration. Once manufactured, lipid structures can be used to encapsulate compounds that are toxic (chemotherapeutics) or labile (nucleic acids) when in circulation. Lipid encapsulation has resulted in a lower toxicity and a longer serum half-life for such compounds (Gabizon et al., 1990). Numerous disease treatments are using lipid based gene transfer strategies to enhance conventional or establish novel therapies, in particular therapies for treating hyperproliferative diseases.

IV. PREFERENTIAL CD123/CD132 AGONISTS

In certain aspects, the subject is administered at least one CD122/CD132 agonist, such as a CD122/CD132 agonist that preferentially binds to the CD122/CD132 receptor complex and has lower affinity binding for CD25 or the IL15α receptor. The CD122/CD132 may be selected from a genetically engineered IL-22 mutein that has a modified amino acid sequence compared to wild type IL2 (US 2017/0044229; incorporated by reference in its entirety). In certain aspects, the preferential CD122/CD132 agonist is an IL-2/anti-IL-2 monoclonal antibody immune complex (US20170183403A1; incorporated by reference in its entirety), or a genetically engineered IL-2 mutein that has a modified amino acid sequence compared to wild type IL-2 combined with an anti-IL2 monoclonal antibody immune complex (WO2014100014A1; incorporated by reference in its entirety), a PEGylated form of IL2 like NKTR-214 (Charych et al., 2016), an IL15/anti-IL15 monoclonal antibody immune complex, an IL15/IL15 Receptor α-IgG1-Fc (IL15/IL15Rα-IgG1-Fc) immune complex (US20060257361A1, EP2724728A1 and Dubois et al., 2008), a genetically engineered IL-15 mutein that has a modified amino acid sequence compared to wild type IL-15 combined with an IL15Rα-IgG1-Fc immune complex (US20070160578; incorporated herein in its entirety), or a PEGylated form of IL15 with preferential binding to CD122/CD132. In some embodiments, more than one CD122/CD132 agonist are utilized.

V. ONCOLYTIC VIRUSES

In some aspects, the present disclosure comprises administration of at least one oncolytic virus. In some aspects, the oncolytic virus is engineered to express p53, MDA-7, IL-12, TGF-β inhibitor, and/or IL-10 inhibitor. In certain aspects, the oncolytic virus is a single- or double-stranded DNA virus, RNA virus, adenovirus, adeno-associated virus, retrovirus, lentivirus, herpes virus, pox virus, vaccinia virus, vesicular stomatitis virus, polio virus, Newcastle's Disease virus, Epstein-Barr virus, influenza virus, reoviruses, myxoma virus, maraba virus, rhabdovirus, enadenotucirev or coxsackie virus. In some aspects, the oncolytic virus is engineered to express a cytokine, such as granulocyte-macrophage colony-stimulating factor (GM-CSF) or IL-12. In some aspects, the oncolytic virus is further defined as talimogene laherparepvec (T-VEC). In some aspects, the oncolytic adenoviral vector is derived from a modified TERT Promoter Oncolytic Adenovirus (U.S. Pat. No. 8,067,567; incorporated herein by reference in its entirety) and/or the HRE-E2F-TERT Hybrid Promoter Oncolytic Adenovirus (PCT/KR2011/004693; incorporated herein by reference in its entirety) and/or an adenovirus with a modified E1a regulatory sequence wherein at least one Pea3 binding site, or a functional portion thereof, is deleted with an Elb-19K clone insertion site (EP2403951A2; incorporated herein by reference in its entirety) which may all be modified to express therapeutic genes. In some aspects, the oncolytic adenoviral vector is derived from E1b deleted oncolytic adenoviruses (Yu and Fang, 2007; Li, 2009; both incorporated by reference in their entirety).

Exemplary oncolytic viruses include, but are not limited to, Ad5-yCD/mutTKSR39rep-hIL12, Cavatak™, CG0070, DNX-2401, G207, HF10, IMLYGIC™, JX-594, MG1-MA3, MV-NIS, OBP-301, Reolysin®, Toca 511, Oncorine, RIGVIR, an adenovirus overexpressing the adenoviral death protein (ADP) as described in U.S. Pat. No. 7,589,069 B1; incorporated by reference in its entirety, such as VirRx007, an N1L deleted vaccinia virus expressing IL12 as described in PCT/GB2015/051023; incorporated by reference in its entirety. Other exemplary oncolytic viruses are described, for example, in International Patent Publication Nos. WO2015/027163, WO2014/138314, WO2014/047350, and WO2016/009017; all incorporated herein by reference.

In a particular aspects, the oncolytic viral agent is talimogene laherparepvec (T-VEC) which is an oncolytic herpes simplex virus genetically engineered to express GM-C SF. Talimogene laherparepvec, HSV-1 [strain JS1] ICP34.5-/ICP47-/hGM-CSF, (previously known as OncoVEX$^{GM\ CSF}$), is an intratumorally delivered oncolytic immunotherapy comprising an immune-enhanced HSV-1 that selectively replicates in solid tumors. (Lui et al., 2003; U.S. Pat. Nos. 7,223,593 and 7,537,924; incorporated herein by reference). In October 2015, the US FDA approved T-VEC, under the brand name IMLYGIC™, for the treatment of melanoma in patients with inoperable tumors. The characteristics and methods of administration of T-VEC are described in, for example, the IMLYGIC™ package insert (Amgen, 2015) and U.S. Patent Publication No. US2015/0202290; both incorporated herein by reference. For example, talimogene laherparepvec is typically administered by intratumoral injection into injectable cutaneous, subcutaneous, and nodal tumors at a dose of up to 4.0 ml of $10^6$ plaque forming unit/mL (PFU/mL) at day 1 of week 1 followed by a dose of up to 4.0 ml of $10^8$ PFU/mL at day 1 of week 4, and every 2 weeks (±3 days) thereafter. The recommended volume of talimogene laherparepvec to be injected into the tumor(s) is dependent on the size of the tumor(s) and should be determined according to the injection volume guideline. While T-VEC has demonstrated clinical activity in melanoma patients, many cancer patients either do not respond or cease responding to T-VEC treatment. In one embodiment, the p53 and/or MDA-7 nucleic acids and the at least one CD122/CD132 agonist may be administered after, during or before T-VEC therapy, such as to reverse treatment resistance.

In some embodiments, E1b deleted oncolytic adenoviruses are combined with at least one preferential CD122/CD132 agonist and at least one immune checkpoint inhibitor. Exemplary E1b deleted oncolytic adenoviruses are H101 (Oncorine), Onyx 015 or H103 which expresses the heat shock protein 70 (HSP70) or the oncolytic adenovirus H102 in which expression of the Ad E1a gene is driven by the alpha-fetoprotein (AFP) promoter resulting in preferential replication in hepatocellular carcinoma and other AFP overexpressing cancers compared to normal cells (Yu and Fang, 2007; Li, 2009; both incorporated by reference in their entirety).

VI. IMMUNE CHECKPOINT INHIBITORS

In certain embodiments, the present disclosure provides methods of combining the blockade of immune checkpoints with the chimeric adenoviral vector. The therapy may further comprise tumor suppressor gene therapy, such as p53 and/or MDA-7 gene therapy. Immune checkpoints are molecules in the immune system that either turn up a signal (e.g., co-stimulatory molecules) or turn down a signal. Inhibitory checkpoint molecules that may be targeted by immune checkpoint blockade include adenosine A2A receptor (A2AR), B7-H3 (also known as CD276), B and T lymphocyte attenuator (BTLA), cytotoxic T-lymphocyte-associated protein 4 (CTLA-4, also known as CD152), indoleamine 2,3-dioxygenase (IDO), killer-cell immunoglobulin (KIR), lymphocyte activation gene-3 (LAG3), programmed death 1 (PD-1), T-cell immunoglobulin domain and mucin domain 3 (TIM-3) and V-domain Ig suppressor of T cell activation (VISTA). In particular, the immune checkpoint inhibitors target the PD-1 axis and/or CTLA-4.

The immune checkpoint inhibitors may be drugs such as small molecules, recombinant forms of ligand or receptors, or, in particular, are antibodies, such as human antibodies (e.g., International Patent Publication WO2015016718; Pardoll, *Nat Rev Cancer,* 12(4): 252-64, 2012; both incorporated herein by reference). Known inhibitors of the immune checkpoint proteins or analogs thereof may be used, in particular chimerized, humanized or human forms of antibodies may be used. As the skilled person will know, alternative and/or equivalent names may be in use for certain antibodies mentioned in the present disclosure. Such alternative and/or equivalent names are interchangeable in the context of the present invention. For example it is known that lambrolizumab is also known under the alternative and equivalent names MK-3475 and pembrolizumab.

It is contemplated that any of the immune checkpoint inhibitors that are known in the art to stimulate immune responses may be used. This includes inhibitors that directly or indirectly stimulate or enhance antigen-specific T-lymphocytes. These immune checkpoint inhibitors include, without limitation, agents targeting immune checkpoint proteins and pathways involving PD-L2, LAG3, BTLA, B7H4 and TIM3. For example, LAG3 inhibitors known in the art include soluble LAG3 (IMP321, or LAG3-Ig disclosed in WO2009044273) as well as mouse or humanized antibodies blocking human LAG3 (e.g., IMP701 disclosed in WO2008132601), or fully human antibodies blocking human LAG3 (such as disclosed in EP 2320940). Another example is provided by the use of blocking agents towards BTLA, including without limitation antibodies blocking human BTLA interaction with its ligand (such as 4C7 disclosed in WO2011014438). Yet another example is provided by the use of agents neutralizing B7H4 including without limitation antibodies to human B7H4 (disclosed in WO 2013025779, and in WO2013067492) or soluble recombinant forms of B7H4 (such as disclosed in US20120177645). Yet another example is provided by agents neutralizing B7-H3, including without limitation antibodies neutralizing human B7-H3 (e.g. MGA271 disclosed as BRCA84D and derivatives in US 20120294796). Yet another example is provided by agents targeting TIM3, including without limitation antibodies targeting human TIM3 (e.g. as disclosed in WO 2013006490 A2 or the anti-human TIM3, blocking antibody F38-2E2 disclosed by Jones et al., J Exp Med. 2008; 205(12):2763-79).

In addition, more than one immune checkpoint inhibitor (e.g., anti-PD-1 antibody and anti-CTLA-4 antibody) may be used in combination with the tumor suppressor gene therapy. For example, p53 gene therapy and immune checkpoint inhibitors (e.g., anti-KIR antibody and/or anti-PD-1 antibody) can be administered to enhance innate anti-tumor immunity followed by IL24 gene therapy and immune checkpoint inhibitors (e.g., anti-PD-1 antibody) to induce adaptive anti-tumor immune responses.

A. PD-1 Axis Antagonists

T cell dysfunction or anergy occurs concurrently with an induced and sustained expression of the inhibitory receptor, programmed death 1 polypeptide (PD-1). Thus, therapeutic targeting of PD-1 and other molecules which signal through interactions with PD-1, such as programmed death ligand 1 (PD-L1) and programmed death ligand 2 (PD-L2) is provided herein. PD-L1 is overexpressed in many cancers and is often associated with poor prognosis (Okazaki T et al., Intern. Immun. 2007 19(7):813). Thus, inhibition of the PD-L1/PD-1 interaction in combination with p53 and/or MDA-7 gene therapy is provided herein such as to enhance $CD8^+$ T cell-mediated killing of tumors.

Provided herein is a method for treating or delaying progression of cancer in an individual comprising administering to the individual an effective amount of a PD-1 axis binding antagonist in combination with p53 and/or MDA-7 gene therapy. Also provided herein is a method of enhancing immune function in an individual in need thereof comprising administering to the individual an effective amount of a PD-1 axis binding antagonist and p53 and/or MDA-7 gene therapy.

For example, a PD-1 axis binding antagonist includes a PD-1 binding antagonist, a PDL1 binding antagonist and a PDL2 binding antagonist. Alternative names for "PD-1" include CD279 and SLEB2. Alternative names for "PDL1"

include B7-H1, B7-4, CD274, and B7-H. Alternative names for "PDL2" include B7-DC, Btdc, and CD273. In some embodiments, PD-1, PDL1, and PDL2 are human PD-1, PDL1 and PDL2.

In some embodiments, the PD-1 binding antagonist is a molecule that inhibits the binding of PD-1 to its ligand binding partners. In a specific aspect, the PD-1 ligand binding partners are PDL1 and/or PDL2. In another embodiment, a PDL1 binding antagonist is a molecule that inhibits the binding of PDL1 to its binding partners. In a specific aspect, PDL1 binding partners are PD-1 and/or B7-1. In another embodiment, the PDL2 binding antagonist is a molecule that inhibits the binding of PDL2 to its binding partners. In a specific aspect, a PDL2 binding partner is PD-1. The antagonist may be an antibody, an antigen binding fragment thereof, an immunoadhesion, a fusion protein, or oligopeptide. Exemplary antibodies are described in U.S. Pat. Nos. 8,735,553, 8,354,509, and 8,008,449, all incorporated herein by reference. Other PD-1 axis antagonists for use in the methods provided herein are known in the art such as described in U.S. Patent Application No. US20140294898, US2014022021, and US20110008369, all incorporated herein by reference.

In some embodiments, the PD-1 binding antagonist is an anti-PD-1 antibody (e.g., a human antibody, a humanized antibody, or a chimeric antibody). In some embodiments, the anti-PD-1 antibody is selected from the group consisting of nivolumab, pembrolizumab, and CT-011. In some embodiments, the PD-1 binding antagonist is an immunoadhesin (e.g., an immunoadhesin comprising an extracellular or PD-1 binding portion of PDL1 or PDL2 fused to a constant region (e.g., an Fc region of an immunoglobulin sequence). In some embodiments, the PD-1 binding antagonist is AMP-224. Nivolumab, also known as MDX-1106-04, MDX-1106, ONO-4538, BMS-936558, and OPDIVO®, is an anti-PD-1 antibody described in WO2006/121168. Pembrolizumab, also known as MK-3475, Merck 3475, lambrolizumab, KEYTRUDA®, and SCH-900475, is an anti-PD-1 antibody described in WO2009/114335. CT-011, also known as hBAT or hBAT-1, is an anti-PD-1 antibody described in WO2009/101611. AMP-224, also known as B7-DCIg, is a PDL2-Fc fusion soluble receptor described in WO2010/027827 and WO2011/066342. Additional PD-1 binding antagonists include Pidilizumab, also known as CT-011, MEDI0680, also known as AMP-514, and REGN2810.

In some aspects, the immune checkpoint inhibitor is a PD-L1 antagonist such as Durvalumab, also known as MEDI4736, atezolizumab, also known as MPDL3280A, or avelumab, also known as MSB00010118C. In certain aspects, the immune checkpoint inhibitor is a PD-L2 antagonist such as rHIgM12B7. In some aspects, the immune checkpoint inhibitor is a LAG-3 antagonist such as, but not limited to, IMP321, and BMS-986016. The immune checkpoint inhibitor may be an adenosine A2a receptor (A2aR) antagonist such as PBF-509.

In some aspects, the antibody described herein (such as an anti-PD-1 antibody, an anti-PDL1 antibody, or an anti-PDL2 antibody) further comprises a human or murine constant region. In a still further aspect, the human constant region is selected from the group consisting of IgGl, IgG2, IgG2, IgG3, IgG4. In a still further specific aspect, the human constant region is IgGl. In a still further aspect, the murine constant region is selected from the group consisting of IgGl, IgG2A, IgG2B, IgG3. In a still further specific aspect, the antibody has reduced or minimal effector function. In a still further specific aspect, the minimal effector function results from production in prokaryotic cells. In a still further specific aspect the minimal effector function results from an "effector-less Fc mutation" or aglycosylation.

Accordingly, an antibody used herein can be aglycosylated. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxy amino acid, most commonly serine or threonine, although 5-hydroxyproline or 5-hydroxy lysine may also be used. Removal of glycosylation sites form an antibody is conveniently accomplished by altering the amino acid sequence such that one of the above-described tripeptide sequences (for N-linked glycosylation sites) is removed. The alteration may be made by substitution of an asparagine, serine or threonine residue within the glycosylation site another amino acid residue (e.g., glycine, alanine or a conservative substitution).

The antibody or antigen binding fragment thereof, may be made using methods known in the art, for example, by a process comprising culturing a host cell containing nucleic acid encoding any of the previously described anti-PDLl, anti-PD-1, or anti-PDL2 antibodies or antigen-binding fragment in a form suitable for expression, under conditions suitable to produce such antibody or fragment, and recovering the antibody or fragment.

B. CTLA-4

Another immune checkpoint that can be targeted in the methods provided herein is the cytotoxic T-lymphocyte-associated protein 4 (CTLA-4), also known as CD152. The complete cDNA sequence of human CTLA-4 has the Genbank accession number L15006. CTLA-4 is found on the surface of T cells and acts as an "off" switch when bound to CD80 or CD86 on the surface of antigen-presenting cells. CTLA4 is a member of the immunoglobulin superfamily that is expressed on the surface of Helper T cells and transmits an inhibitory signal to T cells. CTLA4 is similar to the T-cell co-stimulatory protein, CD28, and both molecules bind to CD80 and CD86, also called B7-1 and B7-2 respectively, on antigen-presenting cells. CTLA4 transmits an inhibitory signal to T cells, whereas CD28 transmits a stimulatory signal. Intracellular CTLA4 is also found in regulatory T cells and may be important to their function. T cell activation through the T cell receptor and CD28 leads to increased expression of CTLA-4, an inhibitory receptor for B7 molecules.

In some embodiments, the immune checkpoint inhibitor is an anti-CTLA-4 antibody (e.g., a human antibody, a humanized antibody, or a chimeric antibody), an antigen binding fragment thereof, an immunoadhesin, a fusion protein, or oligopeptide.

Anti-human-CTLA-4 antibodies (or VH and/or VL domains derived therefrom) suitable for use in the present methods can be generated using methods well known in the art. Alternatively, art recognized anti-CTLA-4 antibodies can be used. For example, the anti-CTLA-4 antibodies disclosed in: US 8,119,129, WO 01/14424, WO 98/42752; WO 00/37504 (CP675,206, also known as tremelimumab; formerly ticilimumab), U.S. Pat. No. 6,207,156; Hurwitz et al. (1998) Proc Natl Acad Sci USA 95(17): 10067-10071; Camacho et al. (2004) J Clin Oncology 22(145): Abstract No. 2505 (antibody CP-675206); and Mokyr et al. (1998) Cancer Res 58:5301-5304 can be used in the methods disclosed herein. The teachings of each of the aforementioned publications are hereby incorporated by reference. Antibodies that compete with any of these art-recognized antibodies for binding to CTLA-4 also can be used. For example, a humanized CTLA-4 antibody is described in International Patent Application No. WO2001014424, WO2000037504, and U.S. Pat. No. 8,017,114; all incorporated herein by reference.

An exemplary anti-CTLA-4 antibody is ipilimumab (also known as 10D1, MDX-010, MDX-101, and Yervoy®) or antigen binding fragments and variants thereof (see, e.g., WOO 1/14424). In other embodiments, the antibody comprises the heavy and light chain CDRs or VRs of ipilimumab. Accordingly, in one embodiment, the antibody comprises the CDR1, CDR2, and CDR3 domains of the VH region of ipilimumab, and the CDR1, CDR2 and CDR3 domains of the VL region of ipilimumab. In another embodiment, the antibody competes for binding with and/or binds to the same epitope on CTLA-4 as the above-mentioned antibodies. In another embodiment, the antibody has at least about 90% variable region amino acid sequence identity with the above-mentioned antibodies (e.g., at least about 90%, 95%, or 99% variable region identity with ipilimumab).

Other molecules for modulating CTLA-4 include CTLA-4 ligands and receptors such as described in U.S. Pat. Nos. 5,844,905, 5,885,796 and International Patent Application Nos. WO1995001994 and WO1998042752; all incorporated herein by reference, and immunoadhesions such as described in U.S. Pat. No. 8,329,867, incorporated herein by reference.

C. Killer Immunoglobulin-Like Receptor (KIR)

Another immune checkpoint inhibitor for use in the present invention is an anti-KIR antibody. Anti-human-KIR antibodies (or VH/VL domains derived therefrom) suitable for use in the invention can be generated using methods well known in the art.

Alternatively, art recognized anti-KIR antibodies can be used. The anti-KIR antibody can be cross-reactive with multiple inhibitory KIR receptors and potentiates the cytotoxicity of NK cells bearing one or more of these receptors. For example, the anti-KIR antibody may bind to each of KIR2D2DL1, KIR2DL2, and KIR2DL3, and potentiate NK cell activity by reducing, neutralizing and/or reversing inhibition of NK cell cytotoxicity mediated by any or all of these KIRs. In some aspects, the anti-KIR antibody does not bind KIR2DS4 and/or KIR2DS3. For example, monoclonal antibodies 1-7F9 (also known as IPH2101), 14F1, 1-6F1 and 1-6F5, described in WO 2006/003179, the teachings of which are hereby incorporated by reference, can be used. Antibodies that compete with any of these art-recognized antibodies for binding to KIR also can be used. Additional art-recognized anti-KIR antibodies which can be used include, for example, those disclosed in WO 2005/003168, WO 2005/009465, WO 2006/072625, WO 2006/072626, WO 2007/042573, WO 2008/084106, WO 2010/065939, WO 2012/071411 and WO/2012/160448.

An exemplary anti-KIR antibody is lirilumab (also referred to as BMS-986015 or IPH2102). In other embodiments, the anti-KIR antibody comprises the heavy and light chain complementarity determining regions (CDRs) or variable regions (VRs) of lirilumab. Accordingly, in one embodiment, the antibody comprises the CDR1, CDR2, and CDR3 domains of the heavy chain variable (VH) region of lirilumab, and the CDR1, CDR2 and CDR3 domains of the light chain variable (VL) region of lirilumab. In another embodiment, the antibody has at least about 90% variable region amino acid sequence identity with lirilumab.

VII. METHODS OF TREATMENT

Provided herein are methods for treating or delaying progression of cancer in an individual comprising administering to the individual an effective amount of a chimeric adenoviral vector with a LyP-1 targeting peptide. The vector may further comprise a soluble TGFβ decoy receptor.

In some embodiments, the treatment results in a sustained response in the individual after cessation of the treatment. The methods described herein may find use in treating conditions where enhanced immunogenicity is desired such as increasing tumor immunogenicity for the treatment of cancer. Also provided herein are methods of enhancing immune function such as in an individual having cancer comprising administering to the individual an effective amount of a CD122/CD132 agonist (e.g., IL-2/anti-IL-2 immune complex, IL-15/anti-IL-15 immune complex, an IL-15/IL-15 Receptor α-IgG1-Fc (IL-15/IL-15Rα-IgG1-Fc) immunocomplex, PEGylated IL-2, PEGylated IL-15, IL-2 muteins and/or IL-15 muteins) and p53 and/or MDA-7 gene therapy. In some embodiments, the individual is a human.

In some aspects, the subject is further administered a tumor suppressor immune gene therapy (see, PCT/US2016/060833, which is incorporated herein by reference in its entirety). In some aspects, the subject is further administered additional viral and non-viral gene therapies (PCT/US2017/065861; incorporated herein by reference in its entirety). In some aspects, the replication competent and/or replication incompetent viral and/or non-viral gene therapy may deliver one or more therapeutic genes which could be tumor suppressor genes or immune stimulatory genes.

Examples of cancers contemplated for treatment include lung cancer, head and neck cancer, breast cancer, pancreatic cancer, prostate cancer, renal cancer, bone cancer, testicular cancer, cervical cancer, gastrointestinal cancer, lymphomas, pre-neoplastic lesions in the lung, colon cancer, melanoma, and bladder cancer.

In some embodiments, the individual has cancer that is resistant (has been demonstrated to be resistant) to one or more anti-cancer therapies. In some embodiments, resistance to anti-cancer therapy includes recurrence of cancer or refractory cancer. Recurrence may refer to the reappearance of cancer, in the original site or a new site, after treatment. In some embodiments, resistance to anti-cancer therapy includes progression of the cancer during treatment with the anti-cancer therapy. In some embodiments, the cancer is at early stage or at late stage.

In some embodiments, the subject is also treated with an immune checkpoint inhibitor such as a PD-1 axis binding antagonist and/or an anti-CTLA-4 antibody. The individual may have a cancer that expresses (has been shown to express e.g., in a diagnostic test) PD-L1 biomarker or have a high tumor mutational burden. In some embodiments, the patient's cancer expresses low PD-L1 biomarker. In some embodiments, the patient's cancer expresses high PD-L1 biomarker. The PD-L1 biomarker can be detected in the sample using a method selected from the group consisting of FACS, Western blot, ELISA, immunoprecipitation, immunohistochemistry, immunofluorescence, radioimmunoassay, dot blotting, immunodetection methods, HPLC, surface plasmon resonance, optical spectroscopy, mass spectrometery, HPLC, qPCR, RT-qPCR, multiplex qPCR or RT-qPCR, RNA-seq, microarray analysis, SAGE, MassARRAY technique, and FISH, and combinations thereof. Measurement of a high mutational tumor burden may be determined by genomic sequencing (e.g., Foundation One CDx assay).

In some embodiments, the subject is also treated with a histone deacetylase (HDAC) inhibitor (e.g., tractinostat, formerly CHR-3996 or VRx-3996, an orally administered class 1 histone deacetylase selective inhibitor).

The efficacy of any of the methods described herein (e.g., combination treatments including administering an effective amount of a chimeric adenoviral vector optionally in combination of at least one CD122/CD132 agonist, a p53 and/or MDA-7 gene therapy, at least one immune checkpoint inhibitor, and/or at least one HDAC inhibitor may be tested in various models known in the art, such as clinical or pre-clinical models. Suitable pre-clinical models are exemplified herein and further may include without limitation ID8 ovarian cancer, GEM models, B16 melanoma, RENCA renal cell cancer, CT26 colorectal cancer, MC38 colorectal cancer, and Cloudman melanoma models of cancer.

In some embodiments of the methods of the present disclosure, the cancer has low levels of T cell infiltration. In some embodiments, the cancer has no detectable T cell infiltrate. In some embodiments, the cancer is a non-immunogenic cancer (e.g., non-immunogenic colorectal cancer and/or ovarian cancer). Without being bound by theory, the combination treatment may increase T cell (e.g., $CD4^+$ T cell, $CD8^+$ T cell, memory T cell) priming, activation and/or proliferation relative to prior to the administration of the combination.

In some embodiments of the methods of the present disclosure, activated CD4 and/or CD8 T cells in the individual are characterized by γ-IFN producing CD4 and/or CD8 T cells and/or enhanced cytolytic activity relative to prior to the administration of the combination. γ-IFN may be measured by any means known in the art, including, e.g., intracellular cytokine staining (ICS) involving cell fixation, permeabilization, and staining with an antibody against γ-IFN. Cytolytic activity may be measured by any means known in the art, e.g., using a cell killing assay with mixed effector and target cells.

The present disclosure is useful for any human cell that participates in an immune reaction either as a target for the immune system or as part of the immune system's response to the foreign target. The methods include ex vivo methods, in vivo methods, and various other methods that involve injection of polynucleotides or vectors into the host cell. The methods also include injection directly into the tumor or tumor bed as well as local or regional to the tumor.

A. Administration

The therapy provided herein comprises administration of a chimeric adenoviral vector which may be in combination with a preferential CD122/CD132 agonist (e.g., IL-2/anti-IL-2 immune complex, IL-15/anti-IL-15 immune complex, an IL-15/IL-15 Receptor α-IgG1-Fc (IL-15/IL-15Rα-IgG1-Fc) immunocomplex, PEGylated IL-2, PEGylated IL-15, IL-2 muteins and/or IL-15 muteins) and a p53 and/or MDA-7 gene therapy. The therapy may be administered in any suitable manner known in the art. For example, the adenoviral vector, CD122/CD132 agonist (e.g., IL-2/anti-IL-2 immune complex, IL-15/anti-IL-15 immune complex, an IL-15/IL-15 Receptor α-IgG1-Fc (IL-15/IL-15Rα-IgG1-Fc) immunocomplex, PEGylated IL-2, PEGylated IL-15, IL-2 muteins and/or IL-15 muteins) and a p53 and/or MDA-7 gene therapy may be administered sequentially (at different times) or concurrently (at the same time). In some embodiments, the adenoviral vector and the one or more additional therapies are in a separate composition. In some embodiments, the adenoviral vector and the one or more additional therapies are in the same composition. In certain aspects, the subject is administered the adenoviral vector before, simultaneously, or after the at least one additional therapy.

The adenoviral vector and one or more additional therapies may be administered by the same route of administration or by different routes of administration. In some embodiments, the adenoviral vector is administered intravenously, intramuscularly, subcutaneously, topically, orally, transdermally, intraperitoneally, intraorbitally, by implantation, by inhalation, intrathecally, intraventricularly, or intranasally. In some embodiments, the additional therapy is administered intravenously, intramuscularly, subcutaneously, topically, orally, transdermally, intraperitoneally, intraorbitally, by implantation, by inhalation, intrathecally, intraventricularly, or intranasally. An effective amount of the adenoviral vector and additional therapy may be administered for prevention or treatment of disease. The appropriate dosage of the adenoviral vector and additional therapy may be determined based on the type of disease to be treated, severity and course of the disease, the clinical condition of the individual, the individual's clinical history and response to the treatment, and the discretion of the attending physician. In some embodiments, combination treatment of the adenoviral vector with at least one CD122/CD132 agonist (e.g., IL-2/anti-IL-2 immune complex, IL-15/anti-IL-15 immune complex, an IL-15/IL-15 Receptor α-IgG1-Fc (IL-15/IL-15Rα-IgG1-Fc) immunocomplex, PEGylated IL-2, PEGylated IL-15, IL-2 muteins and/or IL-15 muteins) and a p53 and/or MDA-7 gene therapy are synergistic, whereby there is more than an additive effect of separate doses of the adenoviral vector in the combination with at the least one CD122/CD132 agonist (e.g., IL-2/anti-IL-2 immune complex, IL-15/anti-IL-15 immune complex, an IL-15/IL-15 Receptor α-IgG1-Fc (IL-15/IL-15Rα-IgG1-Fc) immunocomplex, PEGylated IL-2, PEGylated IL-15, IL-2 muteins and/or IL-15 muteins) compared to the treatment as a single agent.

For example, the therapeutically effective amount of the adenoviral vector and additional therapy, such as CD122/CD132 agonist, such as an IL-2/anti-IL-2 immune complex, IL-15/anti-IL-15 immune complex, an IL-15/IL-15 Receptor α-IgG1-Fc (IL-15/IL-15Rα-IgG1-Fc) immunocomplex, PEGylated IL-2, PEGylated IL-15, IL-2 muteins and/or IL-15 muteins) is administered in doses ranging between 5-100 ug/kg given either SQ or IV at intervals ranging from weekly to every 2-4 weeks.

For example, when the therapeutically effective amount an immune checkpoint inhibitor, such as an antibody, will be in the range of about 0.01 to about 50 mg/kg of patient body weight whether by one or more administrations. In some embodiments, the antibody used is about 0.01 to about 45 mg/kg, about 0.01 to about 40 mg/kg, about 0.01 to about 35 mg/kg, about 0.01 to about 30 mg/kg, about 0.01 to about 25 mg/kg, about 0.01 to about 20 mg/kg, about 0.01 to about 15 mg/kg, about 0.01 to about 10 mg/kg, about 0.01 to about 5 mg/kg, or about 0.01 to about 1 mg/kg administered daily, for example. In some embodiments, the antibody is administered at 15 mg/kg. However, other dosage regimens may be useful. In one embodiment, an anti-PD-L1 antibody described herein is administered to a human at a dose of about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg or about 1400 mg on day 1 of 21-day cycles. The dose may be administered as a single dose or as multiple doses (e.g., 2 or 3 doses), such as infusions. The progress of this therapy is easily monitored by conventional techniques.

Intratumoral injection, or injection into the tumor vasculature is specifically contemplated for the p53 and/or MDA-7 gene therapy component of the combined therapy. Local, regional or systemic administration also may be appropriate. For tumors of >4 cm, the volume to be administered will be about 4-10 ml (in particular 10 ml), while for tumors of <4 cm, a volume of about 1-3 ml will be used (in particular 3 ml). Multiple injections delivered as single dose comprise about 0.1 to about 0.5 ml volumes. For example, adenoviral particles may advantageously be contacted by administering multiple injections to the tumor.

Treatment regimens may vary as well, and often depend on tumor type, tumor location, disease progression, and health and age of the patient. Obviously, certain types of tumors will require more aggressive treatment, while at the same time, certain patients cannot tolerate more taxing protocols. The clinician will be best suited to make such decisions based on the known efficacy and toxicity (if any) of the therapeutic formulations.

In certain embodiments, the tumor being treated may not, at least initially, be resectable. The combined treatments may increase the resectability of the tumor due to shrinkage at the margins or by elimination of certain particularly invasive portions. Following the combined treatments, resection is performed. Additional treatments subsequent to resection will serve to eliminate residual disease.

The treatments may include various "unit doses." Unit dose is defined as containing a predetermined-quantity of the therapeutic composition. The quantity to be administered, and the particular route and formulation, are within the skill of those in the clinical arts. A unit dose need not be administered as a single injection but may comprise continuous infusion over a set period of time. Unit dose of the present invention may conveniently be described in terms of plaque forming units (pfu) for a viral construct. Unit doses range from $10^3$, $10^4$, $10^5$, $10^6$, $10^7$, $10^8$, $10^9$, $10^{10}$, $10^{11}$, $10^{12}$, $10^{13}$ pfu and higher. Alternatively, depending on the kind of virus and the titer attainable, one will deliver 1 to 100, 10 to 50, 100-1000, or up to about $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, or $1\times10^{15}$ or higher infectious viral particles (vp) to the patient or to the patient's cells.

B. Injectable Compositions and Formulations

The pharmaceutical compositions disclosed herein may alternatively be administered intra-tumorally, parenterally, intravenously, intradermally, intra-arterially, intramuscularly, transdermally or even intraperitoneally as described in U.S. Pat. Nos. 5,543,158, 5,641,515 and 5,399,363, all incorporated herein by reference.

Injection of adenoviral constructs may be delivered by syringe or any other method used for injection of a solution, as long as the expression construct can pass through the particular gauge of needle required for injection. A novel needleless injection system has been described (U.S. Pat. No. 5,846,233) having a nozzle defining an ampule chamber for holding the solution and an energy device for pushing the solution out of the nozzle to the site of delivery. A syringe system has also been described for use in gene therapy that permits multiple injections of predetermined quantities of a solution precisely at any depth (U.S. Pat. No. 5,846,225). Another injection system that may be used is the Quadra-Fuse device comprising a multipronged needle adjustable to different depths with an attached syringe.

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, intratumoral and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 22md Edition). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vaccuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like.

C. Additional Anti-Cancer Therapies

In order to increase the effectiveness of the chimeric adenoviral construct, it can be combined with at least one additional agent effective in the treatment of cancer. More generally, these other compositions would be provided in a combined amount effective to kill or inhibit proliferation of the cell. This process may involve contacting the cells with the expression construct and the agent(s) or multiple factor(s) at the same time. This may be achieved by contacting the cell with a single composition or pharmacological formulation that includes both agents, or by contacting the cell with two distinct compositions or formulations, at the same time, wherein one composition includes the expression construct and the other includes the second agent(s). Alternatively, the expression construct may contact the proliferating cell and the additional therapy may affect other cells of the immune system or the tumor microenvironment to enhance anti-tumor immune responses and therapeutic efficacy. The at least one additional anticancer therapy may be, without limitation, a surgical therapy, chemotherapy (e.g., administration of a protein kinase inhibitor or a EGFR-targeted therapy), radiation therapy, cryotherapy, hyperthermia treatment, phototherapy, radioablation therapy, hormonal therapy, immunotherapy including but not limited to immune checkpoint inhibitors, small molecule therapy, receptor kinase inhibitor therapy, anti-angiogenic therapy, cytokine therapy or a biological therapies such as monoclonal antibodies, siRNA, miRNA, antisense oligonucleotides, ribozymes or gene therapy. Without limitation the biological therapy may be a gene therapy, such as tumor suppressor gene therapy, a cell death protein gene therapy, a cell cycle regulator gene therapy, a cytokine gene therapy, a toxin gene therapy, an immunogene therapy, a suicide gene therapy, a prodrug gene therapy, an anti-cellular proliferation gene therapy, an enzyme gene therapy, or an anti-angiogenic factor gene therapy.

The adenoviral therapy may precede or follow the other agent treatment by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell. In such instances, it is contemplated that one may contact the cell with both modalities within about 12-24 hours of each other and, more preferably, within about 6-12 hours of each other. In some situations, it may be desirable to extend the time period for treatment significantly, however, where several days (e.g., 2, 3, 4, 5, 6 or 7) to several weeks (e.g., 1, 2, 3, 4, 5, 6, 7 or 8) lapse between the respective administrations. In certain embodiments, one or more of the therapies may be continued either with or without the others as maintenance therapy.

Various combinations may be employed, chimeric adenoviral vector is "A" and the secondary agent, i.e. an immune checkpoint inhibitor, is "B":

```
A/B/A B/A/B B/B/A A/A/B A/B/B B/A/A
A/B/B/B B/A/B/B B/B/B/A B/B/A/B A/A/B/B
A/B/A/B A/B/B/A B/B/A/A B/A/B/A B/A/A/B
A/A/A/B B/A/A/A A/B/A/A A/A/B/A
```

1. Chemotherapy

Cancer therapies in general also include a variety of combination therapies with both chemical and radiation based treatments. Combination chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, famesyl-protein transferase inhibitors, transplatinum, 5-fluorouracil, vincristine, vinblastine and methotrexate, Temazolomide (an aqueous form of DTIC), or any analog or derivative variant of the foregoing. The combination of chemotherapy with biological therapy is known as biochemotherapy. The chemotherapy may also be administered at low, continuous doses which is known as metronomic chemotherapy.

Yet further combination chemotherapies include, for example, alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammalI and calicheamicin omegaI1; dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids such as retinoic acid; capecitabine; carboplatin, procarbazine, plicomycin, gemcitabien, navelbine, farnesyl-protein transferase inhibitors, transplatinum; and pharmaceutically acceptable salts, acids or derivatives of any of the above. In certain embodiments, the compositions provided herein may be used in combination with histone deacetylase inhibitors. In certain embodiments, the compositions provided herein may be used in combination with gefitinib. In other embodiments, the present embodiments may be practiced in combination with Gleevec (e.g., from about 400 to about 800 mg/day of Gleevec may be administered to a patient). In certain embodiments, one or more chemotherapeutic may be used in combination with the compositions provided herein.

2. Radiotherapy

Other factors that cause DNA damage and have been used extensively include what are commonly known as y-rays, X-rays, and/or the directed delivery of radioisotopes to tumor cells. Other forms of DNA damaging factors are also known such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

3. Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells as well as genetically engineered variants of these cell types modified to express chimeric antigen receptors. Mda-7 gene transfer to tumor cells causes tumor cell death and apoptosis. The apoptotic tumor cells are scavenged by reticuloendothelial cells including dendritic cells and macrophages and presented to the immune system to generate anti-tumor immunity (Rovere et al., 1999; Steinman et al 1999).

It will be appreciated by those skilled in the art of cancer immunotherapy that other complementary immune therapies may be added to the regimens described above to further enhance their efficacy including but not limited to GM-C SF to increase the number of myeloid derived innate immune system cells, low dose cyclophosphamide or PI3K inhibitors (e.g., PI3K delta inhibitors) to eliminate T regulatory cells that inhibit innate and adaptive immunity and 5FU (e.g., capecitabine), PI3K inhibitors or histone deacetylase inhibitors to remove inhibitory myeloid derived suppressor cells. For example, PI3K inhibitors include, but are not limited to, LY294002, Perifosine, BKM120, Duvelisib, PX-866, BAY 80-6946, BEZ235, SF1126, GDC-0941, XL147, XL765, Palomid 529, GSK1059615, PWT33597, IC87114, TG100-15, CAL263, PI-103, GNE-477, CUDC-907, and AEZS-136. In some aspects, the PI3K inhibitor is a PI3K delta inhibitor such as, but not limited to, Idelalisib, RP6530, TGR1202, and RP6503. Additional PI3K inhibitors are disclosed in U.S. Patent Application Nos. US20150291595, US20110190319, and International Patent Application Nos. WO2012146667, WO2014164942, WO2012062748, and WO2015082376. The immunotherapy may also comprise the administration of an interleukin such as IL-2, or an interferon such as INFα.

Examples of immunotherapies that can be combined with the p53 and/or MDA-7 gene therapy and CD122/CD132 agonists are immune adjuvants (e.g., *Mycobacterium bovis, Plasmodium falciparum*, dinitrochlorobenzene and aromatic compounds) (U.S. Pat. Nos. 5,801,005; 5,739,169; Hui and Hashimoto, 1998; Christodoulides et al., 1998), cytokine therapy (e.g., interferons α, β and γ; interleukins (IL-1, IL-2), GM-CSF and TNF) (Bukowski et al., 1998; Davidson et al., 1998; Hellstrand et al., 1998) gene therapy (e.g., TNF, IL-1, IL-2, p53) (Qin et al., 1998; Austin-Ward and Villaseca, 1998; U.S. Pat. Nos. 5,830,880 and 5,846,945) and monoclonal antibodies (e.g., anti-ganglioside GM2, anti-HER-2, anti-p185) (Pietras et al., 1998; Hanibuchi et al., 1998; U.S. Pat. No. 5,824,311). Herceptin (trastuzumab) is a chimeric (mouse-human) monoclonal antibody that blocks the HER2-neu receptor. It possesses anti-tumor activity and has been approved for use in the treatment of malignant tumors (Dillman, 1999). Combination therapy of cancer with herceptin and chemotherapy has been shown to be more effective than the individual therapies. Thus, it is contemplated that one or more anti-cancer therapies may be employed with the p53 and/or MDA-7 gene therapy described herein.

Additional immunotherapies that may be combined with the p53 and/or MDA-7 gene therapy and CD122/CD132 agonists include immune checkpoint inhibitors, a co-stimulatory receptor agonist, a stimulator of innate immune cells, or an activator of innate immunity. In certain aspects the immune checkpoint inhibitor is an inhibitor of CTLA-4, PD-1, PD-L1, PD-L2, LAG-3, BTLA, B7H3, B7H4, TIM3, KIR, or A2aR. In some aspects, the at least one immune checkpoint inhibitor is an anti-CTLA-4 antibody. In some aspects, the anti-CTLA-4 antibody is tremelimumab or ipilimumab. In certain aspects, the at least one immune checkpoint inhibitor is an anti-killer-cell immunoglobulin-like receptor (KIR) antibody. In some embodiments, the anti-KIR antibody is lirilumab. In some aspects, the inhibitor of PD-L1 is durvalumab, atezolizumab, or avelumab. In some aspects, the inhibitor of PD-L2 is rHIgM12B7. In some aspects, the LAG3 inhibitor is IMP321, or BMS-986016. In some aspects, the inhibitor of A2aR is PBF-509.

In some aspects, the at least one immune checkpoint inhibitor is a human programmed cell death 1 (PD-1) axis binding antagonist. In certain aspects, the PD-1 axis binding antagonist is selected from the group consisting of a PD-1 binding antagonist, a PDL1 binding antagonist and a PDL2 binding antagonist. In some aspects, the PD-1 axis binding antagonist is a PD-1 binding antagonist. In certain aspects, the PD-1 binding antagonist inhibits the binding of PD-1 to PDL1 and/or PDL2. In particular, the PD-1 binding antagonist is a monoclonal antibody or antigen binding fragment thereof. In some embodiments, the PD-1 binding antagonist is nivolumab, pembrolizumab, pidilizumab, AMP-514, REGN2810, CT-011, BMS 936559, MPDL3280A or AMP-224.

In certain aspects, the at least one checkpoint inhibitor is selected from an inhibitor of CTLA-4, PD-1, PD-L1, PD-L2, LAG-3, BTLA, B7H3, B7H4, TIM3, KIR, or A2aR. In some aspects, the at least one immune checkpoint inhibitor is an anti-CTLA-4 antibody. In some aspects, the anti-CTLA-4 antibody is tremelimumab or ipilimumab. In certain aspects, the at least one immune checkpoint inhibitor is an anti-killer-cell immunoglobulin-like receptor (KIR) antibody. In some embodiments, the anti-KIR antibody is lirilumab. In some aspects, the inhibitor of PD-L1 is durvalumab, atezolizumab, or avelumab. In some aspects, the inhibitor of PD-L2 is rHIgM12B7. In some aspects, the LAG3 inhibitor is IMP321, or BMS-986016. In some aspects, the inhibitor of A2aR is PBF-509.

The co-stimulatory receptor agonist may be an anti-OX40 antibody (e.g., MEDI6469, MEDI6383, MEDI0562, and MOXR0916), anti-GITR antibody (e.g., TRX518, and MK-4166), anti-CD137 antibody (e.g., Urelumab, and PF-05082566), anti-CD40 antibody (e.g., CP-870,893, and Chi Lob 7/4), or an anti-CD27 antibody (e.g., Varlilumab, also known as CDX-1127). The stimulators of innate immune cells include, but are not limited to, a KIR monoclonal antibody (e.g., lirilumab), an inhibitor of a cytotoxicity-inhibiting receptor (e.g., NKG2A, also known as KLRC and as CD94, such as the monoclonal antibody monalizumab, and anti-CD96, also known as TACTILE), and a toll like receptor (TLR) agonist. The TLR agonist may be BCG, a TLR7 agonist (e.g., poly0ICLC, and imiquimod), a TLR8 agonist (e.g., resiquimod), or a TLR9 agonist (e.g., CPG 7909). The activators of innate immune cells, such as natural killer (NK) cells, macrophages, and dendritic cells, include IDO inhibitors, TGFβ inhibitor, IL-10 inhibitor. An exemplary activator of innate immunity is Indoximod. In some aspects, the immunotherapy is a stimulator of interferon genes (STING) agonist (Corrales et al., 2015).

Other immunotherapies contemplated for use in methods of the present disclosure include those described by Tchekmedyian et al., 2015, incorporated herein by reference. The immunotherapy may comprise suppression of T regulatory cells (Tregs), myeloid derived suppressor cells (MDSCs) and cancer associated fibroblasts (CAFs). In some embodiments, the immunotherapy is a tumor vaccine (e.g., whole tumor cell vaccines, dendritic cell vaccines, DNA and/or RNA expression vaccines, peptides, and recombinant tumor associated antigen vaccines), or adoptive cellular therapies (ACT) (e.g., T cells, natural killer cells, TILs, and LAK cells). The T cells and/or natural killer cells may be engineered with chimeric antigen receptors (CARs) or T cell receptors (TCRs) to specific tumor antigens. As used herein, a chimeric antigen receptor (or CAR) may refer to any engineered receptor specific for an antigen of interest that, when expressed in a T cell or natural killer cell, confers the specificity of the CAR onto the T cell or natural killer cell. Once created using standard molecular techniques, a T cell or natural killer cell expressing a chimeric antigen receptor may be introduced into a patient, as with a technique such as adoptive cell transfer. In some aspects, the T cells are activated CD4 and/or CD8 T cells in the individual which are characterized by γ-IFN" producing CD4 and/or CD8 T cells and/or enhanced cytolytic activity relative to prior to the administration of the combination. The CD4 and/or CD8 T cells may exhibit increased release of cytokines selected from the group consisting of IFN-γ, TNF-α and interleukins. The CD4 and/or CD8 T cells can be effector memory T cells. In certain embodiments, the CD4 and/or CD8 effector memory T cells are characterized by having the expression of $CD44^{high}$ $CD62L^{low}$.

In certain aspects, two or more immunotherapies may be combined with the p53 and/or MDA-7 gene therapy and CD122/CD132 agonists including additional immune checkpoint inhibitors in combination with agonists of T-cell costimulatory receptors, or in combination with TIL ACT. Other combinations include T-cell checkpoint blockade plus costimulatory receptor agonists, T-cell checkpoint blockade to improve innate immune cell function, checkpoint blockade plus IDO inhibition, or checkpoint blockade plus adoptive T-cell transfer. In certain aspects, immunotherapy includes a combination of an anti-PD-L1 immune checkpoint inhibitor (e.g., Avelumab), a 4-1BB (CD-137) agonist (e.g. Utomilumab), and an OX40 (TNFRS4) agonist. The immunotherapy may be combined with histone deacetylase (HDAC) inhibitors such as 5-azacytidine and entinostat.

The immunotherapy may be a cancer vaccine comprising one or more cancer antigens, in particular a protein or an immunogenic fragment thereof, DNA or RNA encoding said cancer antigen, in particular a protein or an immunogenic fragment thereof, cancer cell lysates, and/or protein preparations from tumor cells. As used herein, a cancer antigen is an antigenic substance present in cancer cells. In principle, any protein produced in a cancer cell that is upregulated in cancer cells compared to normal cells or has an abnormal structure due to mutation can act as a cancer antigen. In principle, cancer antigens can be products of mutated or overexpressed oncogenes and tumor suppressor genes, products of other mutated genes, overexpressed or aberrantly expressed cellular proteins, cancer antigens produced by oncogenic viruses, oncofetal antigens, altered cell surface glycolipids and glycoproteins, or cell type-specific differentiation antigens. Examples of cancer antigens include the abnormal or overexpressed products of ras and p53 genes. Other examples include tissue differentiation antigens, mutant protein antigens, oncogenic viral antigens, cancer-testis antigens and vascular or stromal specific antigens. Tissue differentiation antigens are those that are specific to a certain type of tissue. Mutant protein antigens are likely to be much more specific to cancer cells because normal cells shouldn't contain these proteins. Normal cells will display the normal protein antigen on their MHC molecules, whereas cancer cells will display the mutant version. Some viral proteins are implicated in forming cancer, and some viral antigens are also cancer antigens. Cancer-testis antigens are antigens expressed primarily in the germ cells of the testes, but also in fetal ovaries and the trophoblast. Some cancer cells aberrantly express these proteins and therefore present these antigens, allowing attack by T-cells specific to these antigens. Exemplary antigens of this type are CTAG1 B and MAGEA1 as well as Rindopepimut, a 14-mer intradermal injectable peptide vaccine targeted against epidermal growth factor receptor (EGFR) vlll variant. Rindopepimut is particularly suitable for treating glioblastoma when used in combination with an inhibitor of the CD95/CD95L signaling system as described herein. Also, proteins that are normally produced in very low quantities, but whose production is dramatically increased in cancer cells, may trigger an immune response. An example of such a protein is the enzyme tyrosinase, which is required for melanin production. Normally tyrosinase is produced in minute quantities but its levels are very much elevated in melanoma cells. Oncofetal antigens are another important class of cancer antigens. Examples are alphafetoprotein (AFP) and carcinoembryonic antigen (CEA). These proteins are normally produced in the early stages of embryonic development and disappear by the time the immune system is fully developed. Thus self-tolerance does not develop against these antigens. Abnormal proteins are also produced by cells infected with oncoviruses, e.g. EBV and HPV. Cells infected by these viruses contain latent viral DNA which is transcribed and the resulting protein produces an immune response. A cancer vaccine may include a peptide cancer vaccine, which in some embodiments is a personalized peptide vaccine. In some embodiments, the peptide cancer vaccine is a multivalent long peptide vaccine, a multi-peptide vaccine, a peptide cocktail vaccine, a hybrid peptide vaccine, or a peptide-pulsed dendritic cell vaccine.

The immunotherapy may be an antibody, such as part of a polyclonal antibody preparation, or may be a monoclonal antibody. The antibody may be a humanized antibody, a chimeric antibody, an antibody fragment, a bispecific antibody or a single chain antibody. An antibody as disclosed herein includes an antibody fragment, such as, but not limited to, Fab, Fab' and F(ab')2, Fd, single-chain Fvs (scFv), single-chain antibodies, disulfide-linked Fvs (sdfv) and fragments including either a VL or VH domain. In some aspects, the antibody or fragment thereof specifically binds epidermal growth factor receptor (EGFR1, Erb-B1), HER2/neu (Erb-B2), CD20, Vascular endothelial growth factor (VEGF), insulin-like growth factor receptor (IGF-1R), TRAIL-receptor, epithelial cell adhesion molecule, carcinoembryonic antigen, Prostate-specific membrane antigen, Mucin-1, CD30, CD33, or CD40.

Examples of monoclonal antibodies that may be used in combination with the compositions provided herein include, without limitation, trastuzumab (anti-HER2/neu antibody); Pertuzumab (anti-HER2 mAb); cetuximab (chimeric monoclonal antibody to epidermal growth factor receptor EGFR); panitumumab (anti-EGFR antibody); nimotuzumab (anti-EGFR antibody); Zalutumumab (anti-EGFR mAb); Necitumumab (anti-EGFR mAb); MDX-210 (humanized anti-HER-2 bispecific antibody); MDX-210 (humanized anti-HER-2 bispecific antibody); MDX-447 (humanized anti-EGF receptor bispecific antibody); Rituximab (chimeric murine/human anti-CD20 mAb); Obinutuzumab (anti-CD20 mAb); Ofatumumab (anti-CD20 mAb); Tositumumab-I131 (anti-CD20 mAb); Ibritumomab tiuxetan (anti-CD20 mAb); Bevacizumab (anti-VEGF mAb); Ramucirumab (anti-VEGFR2 mAb); Ranibizumab (anti-VEGF mAb); Aflibercept (extracellular domains of VEGFR1 and VEGFR2 fused to IgG1 Fc); AMG386 (angiopoietin-1 and -2 binding peptide fused to IgG1 Fc); Dalotuzumab (anti-IGF-1R mAb); Gemtuzumab ozogamicin (anti-CD33 mAb); Alemtuzumab (anti-Campath-1/CD52 mAb); Brentuximab vedotin (anti-CD30 mAb); Catumaxomab (bispecific mAb that targets epithelial cell adhesion molecule and CD3); Naptumomab (anti-5T4 mAb); Girentuximab (anti-Carbonic anhydrase ix); or Farletuzumab (anti-folate receptor). Other examples include antibodies such as Panorex™ (17-1A) (murine monoclonal antibody); Panorex (@(17-1A) (chimeric murine monoclonal antibody); BEC2 (ami-idiotypic mAb, mimics the GD epitope) (with BCG); Oncolym (Lym-1 monoclonal antibody); SMART M195 Ab, humanized 13' 1 LYM-1 (Oncolym), Ovarex (B43.13, anti-idiotypic mouse mAb); 3622W94 mAb that binds to EGP40 (17-1A) pancarcinoma antigen on adenocarcinomas; Zenapax (SMART Anti-Tac (IL-2 receptor); SMART M195 Ab, humanized Ab, humanized); NovoMAb-G2 (pancarcinoma specific Ab); TNT (chimeric mAb to histone antigens); TNT (chimeric mAb to histone antigens); Gliomab-H (Monoclonals-Humanized Abs); GNI-250 Mab; EMD-72000 (chimeric-EGF antagonist); LymphoCide (humanized IL.L.2 antibody); and MDX-260 bispecific, targets GD-2, ANA Ab, SMART IDIO Ab, SMART ABL 364 Ab or ImmuRAIT-CEA. Examples of antibodies include those disclosed in U.S. Pat. Nos. 5,736,167, 7,060,808, and 5,821,337.

Further examples of antibodies include Zanulimumab (anti-CD4 mAb), Keliximab (anti-CD4 mAb); Ipilimumab (MDX-101; anti-CTLA-4 mAb); Tremilimumab (anti-CTLA-4 mAb); (Daclizumab (anti-CD25/IL-2R mAb); Basiliximab (anti-CD25/IL-2R mAb); MDX-1106 (anti-PD1 mAb); antibody to GITR; GC1008 (anti-TGF-β antibody); metelimumab/CAT-192 (anti-TGF-β antibody); lerdelimumab/CAT-152 (anti-TGF-β antibody); ID11 (anti-TGF-β antibody); Denosumab (anti-RANKL mAb); BMS-663513 (humanized anti-4-1BB mAb); SGN-40 (humanized anti-CD40 mAb); CP870,893 (human anti-CD40 mAb); Infliximab (chimeric anti-TNF mAb; Adalimumab (human anti-TNF mAb); Certolizumab (humanized Fab anti-TNF); Golimumab (anti-TNF); Etanercept (Extracellular domain of TNFR fused to IgG1 Fc); Belatacept (Extracellular domain of CTLA-4 fused to Fc); Abatacept (Extracellular domain of CTLA-4 fused to Fc); Belimumab (anti-B Lymphocyte stimulator); Muromonab-CD3 (anti-CD3 mAb); Otelixizumab (anti-CD3 mAb); Teplizumab (anti-CD3 mAb); Tocilizumab (anti-IL6R mAb); REGN88 (anti-IL6R mAb); Ustekinumab (anti-IL-12/23 mAb); Briakinumab (anti-IL-12/23 mAb); Natalizumab (anti-α4 integrin); Vedolizumab (anti-α4 β7 integrin mAb); T1 h (anti-CD6 mAb); Epratuzumab (anti-CD22 mAb); Efalizumab (anti-CD11a mAb); and Atacicept (extracellular domain of transmembrane activator and calcium-modulating ligand interactor fused with Fc).

a. Passive Immunotherapy

A number of different approaches for passive immunotherapy of cancer exist. They may be broadly categorized into the following: injection of antibodies alone; injection of antibodies coupled to toxins or chemotherapeutic agents; injection of antibodies coupled to radioactive isotopes; injection of anti-idiotype antibodies; and finally, purging of tumor cells in bone marrow.

Preferably, human monoclonal antibodies are employed in passive immunotherapy, as they produce few or no side effects in the patient. Human monoclonal antibodies to ganglioside antigens have been administered intralesionally to patients suffering from cutaneous recurrent melanoma (Irie & Morton, 1986). Regression was observed in six out of ten patients, following, daily or weekly, intralesional injections. In another study, moderate success was achieved from intralesional injections of two human monoclonal antibodies (Irie et al., 1989).

It may be favorable to administer more than one monoclonal antibody directed against two different antigens or even antibodies with multiple antigen specificity. Treatment protocols also may include administration of lymphokines or other immune enhancers as described by Bajorin et al. (1988). The development of human monoclonal antibodies is described in further detail elsewhere in the specification.

b. Active Immunotherapy

In active immunotherapy, an antigenic peptide, polypeptide or protein, or an autologous or allogenic tumor cell composition or "vaccine" is administered, generally with a distinct bacterial adjuvant (Ravindranath & Morton, 1991; Morton & Ravindranath, 1996; Morton et al., 1992; Mitchell et al., 1990; Mitchell et al., 1993). In melanoma immunotherapy, those patients who elicit high IgM response often survive better than those who elicit no or low IgM antibodies (Morton et al., 1992). IgM antibodies are often transient antibodies and the exception to the rule appears to be anti-ganglioside or anticarbohydrate antibodies.

c. Adoptive Immunotherapy

In adoptive immunotherapy, the patient's circulating lymphocytes, or tumor infiltrated lymphocytes, are isolated in vitro, activated by lymphokines such as IL-2 or transduced with genes for tumor necrosis, and readministered (Rosenberg et al., 1988; 1989). To achieve this, one would administer to an animal, or human patient, an immunologically effective amount of activated lymphocytes in combination with an adjuvant-incorporated antigenic peptide composition as described herein. The activated lymphocytes will most preferably be the patient's own cells that were earlier isolated from a blood or tumor sample and activated (or "expanded") in vitro. This form of immunotherapy has produced several cases of regression of melanoma and renal carcinoma, but the percentage of responders were few compared to those who did not respond. More recently, higher response rates have been observed when such adoptive immune cellular therapies have incorporated genetically engineered T cells that express chimeric antigen receptors (CAR) termed CAR T cell therapy. Similarly, natural killer cells both autologous and allogenic have been isolated, expanded and genetically modified to express receptors or ligands to facilitate their binding and killing of tumor cells.

4. Other Agents

It is contemplated that other agents may be used in combination with the compositions provided herein to improve the therapeutic efficacy of treatment. These additional agents include immunomodulatory agents, agents that affect the upregulation of cell surface receptors and GAP junctions, cytostatic and differentiation agents, inhibitors of cell adhesion, or agents that increase the sensitivity of the hyperproliferative cells to apoptotic inducers. Immunomodulatory agents include tumor necrosis factor; interferon alpha, beta, and gamma; IL-2 and other cytokines; or MIP-1, MIP-1beta, MCP-1, RANTES, and other chemokines. It is further contemplated that the upregulation of cell surface receptors or their ligands such as Fas/Fas ligand, DR4 or DR5/TRAIL would potentiate the apoptotic inducing abilities of the compositions provided herein by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the compositions provided herein to improve the anti-hyerproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the compositions provided herein to improve the treatment efficacy.

In further embodiments, the other agents may be one or more oncolytic viruses. These oncolytic viruses may be engineered to express p53 and/or IL24 and/or to express a gene other than p53 and/or IL24, such as a cytokine or a heat shock protein. Examples of oncolytic viruses include single or double stranded DNA viruses, RNA viruses, adenoviruses, adeno-associated viruses, retroviruses, lentiviruses, herpes viruses, pox viruses, vaccinia viruses, vesicular stomatitis viruses, polio viruses, Newcastle's Disease viruses, Epstein-Barr viruses, influenza viruses and reoviruses, myxoma viruses, maraba viruses, rhabdoviruses, enadenotucirev or coxsackie viruses. In a particular embodiment, the other agent is talimogene laherparepvec (T-VEC) which is an oncolytic herpes simplex virus genetically engineered to express GM-CSF. Talimogene laherparepvec, HSV-1 [strain JS1] ICP34.5-/ICP47-/hGM-CSF, (previously known as OncoVEX$^{GM\ CSF}$) is an intratumorally delivered oncolytic immunotherapy comprising an immune-enhanced HSV-1 that selectively replicates in solid tumors. (Lui et al., *Gene Therapy,* 10:292-303, 2003; U.S. Pat. Nos. 7,223,593 and 7,537,924; incorporated herein by reference). In October 2015, the US FDA approved T-VEC, under the brand name IMLYGIC™, for the treatment of melanoma in patients with inoperable tumors. The characteristics and methods of administration of T-VEC are described in, for example, the IMLYGIC™ package insert (Amgen, 2015) and U.S. Patent Publication No. US2015/0202290; both incorporated herein by reference. For example, talimogene laherparepvec is typically administered by intratumoral injection into injectable cutaneous, subcutaneous, and nodal tumors at a dose of up to 4.0 ml of $10^6$ plaque forming unit/mL (PFU/mL) at day 1 of week 1 followed by a dose of up to 4.0 ml of $10^8$ PFU/mL at day 1 of week 4, and every 2 weeks (±3 days) thereafter. The recommended volume of talimogene laherparepvec to be injected into the tumor(s) is dependent on the size of the tumor(s) and should be determined according to the injection volume guideline. While T-VEC has demonstrated clinical activity in melanoma patients, many cancer patients either do not respond or cease responding to T-VEC treatment. In one embodiment, the p53 and/or MDA-7 nucleic acids and the at least one CD122/CD132 agonist may be administered after, during or before T-VEC therapy, such as to reverse treatment resistance. Exemplary oncolytic viruses include, but are not limited to, Ad5-yCD/mutTKSR39rep-hIL12, Cavatak™, CG0070, DNX-2401, G207, HF10, IMLYGIC™, JX-594, MG1-MA3, MV-NIS, OBP-301, Reolysin®, Toca 511, Oncorine (H101), Onyx-015, H102, H103, and RIGVIR. Other exemplary oncolytic viruses are described, for example, in International Patent Publication Nos. WO2015/027163, WO2014/138314, WO2014/047350, and WO2016/009017; all incorporated herein by reference.

In certain embodiments, hormonal therapy may also be used in conjunction with the present embodiments or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases In some aspects, the additional anti-cancer agent is a protein kinase inhibitor or a monoclonal antibody that inhibits receptors involved in protein kinase or growth factor signaling pathways such as an EGFR, VEGFR, AKT, Erb 1, Erb2, ErbB, Syk, Bcr-Abl, JAK, Src, GSK-3, PI3K, Ras, Raf, MAPK, MAPKK, mTOR, c-Kit, eph receptor or BRAF inhibitors. Nonlimiting examples of protein kinase or growth factor signaling pathways inhibitors include Afatinib, Axitinib, Bevacizumab, Bosutinib, Cetuximab, Crizotinib, Dasatinib, Erlotinib, Fostamatinib, Gefitinib, Imatinib, Lapatinib, Lenvatinib, Mubritinib, Nilotinib, Panitumumab, Pazopanib, Pegaptanib, Ranibizumab, Ruxolitinib, Saracatinib, Sorafenib, Sunitinib, Trastuzumab, Vandetanib, AP23451, Vemurafenib, MK-2206, GSK690693, A-443654, VQD-002, Miltefosine, Perifosine, CAL101, PX-866, LY294002, rapamycin, temsirolimus, everolimus, ridaforolimus, Alvocidib, Genistein, Selumetinib, AZD-6244, Vatalanib, P1446A-05, AG-024322, ZD1839, P276-00, GW572016 or a mixture thereof.

In some aspects, the PI3K inhibitor is selected from the group of PI3K inhibitors consisting of buparlisib, idelalisib, BYL-719, dactolisib, PF-05212384, pictilisib, copanlisib, copanlisib dihydrochloride, ZSTK-474, GSK-2636771, duvelisib, GS-9820, PF-04691502, SAR-245408, SAR-245409, sonolisib, Archexin, GDC-0032, GDC-0980, apitolisib, pilaralisib, DLBS 1425, PX-866, voxtalisib, AZD-8186, BGT-226, DS-7423, GDC-0084, GSK-21 26458, INK-1 1 17, SAR-260301, SF-1 1 26, AMG-319, BAY-1082439, CH-51 32799, GSK-2269557, P-71 70, PWT-33597, CAL-263, RG-7603, LY-3023414, RP-5264, RV-1729, taselisib, TGR-1 202, GSK-418, INCB-040093, Panulisib, GSK-105961 5, CNX-1351, AMG-51 1, PQR-309, 17beta-Hydroxywortmannin, AEZS-129, AEZS-136, HM-5016699, IPI-443, ONC-201, PF-4989216, RP-6503, SF-2626, X-339, XL-499, PQR-401, AEZS-132, CZC-24832, KAR-4141, PQR-31 1, PQR-316, RP-5090, VS-5584, X-480, AEZS-126, AS-604850, BAG-956, CAL-130, CZC-24758, ETP-46321, ETP-471 87, GNE-317, GS-548202, HM-032, KAR-1 139, LY-294002, PF-04979064, PI-620, PKI-402, PWT-143, RP-6530, 3-HOI-BA-01, AEZS-134, AS-041 164, AS-252424, AS-605240, AS-605858, AS-606839, BCCA-621 C, CAY-10505, CH-5033855, CH-51 08134, CUDC-908, CZC-1 9945, D-106669, D-87503, DPT-NX7, ETP-46444, ETP-46992, GE-21, GNE-123, GNE-151, GNE-293, GNE-380, GNE-390, GNE-477, GNE-490, GNE-493, GNE-614, HMPL-51 8, HS-104, HS-1 06, HS-1 16, HS-173, HS-196, IC-486068, INK-055, KAR 1 141, KY-1 2420, Wortmannin, Lin-05, NPT-520-34, PF-04691503, PF-06465603, PGNX-01, PGNX-02, PI 620, PI-103, PI-509, PI-516, PI-540, PIK-75, PWT-458, RO-2492, RP-5152, RP-5237, SB-201 5, SB-2312, SB-2343, SHBM-1009, SN 32976, SR-13179, SRX-2523, SRX-2558, SRX-2626, SRX-3636, SRX-5000, TGR-5237, TGX-221, UCB-5857, WAY-266175, WAY-266176, EI-201, AEZS-131, AQX-MN100, KCC-TGX, OXY-1 1 1 A, PI-708, PX-2000, and WJD-008.

It is contemplated that the additional cancer therapy can comprise an antibody, peptide, polypeptide, small molecule inhibitor, siRNA, miRNA or gene therapy which targets, for example, epidermal growth factor receptor (EGFR, EGFR1, ErbB-1, HER1), ErbB-2 (HER2/neu), ErbB-3/HER3, ErbB-4/HER4, EGFR ligand family; insulin-like growth factor receptor (IGFR) family, IGF-binding proteins (IGFBPs), IGFR ligand family (IGF-1R); platelet derived growth factor receptor (PDGFR) family, PDGFR ligand family; fibroblast growth factor receptor (FGFR) family, FGFR ligand family, vascular endothelial growth factor receptor (VEGFR) family, VEGF family; HGF receptor family: TRK receptor family; ephrin (EPH) receptor family; AXL receptor family; leukocyte tyrosine kinase (LTK) receptor family; TIE receptor family, angiopoietin 1, 2; receptor tyrosine kinase-like orphan receptor (ROR) receptor family; discoidin domain receptor (DDR) family; RET receptor family; KLG receptor family; RYK receptor family; MuSK receptor family; Transforming growth factor alpha (TGF-$\alpha$), TGF-$\alpha$ receptor; Transforming growth factor-beta (TGF-$\beta$), TGF-$\beta$ receptor; Interleukin 13 receptor alpha2 chain (1L13Ralpha2), Interleukin-6 (IL-6), 1L-6 receptor, Interleukin-4, IL-4 receptor, Cytokine receptors, Class I (hematopoietin family) and Class II (interferon/1L-10 family) receptors, tumor necrosis factor (TNF) family, TNF-$\alpha$, tumor necrosis factor (TNF) receptor superfamily (TNTRSF), death receptor family, TRAIL-receptor; cancer-testis (CT) antigens, lineage-specific antigens, differentiation antigens, alpha-actinin-4, ARTC1, breakpoint cluster region-Abelson (Bcr-abl) fusion products, B-RAF, caspase-5 (CASP-5), caspase-8 (CASP-8), beta-catenin (CTNNB1), cell division cycle 27 (CDC27), cyclin-dependent kinase 4 (CDK4), CDKN2A, COA-1, dek-can fusion protein, EFTUD-2, Elongation factor 2 (ELF2), Ets variant gene 6/acute myeloid leukemia 1 gene ETS (ETC6-AML1) fusion protein, fibronectin (FN), GPNMB, low density lipid receptor/GDP-L fucose: beta-Dgalactose 2-alpha-Lfucosyltraosferase (LDLR/FUT) fusion protein, HLA-A2, arginine to isoleucine exchange at residue 170 of the alpha-helix of the alpha2-domain in the HLA-A2 gene (HLA-A*201-R170I), MLA-A11, heat shock protein 70-2 mutated (HSP70-2M), KIAA0205, MART2, melanoma ubiquitous mutated 1, 2, 3 (MUM-1, 2, 3), prostatic acid phosphatase (PAP), neo-PAP, Myosin class 1, NFYC, OGT, OS-9, pml-RARalpha fusion protein, PRDX5, PTPRK, K-ras (KRAS2), N-ras (NRAS), HRAS, RBAF600, SIRT2, SNRPD1, SYT-SSX1 or -SSX2 fusion protein, Triosephosphate Isomerase, BAGE, BAGE-1, BAGE-2,3,4,5, GAGE-1,2,3,4,5,6,7,8, GnT-V (aberrant N-acetyl giucosaminyl transferase V, MGATS), HERV-K-MEL, KK-LC, KM-HN-1, LAGE, LAGE-1, CTL-recognixed antigen on melanoma (CAMEL), MAGE-A1 (MAGE-1), MAGE-A2, MAGE-A3, MAGE-A4, MAGE-AS, MAGE-A6, MAGE-A8, MAGE-A9, MAGE-A10, MAGE-A11, MAGE-A12, MAGE-3, MAGE-B1, MAGE-B2, MAGE-B5, MAGE-B6, MAGE-C1, MAGE-C2, mucin 1 (MUC1), MART-1/Melan-A (MLANA), gp100, gp100/Pme117 (S1LV), tyrosinase (TYR), TRP-1, HAGE, NA-88, NY-ESO-1, NY-ESO-1/LAGE-2, SAGE, Sp17, SSX-1,2,3,4, TRP2-1NT2, carcino-embryonic antigen (CEA), Kallikfein 4, mammaglobm-A, OA1, prostate specific antigen (PSA), prostate specific membrane antigen, TRP-1/gp75, TRP-2, adipophilin, interferon inducible protein absent in nielanorna 2 (AIM-2), BING-4, CPSF, cyclin D1, epithelial cell adhesion molecule (Ep-CAM), EpbA3, fibroblast growth factor-5 (FGF-5), glycoprotein 250 (gp250intestinal carboxyl esterase (iCE), alpha-feto protein (AFP), M-CSF, mdm-2 (e.g., small molecule inhibitor of HDM2, also known as MDM2, and/or HDM4, such as to reverse its inhibition of p53 activity, such as HDM201, cis-imidazolines (e.g., Nutlins), benzodiazepines (BDPs), spiro-oxindoles), MUCI, p53 (TP53), PBF, FRAME, PSMA, RAGE-1, RNF43, RU2AS, SOX10, STEAP1, survivin (BIRCS), human telomerase reverse transcriptase (hTERT), telomerase, Wilms' tumor gene (WT1), SYCP1, BRDT, SPANX, XAGE, ADAM2, PAGE-5, LIP1, CTAGE-1, CSAGE, MMA1, CAGE, BORIS, HOM-TES-85, AF15q14, HCA66I, LDHC, MORC, SGY-1, SPO11, TPX1, NY-SAR-35, FTHLI7, NXF2 TDRD1, TEX 15, FATE, TPTE, immunoglobulin idiotypes, Bence-Jones protein, estrogen receptors (ER), androgen receptors (AR), CD40, CD30, CD20, CD19, CD33, CD4, CD25, CD3, cancer antigen 72-4 (CA 72-4), cancer antigen 15-3 (CA 15-3), cancer antigen 27-29 (CA 27-29), cancer antigen 125 (CA 125), cancer antigen 19-9 (CA 19-9), beta-human chorionic gonadotropin, 1-2 microglobulin, squamous cell carcinoma antigen, neuron-specific enolase, heat shock protein gp96, GM2, sargramostim, CTLA-4, 707 alanine proline (707-AP), adenocarcinoma antigen recognized by T cells 4 (ART-4), carcinoembryogenic antigen peptide-1 (CAP-1), calcium-activated chloride channel-2 (CLCA2), cyclophilin B (Cyp-B), human signet ring tumor-2 (HST-2), Human papilloma virus (HPV) proteins (HPV-E6, HPV-E7, major or minor capsid antigens, others), Epstein-Barr vims (EBV) proteins (EBV latent membrane proteins—LMP1, LMP2; others), Hepatitis B or C virus proteins, and HIV proteins.

VIII. ARTICLES OF MANUFACTURE OR KITS

An article of manufacture or a kit is provided comprising the present chimeric adenoviral vectors and, optionally, at least one CD122/CD132 agonist (e.g., IL-2/anti-IL-2 immune complex, IL-15/anti-IL-15 immune complex, an IL-15/IL-15 Receptor α-IgG1-Fc (IL-15/IL-15Rα-IgG1-Fc) immunocomplex, PEGylated IL-2, PEGylated IL-15, IL-2 muteins, IL-15 muteins), a nucleic acid encoding p53 and/or a nucleic acid encoding MDA-7 (e.g. ad-p53 and/or ad-MDA-7) is also provided herein. The article of manufacture or kit can further comprise a package insert comprising instructions for using the chimeric adenoviral vector to treat or delay progression of cancer in an individual or to enhance immune function of an individual having cancer. Any of the therapies described herein may be included in the article of manufacture or kits. The kit may additionally comprise an extracellular matrix degrading protein or expression construct encoding the extracellular matrix degrading protein.

In some embodiments, the present therapies are in the same container or separate containers. Suitable containers include, for example, bottles, vials, bags and syringes. The container may be formed from a variety of materials such as glass, plastic (such as polyvinyl chloride or polyolefin), or metal alloy (such as stainless steel or hastelloy). In some embodiments, the container holds the formulation and the label on, or associated with, the container may indicate directions for use. The article of manufacture or kit may further include other materials desirable from a commercial and user standpoint, including other buffers, diluents, filters, needles, syringes, and package inserts with instructions for use. In some embodiments, the article of manufacture further includes one or more of another agent (e.g., a chemotherapeutic agent, and anti-neoplastic agent). Suitable containers for the one or more agent include, for example, bottles, vials, bags and syringes.

IX. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Stability, Transgene Expression Levels, and Safety of Adenoviral Vectors with Genetically Modified Fibers Incorporating Various Peptide Motifs A series of replication competent adenoviral vectors were generated with genetically modified fibers incorporating either RGD, REA, LyP-1, and NGR peptide motifs with chimeric Ad5/Ad48 hexons expressing soluble transforming growth factor beta receptor II-Fc fusion protein (sTGβRIIFc). All of the viruses had E1A 01/07 mutations. These constructs were evaluated and compared with respect to multiple characteristics required for their successful use as systemic therapeutic agents. The tests included evaluations for virus stability, transgene expression and in vivo safety employing standard methods as described below.

Viral stability assays. Viral vectors were frozen at −80° for various days (30 or 60 days). Subsequently, viruses were thawed at room temperature for 2 minutes. Frozen and thawed adenovirus samples were used to infect breast cancer cells, and sTGFβRIIFc expression was quantified as described in the next section. The viral stability is directly proportional to the viral-mediated sTGFβRIIFc expression in the breast tumor cells.

sTGFβRIIFc expression in the tumor cells. Cells were plated in 6-well dishes ($5\times10^5$ cells/well). The next day, cells were incubated with adenoviral vectors ($2.5\times10^3$ viral particles (VPs)/cell) for 24 hrs. Media were changed to serum free media, and the incubations continued for another 24 hrs. Both media and cell lysates were subjected to Western blot analyses for sTGFβRIIFc expression as previously described (Hu et al., 2012). sTGβRIIFc levels in the media were also examined by enzyme-linked immunosorbent assay (ELISA) as previously described (Hu et al., 2010).

Adenoviral replication assays. Cells were plated in 6-well dishes ($5\times10^5$ cells/well). The next day, cells were incubated with adenoviral vectors ($2.5\times10^4$ viral particles (VPs)/cell) for 3 hrs. After cells were washed three times with media, 3 hrs samples were collected to prepare crude viral lysates, and 48 hrs samples were collected after the incubations continued for 48 hrs. Various aliquots of 3 hrs and 48 hrs crude viral lysates were used to infect HEK293 cells according to Adeno-X Rapid Titer Kit Protocol as described earlier (Zhang et al. 2012). Hexon expressing positive brown cells were photographed, and counted under the microscope to quantify viral replication. Viral titers were represented as the viral burst size (an increase in positive hexon expressing cells from 3 hrs to 48 hrs).

Adenoviral-induced cytotoxicity assays. To examine viral-induced cytotoxicity, cells were plated in 96-well plates ($10^3$ cells/well) as previously described (Hu et al., 2012). The next day, cells were infected with various doses of adenoviral vectors, and the incubations continued for 7 days. Cells were washed, fixed and stained with sulforhodamine B and the absorbance at 564 nm ($A_{564}$) was measured as previously described (Katayose et al., 1995). Untreated control cells were considered to have 100% survival.

Liver toxicity studies. Six-week old nude mice were injected with low dose (LD=$2.5\times10^{10}$ VPs/mouse) or medium dose (MD=$1.0\times10^{11}$ VPs/mouse) of Ad.sT, AdLyp.sT, mHAd.sT, or mHAdLyp.sT via tail vein. Three days after virus injection, their body weights were measured before they were euthanized. The livers were photographed. The liver samples were collected and processed for hematoxylin and eosin (H&E) staining, immunohistochemistry staining by anti human IgG, Fcγ fragment antibody, and viral genome copy measurement by quantitative PCR (qPCR) as described (Zhang et al, 2012). Mouse blood was centrifuged at 10K rpm for 5 minutes, and serums were used to determine alanine transaminase (ALT) and aspartate transaminase (AST) levels and sTGβRIIFc serum expression by ELISA as previously described (Zhang et al, 2012; Hu et al., 2012).

Liver immune response studies and serum LDH assay. Six-week old nude mice were injected with low dose (LD=$2.5\times10^{10}$ VPs/mouse) or medium dose (MD=$1.0\times10^{11}$ VPs/mouse) of adenoviral vectors via tail vein. One hour after injection, mice were anesthetized with Ketamine (25 mg/ml)/Xylazine (2 mg/ml) cocktail and 300 μl blood were withdrawn via the heart. Forty eight hours after virus injection, they were anesthetized again by isoflurane and euthanized after collecting blood samples. Mouse serums were used to determine Lactate Dehydrogenase (LDH) levels, IL-6 levels and TNF-α levels as published (Xu et al., 2014)

Unexpectedly, only the Lyp-1 modified constructs demonstrated virus stability and safety. Unpredictably, the Lyp-1 modified viruses also had the highest levels of transgene expression compared to the other constructs. The NGR peptide targeted virus was highly unstable and could not be generated. The REA virus was also very unstable frequently losing its transgene with almost negligible levels of transgene protein expression. The RGD construct made reduced transgene protein compared to the Lyp-1 constructs and the RGD virus was lethal in murine animal models when administered intravenously at doses that were well tolerated with the Lyp-1 viruses. These results are summarized in Table 1 below:

| Peptide Motif | Vector Stability | Transgene Expression > 500 ng/ml | Safety of $10^{10}$ VP IV Dose |
|---|---|---|---|
| Lyp-1 | Yes | Yes | Yes |
| RGD | Yes | Yes | No |
| NGR | No | No | NA |
| REA | No | No | NA |

Example 2

Transgene Expression Levels of Adenoviral Vectors with Genetically Modified Fibers Incorporating Various Peptide Motifs and Chimeric Hexon Modifications In vitro experiments were conducted in human MDA-MB-231, and MCF-7 breast tumor cells, and 4T1 mouse mammary tumor cells to compare transgene expression levels of Lyp-1 modified and control vectors. Infection of MDA-MB-231, MCF-7 (human cells) and mouse 4T1 cells with the vector resulted increased transgene expression of Lyp-1 modified adenoviral vectors in tumor cells.

MDA-MB-231, MCF-7, 4T1 cells were exposed to viral vectors ($2.5\times10^4$ VP/cell) and 48 hrs later, sTGFβRIIFc transgene expression levels were measured in the serum by ELISA. ***p<0.001, represents a highly significant increase in transgene expression for mHAdLyp.sT compared to the control Ad.sT).

Example 3

Figure 4:
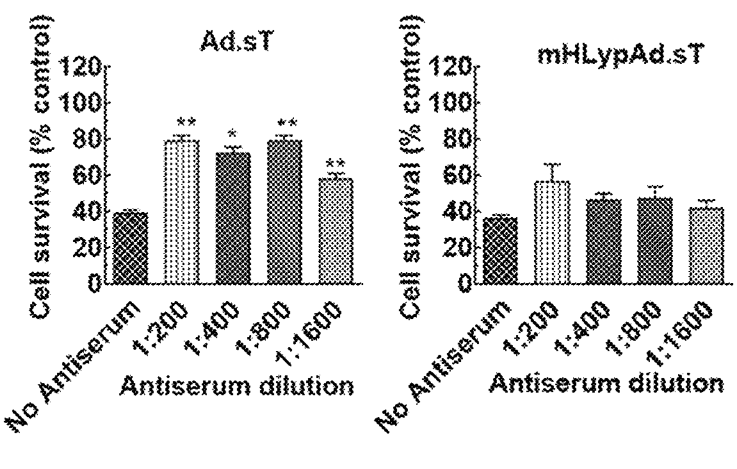
FIG. 4: Resistance to Neutralizing Antibodies of Adenoviral Vectors with Genetically Modified Fibers Incorporating Lyp-1 Peptide and Chimeric Hexon Modifications. Various dilutions of the anti-Ad5 antiserum were incubated with either the conventional Ad5 transgene expressing vector Ad.sT (left) or with the Lyp1 modified vector mHLypAd.sT (right) ($5\times10^7$ VPs) for 60 minutes. The samples were exposed to MDA-MB-231 cells plated in 96-wells ($10^3$ cells/well) for 7 days. The viral-induced cell killing was measured using sulforhodamine B (SRB) method. Shown are the cell survivals listed as the % of the untreated controls using these controls as 100% survival. *$p<0.05$, **$p<0.01$ are against no antiserum (control virus treatment alone) samples. Neutralizing Ad5 antiserum resulted in statistically significant decreased tumor cell killing by the conventional Ad5 transgene expressing adenoviral vector Ad.sT but had no statistically significant effect on mHLypAd.sT tumor cell killing at neutralizing titers ranging from 1:200 to 1:1600 dilutions.

Resistance to Neutralizing Antibodies of Adenoviral Vectors with Genetically Modified Fibers Incorporating Lyp-1 Peptide and Chimeric Hexon Modifications As depicted in FIG. 4, there was resistance to neutralizing antibodies of adenoviral vectors with genetically modified fibers incorporating Lyp-1 peptide and chimeric hexon modifications. Various dilutions of the anti-Ad5 antiserum were incubated with either the conventional Ad5 transgene expressing vector Ad.sT (left) or with the Lyp 1 modified vector mHLypAd.sT (right) ($5\times10^7$ VPs) for 60 minutes. The samples were exposed to MDA-MB-231 cells plated in 96-wells ($10^3$ cells/well) for 7 days. The viral-induced cell killing was measured using SRB method. Shown are the cell survivals listed as the % of the untreated controls using these controls as 100% survival. *p<0.05, **p<0.01 are against no antiserum (control virus treatment alone) samples. Neutralizing Ad5 antiserum resulted in statistically significant decreased tumor cell killing by the conventional Ad5 transgene expressing adenoviral vector Ad.sT but had no statistically significant effect on mHLypAd.sT tumor cell killing at neutralizing titers ranging from 1:200 to 1:1600 dilutions.

Example 4

Figure 5:
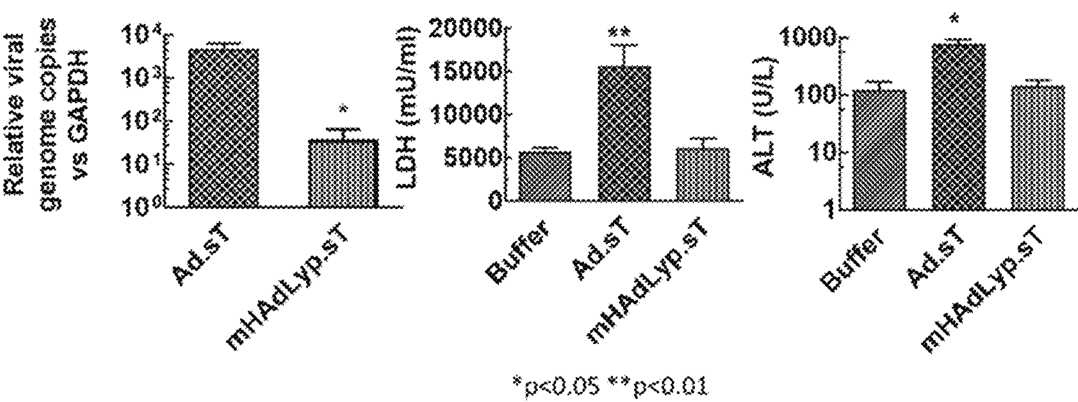
FIG. 5: Reduced hepatic uptake and hepatic/systemic toxicity of mHAdLyp.sT. Female nude mice were administered buffer or viral vectors ($5\times10^{10}$ VPs/mouse) via tail vein. After 48 hrs, liver and blood were collected. Ad genomic copies in the liver and serum levels of the liver enzymes LDH and ALT were measured and compared (n=4 mice per group). There was statistically significant lower liver uptake and lower serum LDH and ALT levels for the Lyp-1 modified mHAdLyp.sT vector compared to the conventional Ad5 transgene expressing adenoviral vector Ad.sT (*$p<0.05$ and **$p<0.01$).

In Vivo Safety of Adenoviral Vectors with Genetically Modified Fibers Incorporating Lyp-1 Peptide and Chimeric Hexon Modifications As shown in FIG. 5, intravenous delivery in nude mice of mHAdLyp.sT compared to corresponding Ad5 based viruses resulted in reduced liver uptake, by greater than 100-fold and resulted in reduced hepatic damage (alanine amino transferase (ALT) enzyme activity), and reduced systemic toxicity (Interleukin(IL)-6 production), and lactate dehydrogenase (LDH) activity). Female nude mice were administered buffer or viral vectors ($5\times10^{10}$ VPs/mouse) via tail vein. After 48 hrs, liver and blood were collected. Ad genomic copies in the liver and serum levels of the liver enzymes LDH and ALT were measured and compared (n=4 mice per group). There was a statistically significant lower liver uptake and lower serum LDH and ALT levels for the Lyp-1 modified mHAdLyp.sT vector compared to the conventional Ad5 transgene expressing adenoviral vector Ad.sT (*p<0.05 and **p<0.01).

Example 5

Figure 6A:
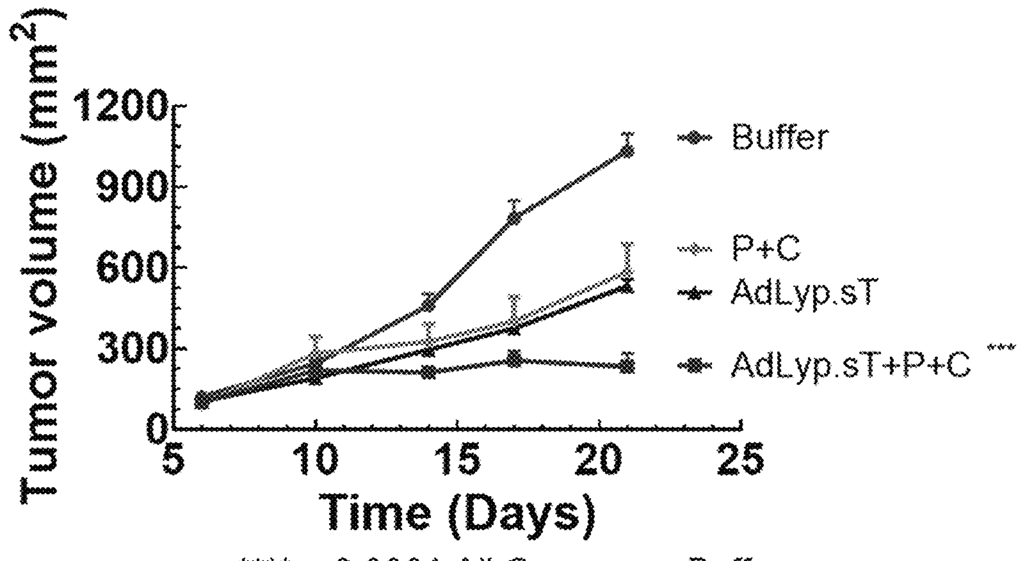
FIGS. 6A-6B: Synergy of Adenoviral Vectors with Genetically Modified Fibers Incorporating Lyp-1 Peptide and Chimeric Hexon Modifications and Immune Checkpoint Inhibitor Therapy. Experiments were conducted using intratumoral (IT) delivery of Ad5 based viruses—Ad.sT and AdLyp.sT; anti-PD-1, and anti-CTLA-4 alone or in combinations. Briefly, 4T1 cells were injected subcutaneously in female mice. On day 6, the primary tumor size was measured. On day 7, Ad.sT or AdLyp.sT (each dose, $2.5\times10^{10}$ VPs in 50 μl) were administered directly into the primary tumors. A repeat viral dose was given on day 9. On days 8, 10, 12, 14, and 16 anti-PD-1 (P), anti-CTLA-4 (C) were administered i.p. (P+C) (antibody dose 10 mg/kg of mouse weight). Primary tumor growth was monitored by caliper measurements on the days post treatment (FIG. 6A). There was enhanced efficacy of AdLyp.sT+P+C treatment compared to either P+C or AdLyp.sT therapy alone. The combined treatment with AdLyp.sT+P+C induced a large decrease in primary tumor volume, as compared to either P+C or AdLyp.sT therapy alone. A statistical analysis of variance (ANOVA) comparison of tumor volumes for each treatment, determined the anti-tumor effects of AdLyp.sT+P+C were synergistic (p-value<0.001). On day 25, mice were euthanized, lungs excised, and the number of lung metastases were counted to assess the systemic, abscopal effects of the primary tumor treatments (FIG. 6B). The combined treatment with AdLyp.sT+P+C induced a large decrease in lung metastases, as compared to either P+C or AdLyp.sT therapy alone. A statistical analysis of variance (ANOVA) comparison of tumor lung metastases for each treatment, determined the systemic abscopal anti-tumor effects of AdLyp.sT+P+C were synergistic (p-value<0.0025).

Synergy of Adenoviral Vectors with Genetically Modified Fibers Incorporating Lyp-1 Peptide and Chimeric Hexon Modifications and Immune Checkpoint Inhibitor Therapy Experiments were conducted using intra-tumoral (IT) delivery of Ad5 based viruses—Ad.sT and AdLyp.sT; anti- PD-1, and anti-CTLA-4 alone or in combinations. Briefly, 4T1 cells were injected subcutaneously in female mice. On day 6, the primary tumor size was measured. On day 7, Ad.sT or AdLyp.sT (each dose, $2.5\times10^{10}$ VPs in 50 μl) were administered directly into the primary tumors. A repeat viral dose was given on day 9. On days 8, 10, 12, 14, and 16 anti-PD-1 (P), anti-CTLA-4 (C) were administered i.p. (P+C) (antibody dose 10 mg/kg of mouse weight). Primary tumor growth was monitored by caliper measurements on the days post treatment as shown in FIG. 6A.

Figure 6B:
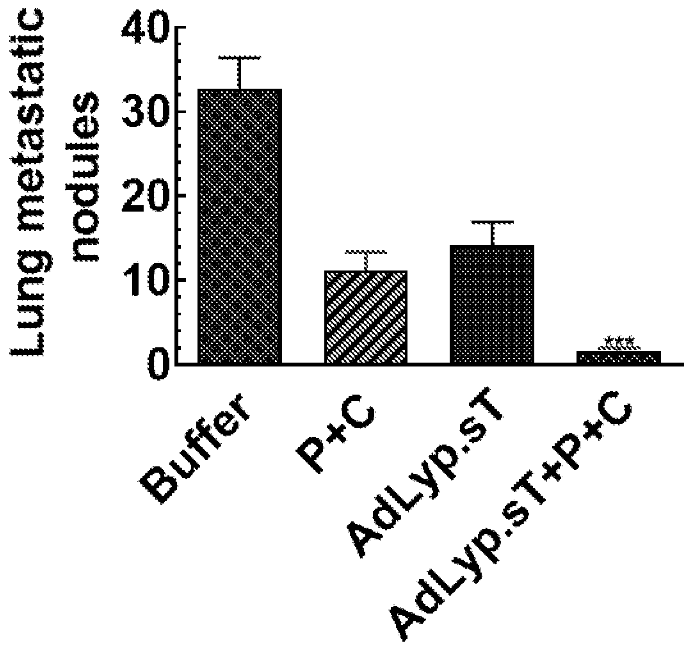

There was enhanced efficacy of AdLyp.sT+P+C treatment compared to either P+C or AdLyp.sT therapy alone. The combined treatment with AdLyp.sT+P+C induced a large decrease in primary tumor volume, as compared to either P+C or AdLyp.sT therapy alone. A statistical analysis of variance (ANOVA) comparison of tumor volumes for each treatment, determined the anti-tumor effects of AdLyp.sT+P+C were synergistic (p-value<0.001). On day 25, mice were euthanized, lungs excised, and the number of lung metastases were counted to assess the systemic, abscopal effects of the primary tumor treatments (FIG. 6B). The combined treatment with AdLyp.sT+P+C induced a large decrease in lung metastases, as compared to either P+C or AdLyp.sT therapy alone. A statistical analysis of variance (ANOVA) comparison of tumor lung metastases for each treatment, determined the systemic abscopal anti-tumor effects of AdLyp.sT+P+C were synergistic (p-value<0.0025).

Example 6

Adenoviral Vectors with Genetically Modified Fibers Incorporating Lyp-1 Peptide and Chimeric Hexon Modifications in Combination with Preferential CD122/132 Agonist(s) for Induction of Systemic Effects and Reversal of Resistance to Immune Checkpoint Inhibitor Immunotherapy The efficacy of combining a CD122/CD132 agonist with the adenoviral vector with a genetically modified fiber incorporating a Lyp-1 peptide motif for the induction of local and systemic effects for tumors resistant to immunotherapy was demonstrated in immunocompetent animal tumor models. The following treatment methods, doses, and schedules are utilized:

- Animals, tumor inoculation and measurements: In the mammary 4T1 tumor model, BALB/c mice were inoculated with 4T1-luc cells ($2\times10^6$ cells/mouse) (day 0) to establish subcutaneous tumors. When the palpable tumors were formed (approximately day 6), therapeutic interventions were initiated as described below. Tumor size was then determined by caliper measurements.
- Viral vectors: In the mammary 4T1 tumor model, mHAdLyp.sT (also known as Ad5/48LyP-TGFβR) was injected via tail vein (days 7 and 9, each dose $2\times10^{10}$ viral particles/mouse). Other LyP-1 modified viral vectors and routes of administration as described in Examples 4 and 5 may also be utilized.
- Preferential CD122/CD132 agonist treatment: In the mammary 4T1 tumor model, for the IL2 preferential CD122/CD132 agonist shown in FIG. 7, recombinant murine IL-2 (R&D Systems Minneapolis, MN) and S4B6-1 anti-mouse IL2 antibody (BioXcell, West Lebanon, NH) were mixed for 15 minutes at room temperature at a molar ratio 2:1. The IL-2/S4B6 mAb immunocomplexes were administered intraperitoneally (IP) at 2.5 IL2/dose on days 7 and 9.
- Immune Checkpoint Inhibitor Therapy: In the mammary 4T1 tumor model, anti-PD-L1 (BioXcell, West Lebanon, NH) was injected intraperitoneally on days 6, 8, and 10 (each dose 10 mg/kg mouse weight) dose.

Figure 7:
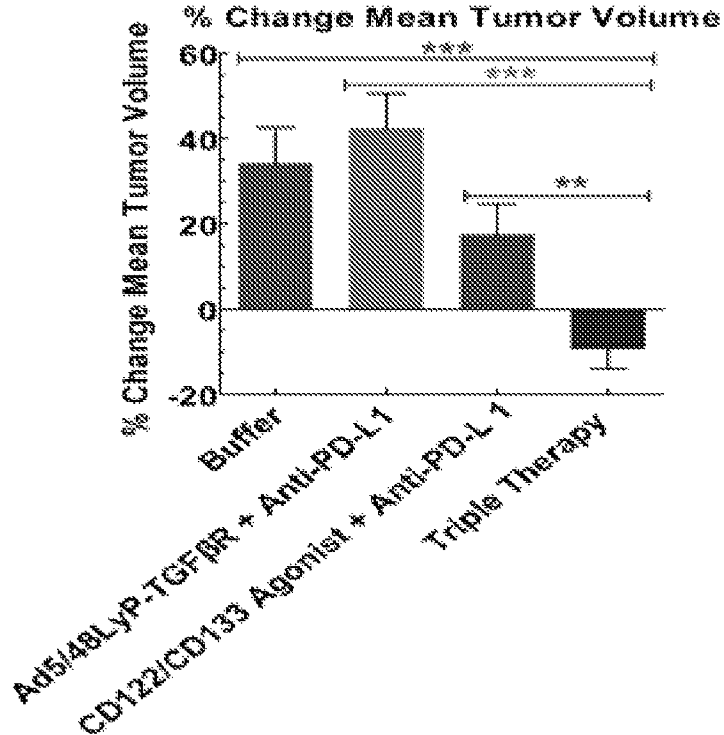
FIG. 7. Synergy of Adenoviral Vectors with Genetically Modified Fibers Incorporating Lyp-1 Peptide and Chimeric Hexon Modifications Combined with Immune Checkpoint Inhibitor and CD122/132 agonist Therapies. In the same 4T1 tumor model described in FIG. 6, remarkable and unexpected synergy was observed for the combination treatment comprising mHAdLyp.sT (also referred to as Ad5/48LyP-TGFβR) with anti-PD-L1 and CD122/CD132 agonist therapies. The "Triplet" immunotherapy combining mHAdLyp.sT (also referred to as Ad5/48LyP-TGFβR) with anti-PD-L1 and CD122/CD132 agonist was the only treatment combination that resulted in a mean reduction of tumor volume with statistically significant differences compared to the other treatment groups. This triplet treatment combination demonstrated an unexpected and more than additive synergy in decreasing tumor size as all other treatment combinations showed a mean increase in tumor volume compared to baseline measurements. Shown are the % change in mean tumor volume through day 11 in each treatment group (n=15 in each group). An analysis of variance (ANOVA) revealed there was a highly statistically significant difference between these means (p<0.0001) and the "Triplet" immunotherapy combining mHAdLyp.sT (also referred to as Ad5/48LyP-TGFβR) with anti-PD-L1 and CD122/CD132 agonist was the only treatment demonstrating a statistically significant change compared to the control buffer (p=0.0004). Additional statistical evaluations revealed the following statistically significant differences between the mean values by t test analyses: *p<0.001 triple therapy vs buffer group, *p<0.001 triple therapy vs Ad5/48LyP-TGFβR+Anti-PD-L1 (double therapy), **p<0.001 triple therapy vs Anti-PD-L1 and CD122/CD132 agonists (double therapy). With the exception of the triplet therapy, none of the other treatment combinations were effective in decreasing mean tumor size which increased in all other therapy and control groups.

In the mammary 4T1 tumor model, combination therapies comprising mHAdLyp.sT (also referred to as Ad5/48LyP-TGFβR) with anti-PD-L1 and IL2 derived preferential CD122/CD132 agonist treatments are shown in FIG. 7. Remarkably, there was unexpected synergy for the "Triplet" immunotherapy combining mHAdLyp.sT (also referred to as Ad5/48LyP-TGFβR) with anti-PD-L1 and CD122/CD132 agonist therapies which was the only treatment combination that resulted in a mean reduction of tumor volume with statistically significant differences compared to the other treatment groups. This triplet treatment combination demonstrated an unexpected and more than additive synergy in decreasing tumor size as all other treatment combinations showed a mean increase in tumor volume compared to baseline measurements. Shown in FIG. 7 are the % change in mean tumor volume through day 11 for each treatment group (n=15 in each group). An analysis of variance (ANOVA) revealed there was a highly statistically significant difference between these means (p<0.0001) and the "Triplet" immunotherapy combining mHAdLyp.sT (also referred to as Ad5/48LyP-TGFβR) with anti-PD-L1 and CD122/CD132 agonist was the only treatment demonstrating a statistically significant change compared to the control buffer (p=0.0004). Additional statistical evaluations revealed the following statistically significant differences between the mean values by t test analyses: *p<0.001 triple therapy vs buffer group, *p<0.001 triple therapy vs Ad5/48LyP-TGFβR+Anti-PD-L 1 (double therapy), **p<0.001 triple therapy vs Anti-PD-L1 and CD122/CD132 agonists (double therapy). With the exception of the triplet therapy, none of the other treatment combinations were effective in decreasing mean tumor size which increased in all other therapy and control groups. None of the other treatment combinations were effective in decreasing mean tumor volume which increased in all other therapy and control groups indicating the immunotherapy resistant nature of the 4T1 tumor model consistent with the majority of human tumors that also do not respond to immunotherapy.

In other tumor models, C57BL/6 (B6) mice (6-8 weeks of age obtained from Charles River Labs) are utilized. Animals are injected into the right flank, subcutaneously, with B16F10 melanoma cells (ATCC, $5\times10^5$ cells/mouse) to form the "Primary Tumor". Treatment is begun when tumors had reached approximately 50 $mm^3$ in size and this is termed treatment Day 1. Tumor growth is monitored by measuring the length (L) and width (w) of the tumor, and tumor volume calculated using the following formula: volume=$0.523L(w)^2$. Animals are monitored for up to 60 days, and sacrificed when tumors reached approximately 2000 $mm^3$.

- For IL15 CD122/CD132 agonist, mouse IL-15 and IL-15-R alpha-Fc are incubated together at 37 C for 30 minutes and this preferential CD122/CD132 agonist immunocomplex is injected i.v. for two consecutive days once tumors become palpable. An alternate schedule is administration of the IL-15 immune complex injected IP on days 1 and 10. For IL-15 immunocomplex studies, recombinant murine IL-15 (Peprotech, Rocky Hill, CT, USA) is used in the in vivo studies at doses of 2 μg/injection recombinant murine IL-15 once per week by intravenous injection. Recombinant mouse IL-15 R alpha Fc Chimera Protein is obtained from R&D Systems (Minneapolis, MN) and used at doses equimolar to IL-15 cytokine (12 ug/injection of IL-15-Rα-Fc for each 2 ug IL-15 protein in immune complex).

For B16F10 models, murine IL-2 (eBioscience or R&D Systems Minneapolis, MN) is mixed with the S4B6-1 anti-mouse IL2 antibody (Bioxcell, West Lebanon, NH or BD Biosciences) at a molar ratio 2:1 to generate the preferential CD122/CD132 agonist immunocomplex. For studies involving human T cells, human IL-2 is mixed with MAB602 anti-human IL-2 antibody (R&D Systems). The IL-2/S4B6 or IL-2/MAB602 mAb immunocomplexes are administered intraperitoneally (FP) at 2.5 μg IL2/dose on days 2, 6, and 10. Alternatively, IL-2/S4B6 mAb immunocomplexes were injected on days 2-6 (1.0 μg IL2/dose). Immunocomplexes are prepared by incubating anti-IL-2 monoclonal with IL-2 for 15 minutes at room temperature.

Reversal of Resistance to Prior Immunotherapy: In other tumor models, the ability of combined adenoviral vector with a genetically modified fiber incorporating a Lyp-1 peptide motif and preferential CD122/CD132 treatment to reverse resistance to prior immunotherapy is also demonstrated. To mimic the common clinical condition of tumor progression during immune checkpoint inhibitor therapy, anti-PD1 treatment, at a dose of 10 mg/kg, is begun intraperitoneally on Day 1 and administered every 3 days up to day 31. In some experiments, to evaluate the effects of combined adenoviral vector with a genetically modified fiber incorporating a Lyp-1 peptide motif and CD122/CD132 therapy in tumors resistant to prior immunotherapy, the combined treatment is initiated after tumor progression on anti-PD-1 therapy with the first adenoviral vector with a genetically modified fiber incorporating a Lyp-1 peptide motif and CD122/CD132 therapy dose being given 2 to 3 days after the initiation of anti-PD-1 treatment. In other experiments, combined adenoviral vector with a genetically modified fiber incorporating a Lyp-1 peptide motif and CD122/CD132 therapy is initiated concurrently with immune checkpoint inhibitors as initial treatment. In other experiments, the first adenoviral vector with a genetically modified fiber incorporating a Lyp-1 peptide motif dose is given 2 to 3 days after the initiation of combined preferential CD122/CD132 therapy and anti-PD-1 treatment. These studies are performed in tumors known to be highly resistant to immune based treatments. The B16F10 and B16 melanoma models are known to be highly resistant to immunotherapy. In these models, tumors progress on immune checkpoint inhibitor therapy similarly to control treatment with Phosphate Buffered Saline (PBS). The anti-mouse PD-1 antibody (CD279) specifically produced for use in vivo is purchased from BioXcell (catalog #BE0146) as are antibodies to anti-PD-L1 and the immune modulator anti-LAG-3. Anti-mouse-PD-L1 antibody (clone 9G2; Biolegend) and/or anti-CTLA-4 antibody (clone UC10-4F10-11; Altor) are administered IP at 100 μg per injection twice a week for 2 weeks.

In the above examples, treatment efficacy and their synergistic interactions are demonstrated by measurement of tumor volumes in primary and/or contralateral tumors and their statistical analyses by T test, analysis of variance (ANOVA), Kruskal-Wallis ANOVA; and by comparisons of survival using Kaplan-Meier and log rank tests.

Summary: The animal study populations described in the Examples use highly aggressive forms of cancer, known to be generally resistant to immune therapies. Surprisingly, adenoviral vector with a genetically modified fiber incorporating a Lyp-1 peptide motif treatment resulted in higher levels of transgene expression, lower hepatotoxicity and lethality following systemic administration compared to conventional adenoviral vectors. In addition, adenoviral vector with a genetically modified fiber incorporating a Lyp-1 peptide motif treatment either alone or combined with immune checkpoint inhibitor and preferential CD122/CD132 therapy reverses resistance to previous immune therapy, demonstrated unexpected synergies and the combined therapies induced superior abscopal effects on distant tumors that were not intra-tumorally treated with adenoviral vector with a genetically modified fiber incorporating a Lyp-1 peptide motif.

All the methods disclosed and claimed herein can be made and executed without undue experimentation considering the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Aghi et al., *Cancer Res.*, 59:3861-3865, 1999.

Aksentijevich et al. *Human Gene Ther.* 7:1111, 1996.

Baichwal and Sugden, In: *Gene Transfer*, Kucherlapati R, ed., New York, Plenum Press, pp. 1 17-148, 1986.

Bailey and Levine, *J. Pharm. Biomed. Anal.*, 11: 285-292, 1993.

Bouvet et al., *Cancer Res.*, 58:2288-2292, 1998.

Buller et al., *Cancer Gene Therapy*, 9: 553-566, 2002.

Camacho et al. *J Clin Oncology*, 22(145), 2004.

Carroll et al., *Mol Cancer Therapeutics*, 1:49-60, 2001.

Caudell et al., *J Immunol.*, 168:6041-6046, 2002.

Chada et al., *Cancer Gene Ther.*, 13:490-502, 2006.444-448, 1998.

Chada et al., *Cancer Gene Ther.*, 13:490-502, 2006.444-448, 1998.

Chase et al., *Nat. Biotechnol.*, 16:

Chen and Okayama, *Mol. Cell. Biol.* 7:2745-2752, 1987.

Choi et al. *Gene Therapy*, 17: 190-201, 2010.

Corrales et al., *Cell Reports*, 11, 1018-1030, 2015.

Couch et al, *Am. Rev. Resp. Dis.*, 88:394-403, 1963.

Dmitriev et al., *Journal of Virology Dec*, 72 (12) 9706-9713, 1998.

Doronin et al., *Virology*, 305:378-387, 2003.

Dubois et al., 2008.

European Patent Application No. EP2403951A2

European Patent Application No. EP2724728A1

Fraley et al, *Proc. Nat'l Acad. Sci.* 76:3348-3352, 1979.

Fujiwara et al., *J Natl Cancer Inst*, 86: 1458-1462, 1994.

Ghiringhelli et al., *Biomed. J.*, 38:111-116, 2015.

Graham and Van Der Eb, *Virology*, 52:456-467, 1973.

Gurnani et al., *Cancer Chemother Pharmacol.*, 44(2): 143-151, 1999.

Harland and Weintraub, *J. Cell Biol*, 101:1094-1099, 1985.

Hartwell et al., *Science,* 266: 1821-1828, 1994.
Howe et al., *Mol Ther* 2, 485-495, 2000.
Hu et al., *Hum Gene Ther* 23: 871-882, 2012.
Hu et al., *Hum Gene Ther* 21, 1623-1629, 2010.
Hurwitz et al. *Proc Natl Acad Sci.* 95(17): 10067-10071, 1998.
Hynes and Ferretti, *Methods Enzymol.,* 235: 606-616, 1994.
Iannello et al., *J Experimental Medicine,* 210(10):2057-2069.
IMLYGIC™ [package insert]. Amgen, Inc., Thousand Oaks, CA; October 2015.
Inoue et al., *Cancer Letters,* 157:105-112, 2000.
International Patent Application No. WO1995001994.
International Patent Application No. WO1998042752.
International Patent Application No. WO2000037504.
International Patent Application No. WO2001014424.
International Patent Application No. WO2004058801.
International Patent Publication No. WO 2005/003168.
International Patent Publication No. WO 2005/009465.
International Patent Publication No. WO 2006/003179.
International Patent Publication No. PCT/KR2011/004693
International Patent Publication No. WO 2006/072625.
International Patent Publication No. WO 2006/072626.
International Patent Publication No. WO 2007/042573.
International Patent Publication No. WO 2008/084106.
International Patent Publication No. WO 2010/065939.
International Patent Publication No. WO 2012/071411.
International Patent Publication No. WO 2012/160448.
International Patent Publication No. WO 2012009703.
International Patent Publication No. WO1995011986.
International Patent Publication No. WO2014/047350
International Patent Publication No. WO2014/047350.
International Patent Publication No. WO2014/138314
International Patent Publication No. WO2014/138314.
International Patent Publication No. WO2014100014A1
International Patent Publication No. WO2015/016718.
International Patent Publication No. WO2015/027163
International Patent Publication No. WO2015/027163.
International Patent Publication No. WO2015/150809.
International Patent Publication No. WO2016/009017
International Patent Publication No. WO2016/009017.
Jiang et al., *Proc. Natl. Acad. Sci.,* 93:9160-9165.
Katayoseet et al., *Clinical Cancer Res.* 1: 889-898, 1995.
Kawabe et al., *Mol Ther.* 6(5):637-44, 2002.
Kawabe et al., *Mol. Ther.* 6(5): 637-644, 2002.
Kim et al. *Journal of the National Cancer Institute,* 98(20): 1482-1493, 2006.
Kotin et al, *Proc. Natl. Acad. Sci. USA,* 87:221 1-2215, 1990.
Kreil, *Protein Sci.,* 4:1666-1669, 1995.
Li Phase 1 Clinical Trial, *Gene Therapy;* 16 376-382, 2009.
Lichtenstein et al, *Int. Rev. Immunol.,* 23:75-111, 2004.
Liu et al *J Biol. Chem.,* 270:24864, 1995.
Lui et al., *Gene Therapy,* 10:292-303, 2003.
Lui et al., *Gene Therapy,* 10:292-303, 2003.
Mann et al, *Cell,* 33:153-159, 1983.
Markowitz et al., *J. Virol.,* 62: 1 120-1 124, 1988.
McLaughlin et al, *J. Virol.,* 62:1963-1973, 1988.
Mellman et al., *Nature* 480:480-489, 2011.
Mellman et al., *Nature,* 480:480-489, 2011.
Mhashilkar et al., *Mol. Medicine* 7(4): 271-282, 2001.
Miyahara et al., *Cancer Gene Therapy,* 13:753-761, 2006.
Mokyr et al., *Cancer Res.,* 58:5301-5304, 1998.
MultiVir Inc., Form S-1 Registration Statement, U.S. Securities and Exchange Commission, 2015
Muzyczka, *Curr. Top. Microbiol Immunol,* 158:97-129, 1992.
Nemunaiti et al., *Clin Cancer Res.,* 15(24):7719-25, 2009.
Nicolas and Rubenstein, In: *Vectors*: A survey of molecular cloning vectors and their uses, Rodriguez and Denhardt (eds.), Stoneham: Butterworth, pp. 493-513, 1988.
Nicolau and Sene, *Biochim. Biophys. Acta,* 721:185-190, 1982.
Nicolau et al. *Methods Enzymol,* 149:157-176, 1987.
Nishikawa et al., *Mol. Ther.,* 9(8):818-828, 2004b.
Nishikawa et al., *Oncogene,* 23(42): 7125-7131, 2004a.
Nishizaki M, et al., *Clin. Can. Res.,* 5: 1015-1023, 1999.
Ohashi M, et al., *Gut,* 44:366-371, 1999.
Pardoll, *Nat Rev Cancer,* 12(4): 252-64, 2012.
Pardoll, *Nature Rev Cancer,* 12:252-264, 2012.
Philip et al. *J. Biol. Chem.,* 268: 16087, 1993.
Qin, X., et al., *Biol Reprod.,* 56:800-11, 1997a.
Qin, X., et al., *Biol Reprod.,* 56:812-20, 1997b.
Ridgeway, In: *Vectors*: A survey of molecular cloning vectors and their uses, Rodriguez R L. Denhardt D T, ed., Stoneham:Butterworth, pp. 467-492, 1988.
Rippe et al, *Mol. Cell Biol,* 10:689-695, 1990.
Rosenberg et al., *Nat Med.,* 10(19): 909-15, 2004.
Samulski et al, *EMBO J* 10:3941-3950, 1991.
Samulski et al, *J Virol,* 63:3822-3828, 1989.
Sherwood et al., *Endocrinology* 114:806-13, 1984.
Sobol R E, et al., Chapter 11: Tp53 Gene Therapy for Cancer Treatment and Prevention, NY: Springer Science+Business Media, 2013.
Solodin et al, *Biochemistry,* 34: 13537, 1995.
Spitz et al., *Clin Cancer Research,* 2: 1665-1671, 1996.
Swisher et al., *Clin Cancer Research,* 9:93-101, 2003.
Tatebe S, et al., *Int. J Oncol.,* 15: 229-235, 1999.
Tatebe S, et al., *Int. J Oncol.,* 15: 229-235, 1999.
Tchekmedyian et al., *Oncology,* 29(12):990-1002, 2015.
Temin, n: *Gene Transfer*, Kucherlapati (ed.), New York: Plenum Press, pp. 149-188, 1986.
Textor et al., *Cancer Res.,* 71(18):5998-6009, 2011.
Thierry et al. *Proc. Natl. Acad. Sci.,* 92(21):9742-6, 1995.
Timiryasova et al., *Biotechniques.* 31:534, 6, 8-40, 2001.
Toda et al., *Mol. Therapy,* 2(4): 324-329, 2000.
Tollefson et al., *J. Virol.,* 70: 2296-2306, 1996.
Top et al, *J. Infect. Dis.,* 124:155-160, 1971.
Tsukamoto et al, *Nature Genetics,* 9:243, 1995.
U.S. Patent Application No. US20110008369.
U.S. Patent Application No. US2014022021.
U.S. Patent Application No. US20140294898.
U.S. Pat. No. 4,797,368.
U.S. Pat. No. 4,835,251.
U.S. Pat. No. 5,023,321.
U.S. Pat. No. 5,139,941.
U.S. Pat. No. 5,302,523.
U.S. Pat. No. 5,384,253.
U.S. Pat. No. 5,464,765.
U.S. Pat. No. 5,580,859.
U.S. Pat. No. 5,589,466.
U.S. Pat. No. 5,656,610.
U.S. Pat. No. 5,702,932.
U.S. Pat. No. 5,736,524.
U.S. Pat. No. 5,780,448.
U.S. Pat. No. 5,789,215.
U.S. Pat. No. 5,811,395
U.S. Pat. No. 5,925,565
U.S. Pat. No. 5,935,819
U.S. Pat. No. 5,945,100
U.S. Pat. No. 5,981,274
U.S. Pat. No. 5,994,136
U.S. Pat. No. 5,994,624
U.S. Pat. No. 6,013,516

U.S. Pat. No. 6,207,156
U.S. Pat. No. 7,223,593
U.S. Pat. No. 7,537,924
U.S. Pat. No. 8,017,114
U.S. Pat. No. 8,119,129
U.S. Pat. No. 8,329,867
U.S. Pat. No. 8,354,509
U.S. Pat. No. 9,746,471
U.S. Patent Publication No. US 2017/0044229
U.S. Patent Publication No. US20060257361
U.S. Patent Publication No. US20070160578
U.S. Patent Publication No. US2011/0039778.
U.S. Patent Publication No. US2015/0202290
U.S. Patent Publication No. US2015/0202290.
U.S. Patent Publication No. US20170183403
U.S. Pat. No. 8,067,567
Vincent et al., *Cancer Res.,* 70(8):3052-3061, 2010.
Waku et al., *J Immunol.,* 165:5884-5890, 2000.
Xu et al, *Mol Ther* 22: 1404-1417, 2014.
Xu et al. *Gene Therapy,* 22(3): 31-40, 2015.
Xu et al., *J Gastroenterol.,* 48(2):203-13, 2013.
Xue et al., *Nature,* 445(7128):656-660, 2007.
Young et al., *Cancer Gene Ther.,* 20(9): 531-537, 2013.
Yu and Fang, *Current Cancer Drug Targets;* 7 659-670, 2007.
Yun et al., *Human Gene Therapy* 23:609-622, 2012.
Zeimet and Marth, *The Lancer Oncology,* 7:415-422, 2003.
Zhang et al. *Cancer Gene Ther* 19: 630-636, 2012.
Zhang et al., *Cancer Gene Ther,* 22:17-22, 2015.
Zhang et al., *Cancer Gene Ther.,* 1:5-13, 1994.

What is claimed is:

1. A pharmaceutical composition comprising (a) Lyp-1 chimeric adenovirus particles encoded by a chimeric adenovirus E1A 01/07 mutant vector comprising a genetically modified fiber gene encoding a fiber incorporating a LyP-1 peptide within the HI loop of the fiber, wherein the vector encodes a soluble TGFβ receptor II Fc fusion protein (sTGFβRIIFc) and Adenoviral 5/Adenoviral 48 (Ad5/48) chimeric hexon, (b) at least one CD122/CD132 agonist selected from the group consisting of an IL-2/anti-IL-2 immune complex, an IL-15/anti-IL-15 immune complex, an IL-15/IL-15 Receptor α-IgG1-Fc (IL-15/IL-15Rα-IgG1-Fc) immune complex, PEGylated IL-2, PEGylated IL-15, IL-2 mutein and/or IL-15 mutein, and (c) at least one immune checkpoint inhibitor.

2. The composition of claim 1, wherein the vector further comprises a heterologous gene.

3. The composition of claim 2, wherein the heterologous gene encodes a soluble decoy receptor, tumor suppressor, an immune stimulating sequence, anti-angiogenic sequence, prodrug activating sequence, proapoptotic sequence, chemotherapy sensitizing sequence, radiation sensitizing sequence, miRNA, siRNA, anti-sense RNA, ribozyme or clustered regularly interspaced short palindromic repeats (CRISPR) gene editing sequence.

4. The composition of claim 3, wherein the heterologous gene encodes melanoma differentiation associated gene-7 (MDA-7) and/or p53.

5. The pharmaceutical composition of claim 1, wherein the at least one checkpoint inhibitor is selected from an inhibitor of CTLA-4, PD-1, PD-L1, PD-L2, LAG-3, BTLA, B7H3, B7H4, TIM3, KIR, or A2aR.

6. The pharmaceutical composition of claim 1, wherein the at least one CD122/CD132 agonist is selected from the group consisting of an IL-2/anti-IL-2 immune complex, an IL-15/anti-IL-15 immune complex, and an IL-15/IL-15 Receptor α-IgG1-Fc (IL-15/IL-15Rα-IgG1-Fc) immune complex, and the at least one immune checkpoint inhibitor is selected from an inhibitor of CTLA-4, PD-1, and PD-L1.

* * * * *